United States Patent
Maguire et al.

(10) Patent No.: US 6,752,805 B2
(45) Date of Patent: *Jun. 22, 2004

(54) SURGICAL ABLATION PROBE FOR FORMING A CIRCUMFERENTIAL LESION

(75) Inventors: Mark A. Maguire, San Mateo, CA (US); Michael R. Ross, Hillsborough, CA (US)

(73) Assignee: Atrionix, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/877,620

(22) Filed: Jun. 8, 2001

(65) Prior Publication Data

US 2002/0019627 A1 Feb. 14, 2002

Related U.S. Application Data

(60) Provisional application No. 60/212,879, filed on Jun. 13, 2000.

(51) Int. Cl.[7] .............................................. A61B 18/18
(52) U.S. Cl. .......................................... 606/41; 606/32
(58) Field of Search ........................ 606/15, 32, 40–41, 606/45–48

(56) References Cited

U.S. PATENT DOCUMENTS

| 3,781,781 A | 12/1973 | Groves, Jr. |
| 3,938,502 A | 2/1976 | Born |
| 4,117,836 A | 10/1978 | Erikson |
| 4,316,472 A | 2/1982 | Mirowski et al. |
| 4,411,266 A | 10/1983 | Cosman |
| 4,449,528 A | 5/1984 | Auth |
| 4,522,205 A | 6/1985 | Taylor |
| 4,569,801 A | 2/1986 | Molloy |
| 4,641,649 A | 2/1987 | Walinsky |
| 4,660,571 A | 4/1987 | Hess et al. |

(List continued on next page.)

FOREIGN PATENT DOCUMENTS

| EP | 0 623 360 B1 | 3/1999 |
| WO | WO 93/16632 A1 | 9/1993 |
| WO | WO 93/20767 | 10/1993 |
| WO | WO 93/20770 A2 | 10/1993 |
| WO | WO 93/20886 A1 | 10/1993 |

(List continued on next page.)

OTHER PUBLICATIONS

Diederich, C.J., et al., "Induction of Hyperthremia Using an Intracavitary Multielement Ultrasonic Applicator," Transactions in Biomedical Engineering, vol. 36 No. 4 1989.

(List continued on next page.)

*Primary Examiner*—Roy D. Gibson
*Assistant Examiner*—Peter J Vrettakos

(57) ABSTRACT

This invention is a circumferential ablation device assembly which is adapted to form a circumferential conduction block in a pulmonary vein. The assembly generally comprises a handheld surgical ablation probe having a rigid shaft for insertion through a patient's chest and a circumferential ablation element mounted on the distal end portion of the shaft. The circumferential ablation element is adapted to ablate a circumferential region of tissue along a pulmonary vein wall which circumscribes the pulmonary vein lumen. The circumferential ablation element includes an expandable member for anchoring the distal end portion of the shaft in a body structure and an ultrasound transducer disposed within the expandable member for emitting ultrasonic energy to ablate the tissue in the pulmonary vein.

22 Claims, 32 Drawing Sheets

U.S. PATENT DOCUMENTS

| | | |
|---|---|---|
| 4,662,368 A | 5/1987 | Hussein |
| 4,669,469 A | 6/1987 | Gifford, III et al. |
| 4,672,962 A | 6/1987 | Hershenson |
| 4,673,563 A | 6/1987 | Berne |
| 4,676,258 A | 6/1987 | Inokuchi et al. |
| 4,699,147 A | 10/1987 | Chilson et al. |
| 4,757,820 A | 7/1988 | Itoh |
| 4,762,129 A | 8/1988 | Bonzel |
| 4,790,311 A | 12/1988 | Ruiz |
| 4,807,620 A | 2/1989 | Strul et al. |
| 4,841,979 A | 6/1989 | Dow et al. |
| 4,882,777 A | 11/1989 | Narula |
| 4,898,591 A | 2/1990 | Jang et al. |
| 4,917,096 A | 4/1990 | Englehart |
| 4,924,863 A | 5/1990 | Sterzer |
| 4,936,281 A | 6/1990 | Stasz |
| 4,940,064 A | 7/1990 | Desai |
| 4,945,912 A | 8/1990 | Langberg |
| 4,951,677 A | 8/1990 | Crowley et al. |
| 4,976,711 A | 12/1990 | Parins et al. |
| 4,998,933 A | 3/1991 | Eggers |
| 5,000,185 A | 3/1991 | Yock |
| 5,002,059 A | 3/1991 | Crowley et al. |
| 5,035,694 A | 7/1991 | Kasprzyk |
| 5,078,717 A | 1/1992 | Parins et al. |
| 5,078,736 A | 1/1992 | Behl |
| 5,090,958 A | 2/1992 | Sahota |
| 5,104,393 A | 4/1992 | Isner |
| 5,131,397 A | 7/1992 | Crowley |
| 5,147,355 A | 9/1992 | Friedman et al. |
| 5,156,157 A | 10/1992 | Valenta, Jr. et al. |
| 5,178,618 A | 1/1993 | Kandarpa |
| 5,186,177 A | 2/1993 | O'Donnell et al. |
| 5,190,540 A | 3/1993 | Lee |
| 5,195,990 A | 3/1993 | Weldon |
| 5,209,229 A | 5/1993 | Gilli |
| 5,222,501 A | 6/1993 | Ideker et al. |
| 5,226,430 A | 7/1993 | Spears |
| 5,228,442 A | 7/1993 | Imran |
| 5,231,995 A | 8/1993 | Desai |
| 5,255,679 A | 10/1993 | Imran |
| 5,263,493 A | 11/1993 | Avitall |
| 5,281,215 A | 1/1994 | Milder |
| 5,292,321 A | 3/1994 | Lee |
| 5,293,868 A | 3/1994 | Nardella |
| 5,293,869 A | 3/1994 | Edwards |
| 5,295,484 A | 3/1994 | Marcus |
| 5,300,085 A | 4/1994 | Yock |
| 5,313,943 A | 5/1994 | Houser et al. |
| 5,324,255 A | 6/1994 | Passafaro et al. |
| 5,324,284 A | 6/1994 | Imran |
| 5,325,860 A | 7/1994 | Seward et al. |
| 5,331,966 A | 7/1994 | Bennett et al. |
| 5,342,292 A | 8/1994 | Nita et al. |
| 5,344,435 A | 9/1994 | Turner et al. |
| 5,345,936 A | 9/1994 | Pomeranz et al. |
| 5,345,940 A | 9/1994 | Seward et al. |
| 5,348,554 A | 9/1994 | Imran |
| 5,368,035 A | 11/1994 | Hamm et al. |
| 5,368,557 A | 11/1994 | Nita et al. |
| 5,368,558 A | 11/1994 | Nita |
| 5,370,678 A | 12/1994 | Edwards et al. |
| 5,372,138 A | 12/1994 | Crowley et al. |
| 5,385,148 A | 1/1995 | Lesh et al. |
| 5,385,544 A | 1/1995 | Edwards et al. |
| 5,391,197 A | 2/1995 | Burdette et al. |
| 5,409,000 A | 4/1995 | Imran |
| 5,411,524 A | 5/1995 | Rahul |
| 5,421,338 A | 6/1995 | Crowley et al. |
| 5,423,808 A | 6/1995 | Edwards et al. |
| 5,423,811 A | 6/1995 | Imran |
| 5,427,119 A | 6/1995 | Swartz et al. |
| 5,431,649 A | 7/1995 | Mulier et al. |
| 5,433,708 A | 7/1995 | Nichols et al. |
| 5,437,664 A | 8/1995 | Cohen et al. |
| 5,447,509 A | 9/1995 | Mills et al. |
| 5,449,380 A | 9/1995 | Chin |
| 5,454,373 A | 10/1995 | Koger et al. |
| 5,456,682 A | 10/1995 | Edwards et al. |
| 5,465,716 A | 11/1995 | Avitall |
| 5,474,530 A | 12/1995 | Passafaro et al. |
| 5,484,400 A | 1/1996 | Edwards et al. |
| 5,487,385 A | 1/1996 | Avitall |
| 5,496,312 A | 3/1996 | Klicek |
| 5,496,346 A | 3/1996 | Horzewski et al. |
| 5,497,774 A | 3/1996 | Swartz et al. |
| 5,501,227 A | 3/1996 | Yock |
| 5,505,702 A | 4/1996 | Arney |
| 5,505,730 A | 4/1996 | Edwards |
| 5,509,900 A | 4/1996 | Kirkman |
| 5,522,873 A | 6/1996 | Jackman et al. |
| 5,540,679 A | 7/1996 | Fram et al. |
| 5,545,161 A | 8/1996 | Imran |
| 5,545,193 A | 8/1996 | Fleischman |
| 5,549,661 A | 8/1996 | Kordis |
| 5,558,672 A | 9/1996 | Edwards |
| 5,562,720 A | 10/1996 | Stern |
| 5,564,440 A | 10/1996 | Swartz |
| 5,569,241 A | 10/1996 | Edwards |
| 5,571,088 A | 11/1996 | Lennox et al. |
| 5,571,159 A | 11/1996 | Alt |
| 5,575,766 A | 11/1996 | Swartz |
| 5,575,772 A | 11/1996 | Lennox |
| 5,575,788 A | 11/1996 | Baker et al. |
| 5,575,810 A | 11/1996 | Swanson |
| 5,582,609 A | 12/1996 | Swanson |
| 5,588,432 A | 12/1996 | Crowley |
| 5,606,974 A | 3/1997 | Castellano |
| 5,607,422 A | 3/1997 | Smeets et al. |
| 5,617,854 A | 4/1997 | Munsif |
| 5,620,479 A | 4/1997 | Diederich |
| 5,630,837 A | 5/1997 | Crowley |
| 5,642,736 A | 7/1997 | Avitall |
| 5,645,082 A | 7/1997 | Sung et al. |
| 5,658,278 A | 8/1997 | Imran et al. |
| 5,673,695 A | 10/1997 | McGee et al. |
| 5,676,662 A | 10/1997 | Fleischhacker et al. |
| 5,680,860 A | 10/1997 | Imran |
| 5,683,445 A | 11/1997 | Swoyer |
| 5,685,322 A | 11/1997 | Sung et al. |
| 5,685,839 A | 11/1997 | Edwards et al. |
| 5,687,723 A | 11/1997 | Avitall |
| 5,687,729 A | 11/1997 | Schaetzle |
| 5,688,267 A | 11/1997 | Panescu et al. |
| 5,690,611 A | 11/1997 | Swartz et al. |
| 5,693,078 A | 12/1997 | Desai et al. |
| 5,697,925 A | 12/1997 | Taylor |
| 5,697,927 A | 12/1997 | Imran et al. |
| 5,702,438 A | 12/1997 | Avitall |
| 5,715,818 A | 2/1998 | Swartz et al. |
| 5,716,389 A | 2/1998 | Walinsky et al. |
| 5,718,231 A | 2/1998 | Dewhurst et al. |
| 5,718,241 A | 2/1998 | Ben-Haim et al. |
| 5,718,701 A | 2/1998 | Shai et al. |
| 5,720,775 A | 2/1998 | Larnard |
| 5,722,401 A | 3/1998 | Pietroski et al. |
| 5,722,403 A | 3/1998 | McGee |
| 5,722,963 A | 3/1998 | Lurie et al. |
| 5,725,494 A | 3/1998 | Brisken |
| 5,725,512 A | 3/1998 | Swartz et al. |
| 5,728,062 A | 3/1998 | Brisken |

| | | | |
|---|---|---|---|
| 5,730,127 A | 3/1998 | Avitall | |
| 5,730,704 A | 3/1998 | Avitall | |
| 5,733,315 A | 3/1998 | Burdette et al. | |
| 5,735,280 A | 4/1998 | Sherman et al. | |
| 5,735,811 A | 4/1998 | Brisken | |
| 5,735,846 A | 4/1998 | Panescu et al. | |
| 5,741,249 A | 4/1998 | Moss et al. | |
| 5,741,320 A | 4/1998 | Thornton et al. | |
| 5,743,870 A | 4/1998 | Edwards | |
| 5,743,903 A | 4/1998 | Stern et al. | |
| 5,749,880 A | 5/1998 | Banas et al. | |
| 5,755,663 A | 5/1998 | Larsen et al. | |
| 5,755,664 A | 5/1998 | Rubenstein | |
| 5,755,715 A | 5/1998 | Stern et al. | |
| 5,755,760 A | 5/1998 | Maguire et al. | |
| 5,769,846 A | 6/1998 | Edwards | |
| 5,782,239 A | 7/1998 | Webster, Jr. | |
| RE35,880 E | 8/1998 | Waldman et al. | |
| 5,797,842 A | 8/1998 | Pumares et al. | |
| 5,797,877 A | 8/1998 | Hamilton et al. | |
| 5,797,903 A | 8/1998 | Swanson et al. | |
| 5,797,905 A | 8/1998 | Fleischman et al. | |
| 5,800,378 A | 9/1998 | Edwards et al. | |
| 5,800,379 A | 9/1998 | Edwards | |
| 5,800,413 A | 9/1998 | Swartz et al. | |
| 5,800,428 A | 9/1998 | Nelson et al. | |
| 5,800,429 A | 9/1998 | Edwards | |
| 5,807,249 A | 9/1998 | Qin et al. | |
| 5,807,308 A | 9/1998 | Edwards | |
| 5,807,391 A | 9/1998 | Wijkamp | |
| 5,807,395 A | 9/1998 | Mulier et al. | |
| 5,824,046 A | 10/1998 | Smith et al. | |
| 5,846,218 A | 12/1998 | Brisken | |
| 5,851,232 A | 12/1998 | Lois | |
| 5,928,279 A | 7/1999 | Shannon et al. | |
| 5,938,660 A | 8/1999 | Swartz | |
| 5,971,983 A | 10/1999 | Lesh | |
| 6,006,755 A * | 12/1999 | Edwards | 128/898 |
| 6,012,457 A | 1/2000 | Lesh | |
| 6,023,638 A | 2/2000 | Swanson | |
| 6,024,739 A | 2/2000 | Ponzi | |
| 6,024,740 A | 2/2000 | Lesh | |
| 6,064,902 A | 5/2000 | Haissaguerre et al. | |
| 6,071,279 A | 6/2000 | Whayne et al. | |
| 6,071,281 A | 6/2000 | Burnside et al. | |
| 6,117,101 A | 9/2000 | Diederich | |
| 6,152,920 A | 11/2000 | Thompson | |
| 6,161,543 A | 12/2000 | Cox et al. | |
| 6,176,842 B1 | 1/2001 | Tachibana et al. | |
| 6,210,356 B1 | 4/2001 | Anderson et al. | |
| 6,214,002 B1 | 4/2001 | Fleischman et al. | |
| 6,237,605 B1 | 5/2001 | Vaska et al. | |
| 6,238,389 B1 * | 5/2001 | Paddock et al. | 600/146 |
| 6,305,378 B1 | 10/2001 | Lesh | |
| 6,383,151 B1 * | 5/2002 | Diederich et al. | 601/2 |
| 6,468,272 B1 * | 10/2002 | Koblish et al. | 606/41 |

FOREIGN PATENT DOCUMENTS

| | | |
|---|---|---|
| WO | WO 94/00050 A1 | 1/1994 |
| WO | WO 94/21165 | 9/1994 |
| WO | WO 94/21167 A1 | 9/1994 |
| WO | WO 94/21168 A1 | 9/1994 |
| WO | WO 95/10318 A1 | 4/1995 |
| WO | WO 95/10319 A1 | 4/1995 |
| WO | WO 95/10321 A1 | 4/1995 |
| WO | WO 0515115 | 6/1995 |
| WO | WO 95/19738 A1 | 7/1995 |
| WO | WO 96/00036 A1 | 1/1996 |
| WO | WO 96/10961 | 4/1996 |
| WO | WO 96/26675 | 9/1996 |
| WO | WO 96/32885 A1 | 10/1996 |
| WO | WO 96/32897 | 10/1996 |
| WO | WO 97/32525 | 9/1997 |
| WO | WO 97/37607 | 10/1997 |
| WO | WO 97/45156 A1 | 12/1997 |
| WO | WO 98/02201 | 1/1998 |
| WO | WO 98/26724 A1 | 6/1998 |
| WO | WO 98/49957 | 11/1998 |
| WO | WO 99/00064 | 1/1999 |
| WO | WO 99/00064 A1 | 1/1999 |
| WO | WO 99/02096 | 1/1999 |
| WO | WO 00/07508 | 2/2000 |

OTHER PUBLICATIONS

Diederich, et al., The Development of Intracavitary Ultrasonic Applicators for Hyperthermia: A Design and Experimental Study. Medical Physics, Jul./Aug. 1990.

Jais et al., "Biatrial Dimensions Relevant to Catheter Ablation," NASPE 17$^{th}$ Annual Scientific Sessions Abstract, Dec. 1995.

Avitall et al., "Physics and Engineering Transcatheter Tissue Ablation", Journal of American College of Cardiology, 22(3):921–932 (1993).

Cox, JL et al., "The Surgical Treatment of Atrial Fibrillation. I. Summary", Thoracic and Cariovascular Surgery 101(3), pp. 402–405 (1991).

Cox, JL, "Surgical Treatment of Atrial Fibrillation. IV. Surgical Technique, Thoracic and Cardiovascular Surgery" 101(4), pp. 584,592 (1991).

Fram et al., "Feasibility of RF Powered Thermal Balloon Ablation of Atrioventricular Bypass Tracts via the Coronary Sinus: In vivo Canine Studies", PACE, 18:1518–1530 (1995).

Haissaguerre et al., "Right and Left Atrial Radiofrequency Catheter Therapy of Paroxysmal Atrial Fibrillation", Journal of Cardiovascular Electrophysiology 7(12):1132–1144 (1996).

Hindricks, et al, Current Management of Arrhythmias (1991).

Jais et al., "A Focal Source of Atrial Fibrillation Treated by Discrete Radiofrequency Ablation", Circulation, 95:572–576 (1997).

McMath LP et al., "Percutaneous Laser Balloon Coagulation of Accessory Pathways", Diagn Ther Cardiovasc Interven 1425:165–171 (1991).

Schuger CD et al., "Long–term Effects of Percutaneous Laser Balloon Ablation from the Canine Coronary Sinus", Circulation 86:947–954 (1992).

Sueda et al., "Simple Left Atrial Procedure for Chronic Atrial Fibrillation Associated With Mitral Valve Disease" (1996).

* cited by examiner

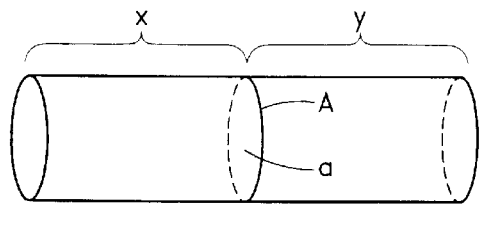
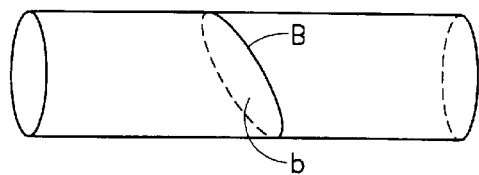
FIG. 1A    FIG. 1B
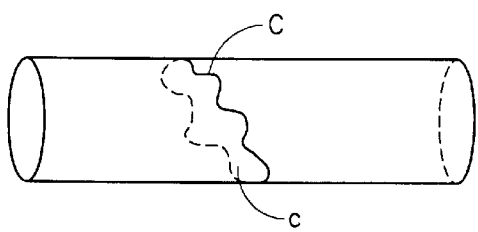
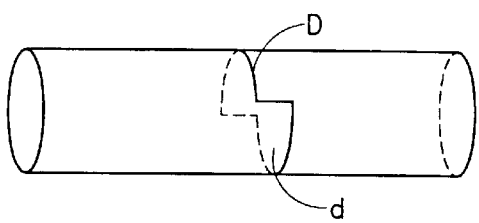
FIG. 1C    FIG. 1D
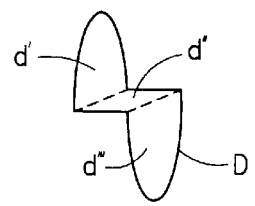
FIG. 1E

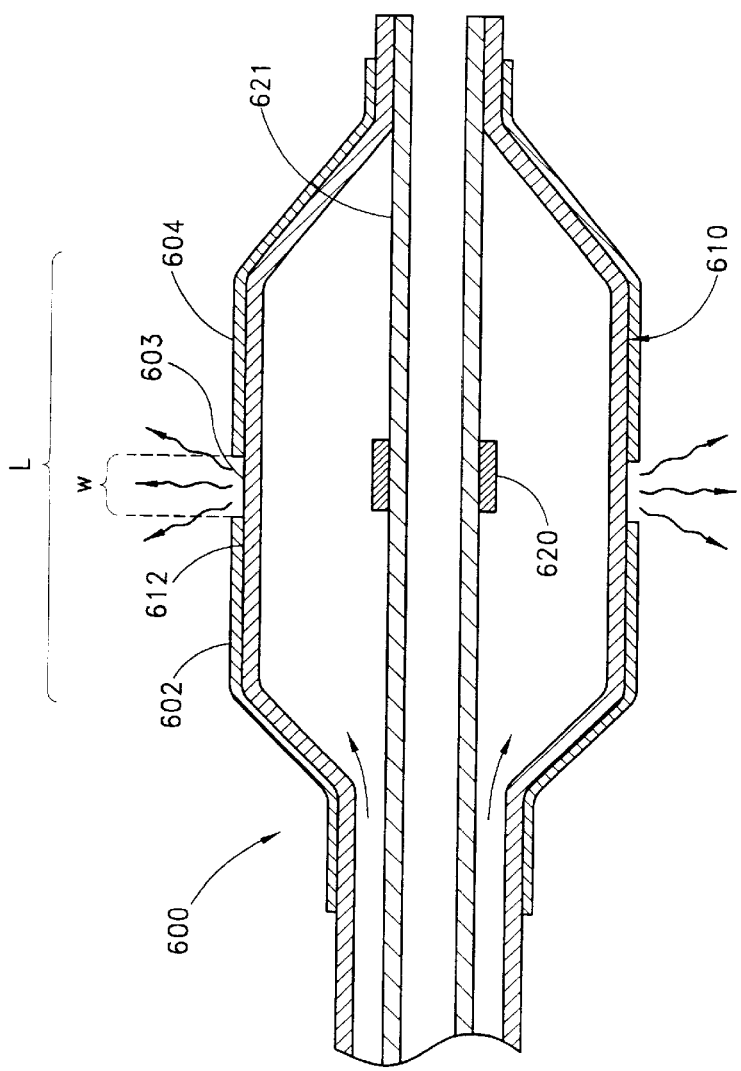
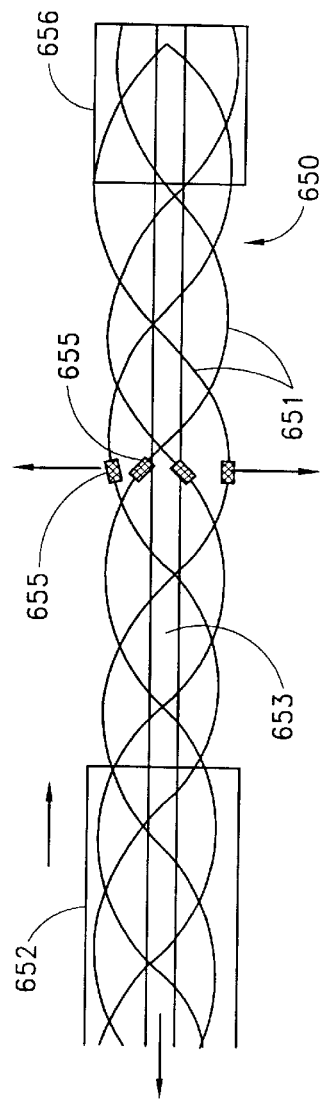
FIG. 27A
FIG. 27B

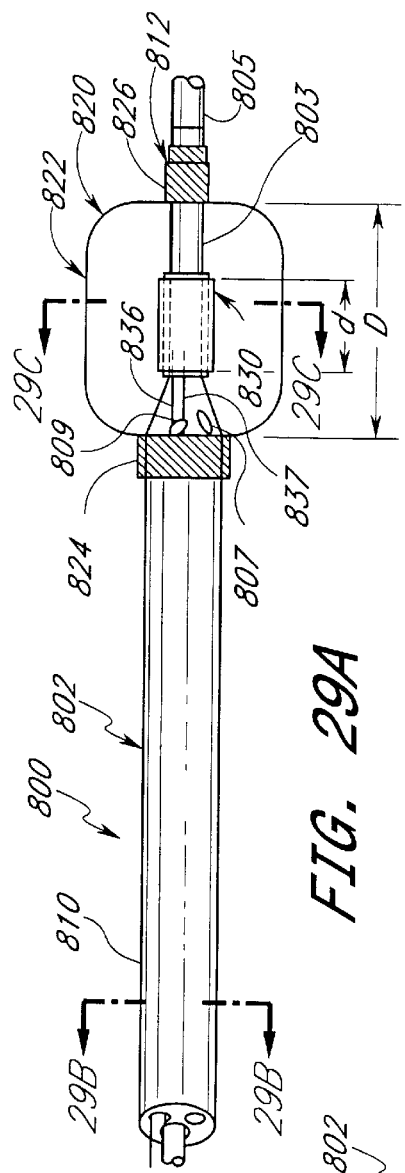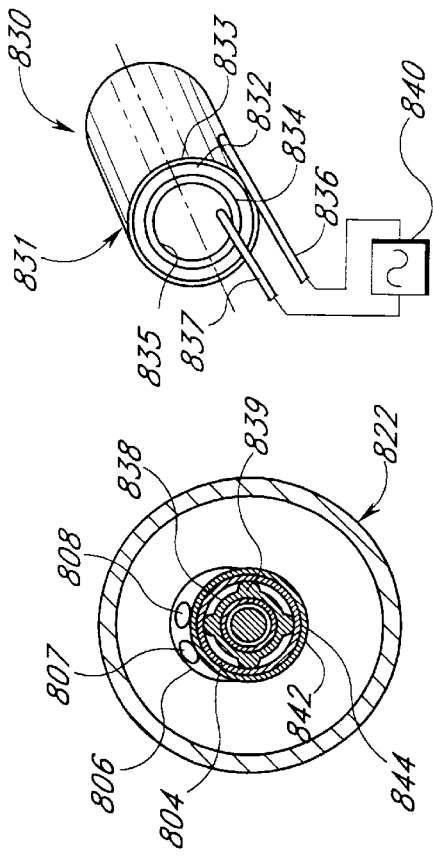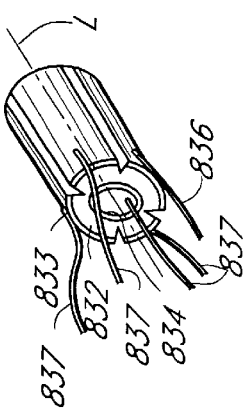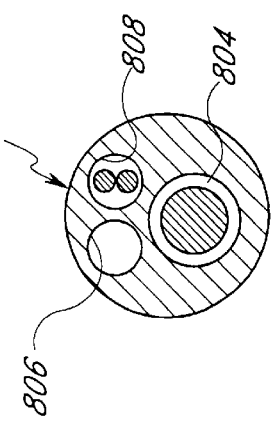

SURGICAL ABLATION PROBE FOR FORMING A CIRCUMFERENTIAL LESION

RELATED APPLICATIONS

The present application also claims priority under 35 U.S.C. §119(e) to U.S. Provisional Application No. 60/212,879, filed Jun. 13, 2000.

TECHNICAL FIELD

The field of the invention relates to a surgical device and method. More particularly, it relates to a tissue ablation probe and method for ablating a circumferential region of tissue at a location where a pulmonary vein extends from an atrium. The probe has particular utility during invasive or minimally invasive cardiac surgery.

BACKGROUND OF THE INVENTION

Many local energy delivery devices and methods have been developed for the treatment of various abnormal tissue conditions in the body, and particularly for treating abnormal tissue along body space walls which define various body spaces in the body. For example, various devices have been disclosed with the primary purpose of treating or recanalizing atherosclerotic vessels with localized energy delivery. Several prior devices and methods combine energy delivery assemblies in combination with cardiovascular stent devices in order to locally deliver energy to tissue in order to maintain patency in diseased lumens such as blood vessels. Endometriosis, another abnormal wall tissue condition which is associated with the endometrial cavity and is characterized by dangerously proliferative uterine wall tissue along the surface of the endometrial cavity, has also been treated by local energy delivery devices and methods.

Several other devices and methods have also been disclosed which use catheter-based heat sources for the intended purpose of inducing thrombosis and controlling hemorrhaging within certain body lumens such as vessels. Detailed examples of local energy delivery devices and related procedures such as those of the types described above are disclosed in the following references: U.S. Pat. No. 4,672,962 to Hershenson; U.S. Pat. No. 4,676,258 to InoKuchi et al.; U.S. Pat. No. 4,790,311 to Ruiz; U.S. Pat. No. 4,807,620 to Strul et al.; U.S. Pat. No. 4,998,933 to Eggers et al.; U.S. Pat. No. 5,035,694 to Kasprzyk et al.; U.S. Pat. No. 5,190,540 to Lee; U.S. Pat. No. 5,226,430 to Spears et al.; and U.S. Pat. No. 5,292,321 to Lee; U.S. Pat. No. 5,449,380 to Chin; U.S. Pat. No. 5,505,730 to Edwards; U.S. Pat. No. 5,558,672 to Edwards et al.; and U.S. Pat. No. 5,562,720 to Stem et al.; U.S. Pat. No. 4,449,528 to Auth et al.; U.S. Pat. No. 4,522,205 to Taylor et al.; and U.S. Pat. No. 4,662,368 to Hussein et al.; U.S. Pat. No. 5,078,736 to Behl; and U.S. Pat. No. 5,178,618 to Kandarpa.

Other prior devices and methods electrically couple fluid to an ablation element during local energy delivery for treatment of abnormal tissues. Some such devices couple the fluid to the ablation element for the primary purpose of controlling the temperature of the element during the energy delivery. Other such devices couple the fluid more directly to the tissue-device interface either as another temperature control mechanism or in certain other known applications as a carrier or medium for the localized energy delivery. Detailed examples of ablation devices which use fluid to assist in electrically coupling electrodes to tissue are disclosed in the following references: U.S. Pat. No. 5,348,554 to Imran et al.; U.S. Pat. No. 5,423,811 to Imran et al.; U.S. Pat. No. 5,505,730 to Edwards; U.S. Pat. No. 5,545,161 to Imran et al.; U.S. Pat. No. 5,558,672 to Edwards et al.; U.S. Pat. No. 5,569,241 to Edwards; U.S. Pat. No. 5,575,788 to Baker et al.; U.S. Pat. No. 5,658,278 to Imran et al.; U.S. Pat. No. 5,688,267 to Panescu et al.; U.S. Pat. No. 5,697,927 to Imran et al.; U.S. Pat. No. 5,722,403 to McGee et al.; U.S. Pat. No. 5,769,846; and PCT Patent Application Publication No. WO 97/32525 to Pomeranz et al.; and PCT Patent Application Publication No. WO 98/02201 to Pomeranz et al.

Other prior devices and methods have been disclosed which use a probe as a surgical device, thereby allowing the physician to directly apply an electrode to tissue. Detailed examples of surgical probes are disclosed in the following references: U.S. Pat. No. 6,023,638 to Swanson; U.S. Pat. No. 4,841,979 to Dow et al.; U.S. Pat. No. 4,917,096 to Englehart et al.; and U.S. Pat. No. 6,152,920 to Thompson et al.

Atrial Fibrillation

Cardiac arrhythmias, and atrial fibrillation in particular, persist as common and dangerous medical ailments associated with abnormal cardiac chamber wall tissue. In patients with cardiac arrhythmia, abnormal regions of cardiac tissue do not follow the synchronous beating cycle associated with normally conductive tissue in patients with sinus rhythm. Instead, the abnormal regions of cardiac tissue aberrantly conduct electrical signals to adjacent tissue, thereby disrupting the cardiac cycle and causing an asynchronous cardiac rhythm. Such abnormal conduction is known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet reentrant type, characterized by multiple asynchronous loops of electrical impulses that are scattered about the atrial chamber and are often self propagating. In the alternative or in addition to the multiwavelet reentrant type, cardiac arrhythmias may also have a focal origin, such as when an isolated region of tissue in an atrium fires autonomously in a rapid, repetitive fashion. Cardiac arrhythmias, including atrial fibrillation, may be generally detected using the global technique of an electrocardiogram (EKG). More sensitive procedures of mapping the specific conduction along the cardiac chambers have also been disclosed, such as, for example, in U.S. Pat. No. 4,641,649 to Walinsky et al. and in PCT Patent Application Publication No. WO 96/32897 to Desai.

A host of clinical conditions can result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle which thereafter pumps the embolism into the cerebral circulation where a stroke results. Accordingly, numerous procedures for treating atrial arrhythmias have been developed, including pharmacological, surgical, and catheter ablation procedures.

Several pharmacological approaches intended to remedy or otherwise treat atrial arrhythmias have been disclosed, such as, for example, those approaches disclosed in the following references: U.S. Pat. No. 4,673,563 to Beme et al.; U.S. Pat. No. 4,569,801 to Molloy et al.; and "Current Management of Arrhythmias" (1991) by Hindricks, et al. Such pharmacological solutions, however, are not generally believed to be entirely effective in many cases, and are even believed in some cases to result in proarrhythmia and long term inefficacy.

Several surgical approaches have also been developed with the intention of treating atrial fibrillation. One particular example is known as the "maze procedure," as is disclosed by Cox, J. L. et al. in "The surgical treatment of atrial fibrillation. I. Summary" *Thoracic and Cardiovascular Surgery* 101(3), pp. 402–405 (1991); and also by Cox, J L in "The surgical treatment of atrial fibrillation. IV. Surgical Technique", *Thoracic and Cardiovascular Surgery* 101(4), pp. 584–592 (1991). In general, the "maze" procedure is designed to relieve atrial arrhythmia by restoring effective atrial systole and sinus node control through a prescribed pattern of incisions about the tissue wall. In the early clinical experiences reported, the "maze" procedure included surgical incisions in both the right and the left atrial chambers. However, more recent reports predict that the surgical "maze" procedure may be substantially efficacious when performed only in the left atrium. See Sueda et al., "Simple Left Atrial Procedure for Chronic Atrial Fibrillation Associated With Mitral Valve Disease" (1996).

The "maze procedure" as performed in the left atrium generally includes forming vertical incisions from the two superior pulmonary veins and terminating in the region of the mitral valve annulus, traversing the region of the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the arrhythmogenic conduction from the boxed region of the pulmonary veins to the rest of the atrium by creating conduction blocks within the aberrant electrical conduction pathways. Other variations or modifications of this specific pattern just described have also been disclosed, all sharing the primary purpose of isolating known or suspected regions of arrhythmogenic origin or propagation along the atrial wall.

While the "maze" procedure and its variations as reported by Dr. Cox and others have met some success in treating patients with atrial arrhythmia, its highly invasive methodology is believed to be prohibitive in most cases. However, these procedures have provided a guiding principle that electrically isolating faulty cardiac tissue may successfully prevent atrial arrhythmia, and particularly atrial fibrillation caused by arrhythmogenic conduction arising from the region of the pulmonary veins.

Less invasive catheter-based approaches to treat atrial fibrillation have been disclosed which implement cardiac tissue ablation for terminating arrhythmogenic conduction in the atria. Examples of such catheter-based devices and treatment methods have generally targeted atrial segmentation with ablation catheter devices and methods adapted to form linear or curvilinear lesions in the wall tissue which defines the atrial chambers. Some specifically disclosed approaches provide specific ablation elements which are linear over a defined length intended to engage the tissue for creating the linear lesion. Other disclosed approaches provide shaped or steerable guiding sheaths, or sheaths within sheaths, for the intended purpose of directing tip ablation catheters toward the posterior left atrial wall such that sequential ablations along the predetermined path of tissue may create the desired lesion. In addition, various energy delivery modalities have been disclosed for forming atrial wall lesions, and include the use of microwave, laser, ultrasound, thermal conduction, and more commonly, radio frequency energies to create conduction blocks along the cardiac tissue wall.

Detailed examples of ablation device assemblies and methods for creating lesions along an atrial wall are disclosed in the following U.S. Patent references: U.S. Pat. No. 4,898,591 to Jang et al.; U.S. Pat. No. 5,104,393 to Isner et al.; U.S. Pat. No. 5,427,119; U.S. Pat. No. 5,487,385 to Avitall; U.S. Pat. No. 5,497,119 to Swartz et al.; U.S. Pat. No. 5,545,193 to Fleischman et al.; U.S. Pat. No. 5,549,661 to Kordis et al.; U.S. Pat. No. 5,575,810 to Swanson et al.; U.S. Pat. No. 5,564,440 to Swartz et al.; U.S. Pat. No. 5,592,609 to Swanson et al.; U.S. Pat. No. 5,575,766 to Swartz et al.; U.S. Pat. No. 5,582,609 to Swanson; U.S. Pat. No. 5,617,854 to Munsif; U.S. Pat. No. 5,687,723 to Avitall; U.S. Pat. No. 5,702,438 to Avitall. Other examples of such ablation devices and methods are disclosed in the following PCT Patent Application Publication Nos.: WO 93/20767 to Stem et al.; WO 94/21165 to Kordis et al.; WO 96/10961 to Fleischman et al.; WO 96/26675 to Klein et al.; and WO 97/37607 to Schaer. Additional examples of such ablation devices and methods are disclosed in the following published articles: "Physics and Engineering of Transcatheter Tissue Ablation", Avitall et al., *Journal of American College of Cardiology*, Volume 22, No. 3:921–932 (1993); and "Right and Left Atrial Radiofrequency Catheter Therapy of Paroxysmal Atrial Fibrillation," Haissaguerre, et al., *Journal of Cardiovascular Electrophysiology* 7(12), pp. 1132–1144 (1996).

In addition to the known assemblies summarized above, additional tissue ablation device assemblies have been recently developed for the specific purpose of ensuring firm contact and consistent positioning of a linear ablation element along a length of tissue. This is accomplished by anchoring the element at least at one predetermined location along that length, such as in order to form a "maze"-type lesion pattern in the left atrium. An example of such an assembly is disclosed in U.S. Pat. No. 5,971,983 to Lesh, issued Oct. 26, 1999, which is hereby incorporated by reference. The assembly includes an anchor at each of two ends of a linear ablation element in order to secure those ends to each of two predetermined locations along a left atrial wall, such as at two adjacent pulmonary veins, so that tissue may be ablated along the length of tissue extending therebetween.

In addition to attempting atrial wall segmentation with long linear lesions for treating atrial arrhythmia, other ablation devices and methods have also been disclosed which are intended to use expandable members such as balloons to ablate cardiac tissue. Some such devices have been disclosed primarily for use in ablating tissue wall regions along the cardiac chambers. Other devices and methods have been disclosed for treating abnormal conduction of the left-sided accessory pathways, and in particular associated with "Wolff-Parkinson-White" syndrome—various such disclosures use a balloon for ablating from within a region of an associated coronary sinus adjacent to the desired cardiac tissue to ablate. Further more detailed examples of devices and methods such as of the types just described are variously disclosed in the following published references: Fram et al., in "Feasibility of RF Powered Thermal Balloon Ablation of Atrioventricular Bypass Tracts via the Coronary Sinus: In vivo Canine Studies," *PACE*, Vol. 18, p 1518–1530 (1995); "Long-term effects of percutaneous laser balloon ablation from the canine coronary sinus", Schuger CD et al., *Circulation* (1992) 86:947–954; and "Percutaneous laser balloon coagulation of accessory pathways", McMath L P et al., Diagn Ther Cardiovasc Interven 1991; 1425:165–171.

Arrhythmias Originating from Foci in Pulmonary Veins

As briefly discussed above, various modes of atrial fibrillation have been observed to be focal in nature, caused by the rapid and repetitive firing of an isolated center within cardiac muscle tissue associated with the atrium. Such foci may act as either a trigger of atrial fibrillatory paroxysmal or may even sustain the fibrillation. Various disclosures have suggested that focal atrial arrhythmia often originates from at least one tissue region along one or more of the pulmonary veins of the left atrium, and even more particularly in the superior pulmonary veins.

Less invasive percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to terminate the arrhythmogenic conduction.

One example of a focal ablation method intended to treat focal arrhythmia originating from a pulmonary vein is disclosed by Haissaguerre, et al. in "Right and Left Atrial Radiofrequency Catheter Therapy of Paroxysmal Atrial Fibrillation" in *Journal of Cardiovascular Electrophysiology* 7(12), pp. 1132–1144 (1996). Haissaguerre, et al. discloses radio frequency catheter ablation of drug-refractory paroxysmal atrial fibrillation using linear atrial lesions complemented by focal ablation targeted at arrhythmogenic foci in a screened patient population. The site of the arrhythmogenic foci were generally located just inside the superior pulmonary vein, and the focal ablations were generally performed using a standard 4 mm tip single ablation electrode.

Another focal ablation method of treating atrial arrhythmias is disclosed in Jais et al., "A focal source of atrial fibrillation treated by discrete radio frequency ablation," *Circulation* 95:572–576 (1997). Jais et al. discloses treating patients with paroxysmal arrhythmias originating from a focal source by ablating that source. At the site of arrhythmogenic tissue, in both right and left atria, several pulses of a discrete source of radio frequency energy were applied in order to eliminate the fibrillatory process.

Other assemblies and methods have been disclosed addressing focal sources of arrhythmia in pulmonary veins by ablating circumferential regions of tissue either along the pulmonary vein, at the ostium of the vein along the atrial wall, or encircling the ostium and along the atrial wall. More detailed examples of device assemblies and methods for treating focal arrhythmia as just described are disclosed in PCT Patent Application Publication No. WO 99/02096 to Diederich et al., and also in the following Patents and pending U.S. Patent Applications: U.S. Ser. No. 08/889,798 for "Circumferential Ablation Device Assembly" to Lesh et al., filed Jul. 8, 1997, now U.S. Pat. No. 6,024,740, issued on Feb. 15, 2000; U.S. Ser. No. 08/889,835 for "Device and Method for Forming a Circumferential Conduction Block in a Pulmonary Vein" to Lesh, filed Jul. 8, 1997, now U.S. Pat. No. 6,012,457, issued Jan. 11, 2000; U.S. Ser. No. 09/199, 736 for "Circumferential Ablation Device Assembly" to Diederich et al., filed Feb. 3, 1998, now U.S. Pat. No. 6,117,101, issued Sep. 12, 2000; and U.S. Ser. No. 09/260, 316 for "Tissue Ablation Device Assembly and Method of Forming a Conduction Block Along a Length of Tissue" to Langberg et al., filed Mar. 1, 1999.

Another specific device assembly and method which is intended to treat focal atrial fibrillation by ablating a circumferential region of tissue between two seals in order to form a conduction block to isolate an arrhythmogenic focus within a pulmonary vein is disclosed in U.S. Pat. No. 5,938,660 and a related PCT Patent Application Publication No. WO 99/00064. The disclosures of these references are herein incorporated in their entirety by reference thereto.

The device assemblies and methods disclosed heretofore for ablating a circumferential region of tissue generally involve catheter-based therapies wherein an ablation element is mounted on the distal end of the catheter for placement in a pulmonary vein, such as in a percutaneous translumenal procedure. However, in certain surgical approaches, such as trans-thoracic surgery, a physician can access the pulmonary vein in a more direct manner, such as through an atriotomy, thereby obviating the need for a catheter-based device. None of the disclosed circumferential ablation devices provides a device assembly or method that can be used to directly place an ablation element in a pulmonary vein during trans-thoracic or minimally invasive cardiac surgical procedures.

Thus, a need exists for a rigid, handheld surgical probe for delivering ablative energy at a location where a pulmonary vein extends from an atrial wall. It is desirable that such a surgical probe be adapted to precisely deliver ablative energy to form a circumferential lesion to treat atrial fibrillation.

SUMMARY OF THE INVENTION

The preferred embodiments of the present invention provide a ergonomically designed, handheld surgical ablation probe that is substantially rigid and can be used to directly apply ablative energy to form a circumferential lesion in a pulmonary vein during trans-thoracic or minimally invasive surgery. The preferred embodiments are provided with a deflectable tip for enhanced maneuverability and precise placement of the ablation element in a pulmonary vein. The preferred embodiments also include an expandable member on the distal end for anchoring the ablation element to the surrounding tissue during ablation. The surgical ablation probe is adapted for use with various types of ablation elements, such as, for example, an ultrasonic transducer.

One aspect of the present invention involves a medical device system for ablating a circumferential region of tissue in order to form a circumferential conduction block at a location where a pulmonary vein extends from an atrium in a patient's heart. Such conduction block may be formed in order to, for example: electrically isolate a focal source of arrhythmia in the pulmonary vein from the rest of the atrium; or connect linear lesions such that a pattern of conduction blocks may be formed to isolate a posterior region of the atrial wall from the rest of the atrium.

In one mode, a tissue ablation probe of the present medical device system ablates a substantial portion of a circumferential region of tissue at a location in a patient's body where a pulmonary vein extends from an atrium in a patient. The ablation probe includes a handle attached to a proximal end portion of a relatively short shaft (i.e., short as compared to a percutaneous translumenal catheter). An ablation member is coupled to a distal end portion of the shaft. The ablation member also comprises an expandable member coupled to the distal end portion of the shaft, wherein the expandable member is adjustable from a collapsed position to an expanded position. The expandable member is adapted to engage a substantial portion of the circumferential region of tissue when in the expanded position. The ablation member also has an ablation element that is adapted to ablate at least a portion of the substantial portion of the circumferential region of tissue.

The ablation element employed in differing modes of the tissue ablation probe can comprise a microwave ablation element, a cryogenic ablation element, a thermal ablation element, a light-emitting ablation element (e.g., laser), an ultrasound transducer, or an electrical ablation element, such as an RF ablation element.

In one mode of the ablation apparatus, the expandable member is an inflatable balloon. The expandable member can have an outer surface that is adapted to contact the substantial portion of the circumferential region of tissue along an ablative path when the expandable member is adjusted to the expanded position.

The ablation member may also include a sensor that is coupled to the expandable member at a location at least when the expandable member is in the expanded position. A conductor is coupled to the sensor in a manner that does not substantially affect the adjustment of the expandable member from the collapsed positioned to an expanded position. In a preferred form, the conductor also is coupled to a coupler at the proximal end portion of the handle.

In a preferred mode, the ablation element preferably comprises an ultrasound transducer adapted to emit a circumferential path of ultrasound ablative energy. The sensor may be positionable within the circumferential path when the expandable member is in the expanded position.

In accordance with one method of using the ablation probe of the present invention, during a trans-thoracic (open heart) or minimally invasive cardiac procedure, e.g., for mitral valve replacement, a physician can place the distal end of the shaft, including the ablation member, at a location where a pulmonary vein extends from an atrium. The expandable member is expanded to secure and/or ablatively couple the ablation member to the location and the ablation element is energized to ablate at least a substantial portion of the circumferential region of tissue.

Also disclosed is a method for monitoring the ablation of a substantial portion of a circumferential region of tissue at a location where a pulmonary vein extends from an atrium. The method involves positioning an ablation member, which has an ablation element, along the location where the pulmonary vein extends from the atrium. The ablation element is activated to ablate the substantial portion of the circumferential region of tissue. This can be done simultaneously or through a sequential series of ablation steps (temporal and/or spatial). Temperature is monitored along the substantial portion of the circumferential region of tissue. The ablation element is deactivated when the temperature along the substantial portion of the circumferential region of tissue has reached either a first predetermined value or a second predetermined valve for a predetermined period of time.

While various aspects and features of the present invention have particular utility in the context of tissue ablation apparatuses and ablation processes, such aspects and features also can be practiced apart from such devices and methods.

Various aspects, features and advantages of the present invention, in addition to those described above, will also become apparent from the following description of preferred modes of the invention and from the appended description.

BRIEF DESCRIPTION OF THE DRAWINGS

The advantages and features of the disclosed invention will readily be appreciated by persons skilled in the art from the following detailed description when read in conjunction with the drawings listed below.

FIG. 1 shows schematic, perspective views of various exemplary circumferential conduction blocks formed in pulmonary vein wall tissue with a circumferential ablation device assembly.

FIG. 27A shows a cross-sectional view of another circumferential ablation member for use in a circumferential ablation device assembly for pulmonary vein isolation, wherein the circumferential ablation element circumscribes an outer surface of an expandable member substantially along its working length and is insulated at both the proximal and the distal ends of the working length to thereby form an uninsulated equatorial band in a middle region of the working length or otherwise circumferential region of the working length which is bounded both proximally and distally by end portions of the working length, wherein the member is adapted to ablate a circumferential path of tissue engaged by the equatorial band.

FIG. 27B shows a perspective view of another circumferential ablation member which is adapted for use in a circumferential ablation device assembly for pulmonary vein isolation, wherein the expandable member is shown to be a cage of coordinating wires which are adapted to be adjusted from a radially collapsed position to a radially expanded position in order to engage electrode elements on the wires about a circumferential pattern of tissue to be ablated.

FIG. 29A shows a longitudinal cross-sectional view of another circumferential ablation probe, and shows the ablation element to include a single cylindrical ultrasound transducer which is positioned along an inner member within an expandable balloon which is further shown in a radially expanded condition.

FIG. 29B shows a transverse cross-sectional view of the circumferential ablation probe shown in FIG. 29A taken along line 29B—29B.

FIG. 29C shows a transverse cross-sectional view of the circumferential ablation probe shown in FIG. 29A taken along line 29C—29C.

FIG. 29D shows a perspective view of the ultrasonic transducer of FIG. 29A in isolation.

FIG. 29E shows a modified version of the ultrasonic transducer of FIG. 29D with individually driven sectors.

Figure 2:
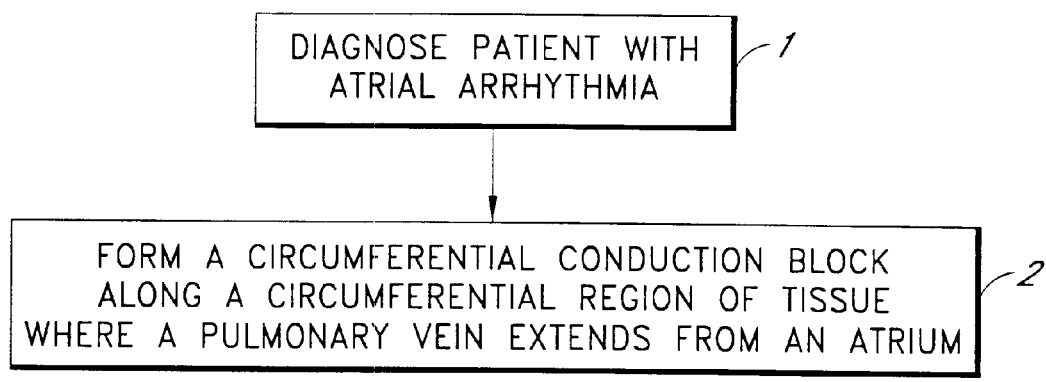
FIG. 2 diagrammatically shows the sequential, general steps for treating atrial arrhythmia.

Further aspects, features and advantages of this invention will become apparent from the detailed description of the modes of the invention which follows.

DETAILED DESCRIPTION OF THE PREFERRED EMBODIMENT

As will be described with reference to the detailed embodiments below, the invention is well adapted to treat patients with atrial arrhythmia by ablating a circumferential region of tissue at a location where a pulmonary vein extends from an atrium, such as (a) where cardiac tissue extends up from the vein; or (b) along the vein's ostium along the atrial wall; or (c) along the atrial wall and surrounding the vein's ostium. By ablating such a circumferential region of tissue, a circumferential conduction block is formed which either isolates the atrium from an arrhythmogenic focus upstream of the conduction block relative to the vein, or ablates the focus.

For the purpose of further illustration, particular embodiments for pulmonary vein isolation are shown and described by reference to FIGS. 1–18, with the related method of treatment broadly illustrated diagrammatically in the flow diagram of FIG. 2. The details of the circumferential ablation probe of the present invention are described by reference to FIGS. 19–32B.

Definition of Terms

The following terms will have the following meanings throughout this specification.

The terms "body space," including derivatives thereof, is herein intended to mean any cavity or lumen within the body which is defined at least in part by a tissue wall. For example, the cardiac chambers, the uterus, the regions of the gastrointestinal tract, and the arterial or venous vessels are all considered illustrative examples of body spaces within the intended meaning.

The term "body lumen," including derivatives thereof, is herein intended to mean any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of lumens within the intended meaning. Blood vessels are also herein considered lumens, including regions of the vascular tree between their branch points. More particularly, the pulmonary veins are lumens within the intended meaning, including the region of the pulmonary veins between the branched portions of their ostia along a left ventricle wall, although the wall tissue defining the ostia typically presents uniquely tapered lumenal shapes.

The terms "circumference" or "circumferential", including derivatives thereof, as used herein include a continuous path or line which forms an outer border or perimeter that surrounds and thereby defines an enclosed region of space. Such a continuous path starts at one location along the outer border or perimeter, and translates along the outer border or perimeter until it is completed at the original starting location to enclose the defined region of space. The related term "circumscribe," including derivatives thereof, as used herein includes a surface to enclose, surround, or encompass a defined region of space. Therefore, a continuous line which is traced around a region of space and which starts and ends at substantially the same location "circumscribes" the region of space and has a "circumference" which includes the distance the line travels as it translates along the path circumscribing the space.

Still further, a circumferential path or element may include one or more of several shapes, and may be for example circular, oblong, ovular, elliptical, or otherwise planar enclosures. A circumferential path may also be three dimensional, such as for example two opposite-facing semi-circular paths in two different parallel or off-axis planes that are connected at their ends by line segments bridging between the planes.

A "circumferential conduction block" according to the present invention is formed along a region of tissue that follows a circumferential path along the pulmonary vein wall, circumscribing the pulmonary vein lumen and transecting the pulmonary vein relative to electrical conduction along its longitudinal axis. The transecting circumferential conduction block therefore isolates electrical conduction between opposite longitudinal portions of the pulmonary wall relative to the conduction block and along the longitudinal axis.

For purpose of further illustration, FIGS. 1A–D therefore show various circumferential paths A, B, C, and D, respectively, each translating along a portion of a pulmonary vein wall and circumscribing a defined region of space, shown at a, b, c, and d also respectively, each circumscribed region of space being a portion of a pulmonary vein lumen. For still further illustration of the three-dimensional circumferential case shown in FIG. 1D, FIG. 1E shows an exploded perspective view of circumferential path D as it circumscribes multiplanar portions of the pulmonary vein lumen shown at d', d", and d'", which together make up region d as shown in FIG. 1D.

The term "transect", including derivatives thereof, is also herein intended to mean to divide or separate a region of space into isolated regions. Thus, each of the regions circumscribed by the circumferential paths shown in FIGS. 1A–D transects the respective pulmonary vein, including its lumen and its wall, to the extent that the respective pulmonary vein is divided into a first longitudinal region located on one side of the transecting region, shown, for example, at region "X" in FIG. 1A, and a second longitudinal region on the other side of the transecting plane, shown, for example, at region "Y" also in FIG. 1A.

The terms "ablate" or "ablation," including derivatives thereof, are hereafter intended to include the substantial altering of the mechanical, electrical, chemical, or other structural nature of tissue. In the context of ablation applications shown and described with reference to the variations of the illustrative device below, "ablation" is intended to include sufficient altering of tissue properties to substantially block conduction of electrical signals from or through the ablated cardiac tissue.

The term "element" within the context of "ablation element" is herein intended to include a discrete element, such as an electrode, or a plurality of discrete elements, such as a plurality of spaced electrodes, which are positioned so as to collectively ablate a region of tissue.

Therefore, an "ablation element" according to the defined terms can include a variety of specific structures adapted to ablate a defined region of tissue. For example, one suitable ablation element for use in the present invention may be formed, according to the teachings of the embodiments below, from an "energy emitting" type of structure which is adapted to emit energy sufficient to ablate tissue when coupled to and energized by an energy source. Suitable "energy emitting" ablation elements for use in the present invention may therefore include, for example: an electrode element adapted to couple to a direct current ("DC") or alternating current ("AC") current source, such as a Radio Frequency ("RF") current source; an antenna element which is energized by a microwave energy source; a heating element, such as a metallic element or other thermal conductor which is energized to emit heat such as by convective or conductive heat transfer, by resistive heating due to current flow, or by optical heating with light; a light emitting element, such as a fiber optic element which transmits light sufficient to ablate tissue when coupled to a light source; or an ultrasonic element such as an ultrasound crystal element which is adapted to emit ultrasonic sound waves sufficient to ablate tissue when coupled to a suitable excitation source.

In addition, other elements for altering the nature of tissue may be suitable as "ablation elements" under the present invention when adapted according to the detailed description of the invention below. For example, a cryogenic ablation (cryoblation) element adapted to sufficiently cool tissue to substantially alter the structure thereof may be suitable if adapted according to the teachings of the current invention. Furthermore, a fluid delivery element, such as a discrete port or a plurality of ports which are fluidly coupled to a fluid delivery source, may be adapted to infuse an ablating fluid, such as a fluid containing alcohol, into the tissue adjacent to the port or ports to substantially alter the nature of that issue.

Formation of a Circumferential Conduction Block

In the context of the illustrative application of use, catheter-based cardiac arrhythmia therapies generally involve introducing an ablation catheter into a cardiac chamber, such as in a percutaneous translumenal procedure, wherein an ablation element on the catheter's distal end portion is positioned at or adjacent to the aberrant conductive tissue. The ablation element is used to ablate the targeted tissue thereby creating a lesion. A further description of such procedure is described in U.S. Pat. No. 6,024,740, issued Feb. 15, 2000, which is hereby incorporated by reference. The present invention is aimed at an ablation device with many of the same characteristics of our previously patented catheter-based systems, however, the present invention is designed for direct placement at the location of pulmonary vein terminus during open heart or minimally invasive cardiac surgical procedures.

Returning to the inventive method as shown in FIG. 2, a patient diagnosed with atrial arrhythmia according to diagnosing step (1) is treated with a circumferential conduction block according to treatment step (2). In one aspect, a patient diagnosed according to diagnosis step (1) with multiple wavelet arrhythmia originating from multiple regions along the atrial wall may also be treated in part by forming the circumferential conduction block according to treatment step (2), although as an adjunct to forming long linear regions of conduction block between adjacent pulmonary vein ostia in a less-invasive "maze"-type catheter ablation procedure. More detail regarding this particular aspect of the inventive method is provided below with reference to FIGS. 12–17.

In another aspect of the method of FIG. 2, a patient diagnosed with focal arrhythmia originating from an arrhythmogenic origin or focus in a pulmonary vein is treated according to this method when the circumferential conduction block is formed along a circumferential path of wall tissue that either includes the arrhythmogenic origin or is between the origin and the left atrium. In the former case, the arrhythmogenic tissue at the origin is destroyed by the conduction block as it is formed through that focus. In the latter case, the arrhythmogenic focus may still conduct abnormally, although such aberrant conduction is prevented from entering and affecting the atrial wall tissue due to the intervening circumferential conduction block.

In still a further aspect of the method shown in FIG. 2, the circumferential conduction block may be formed in one of several ways according to treatment step (2). In one example not shown, the circumferential conduction block may be formed by a surgical incision or other method to mechanically transect the pulmonary vein, followed by suturing the transected vein back together. As the circumferential injury is naturally repaired, such as through a physiologic scarring response common to the "maze" procedure, electrical conduction will generally not be restored across the injury site. In another example not shown, a circumferential conduction block of one or more pulmonary veins may be performed in an epicardial ablation procedure, wherein an ablation element is either placed around the target pulmonary vein or is translated circumferentially around it while being energized to ablate the adjacent tissue in an "outside-in" approach. This alternative method may be performed during an open chest-type procedure, or may be done using other known epicardial access techniques.

Figure 3:
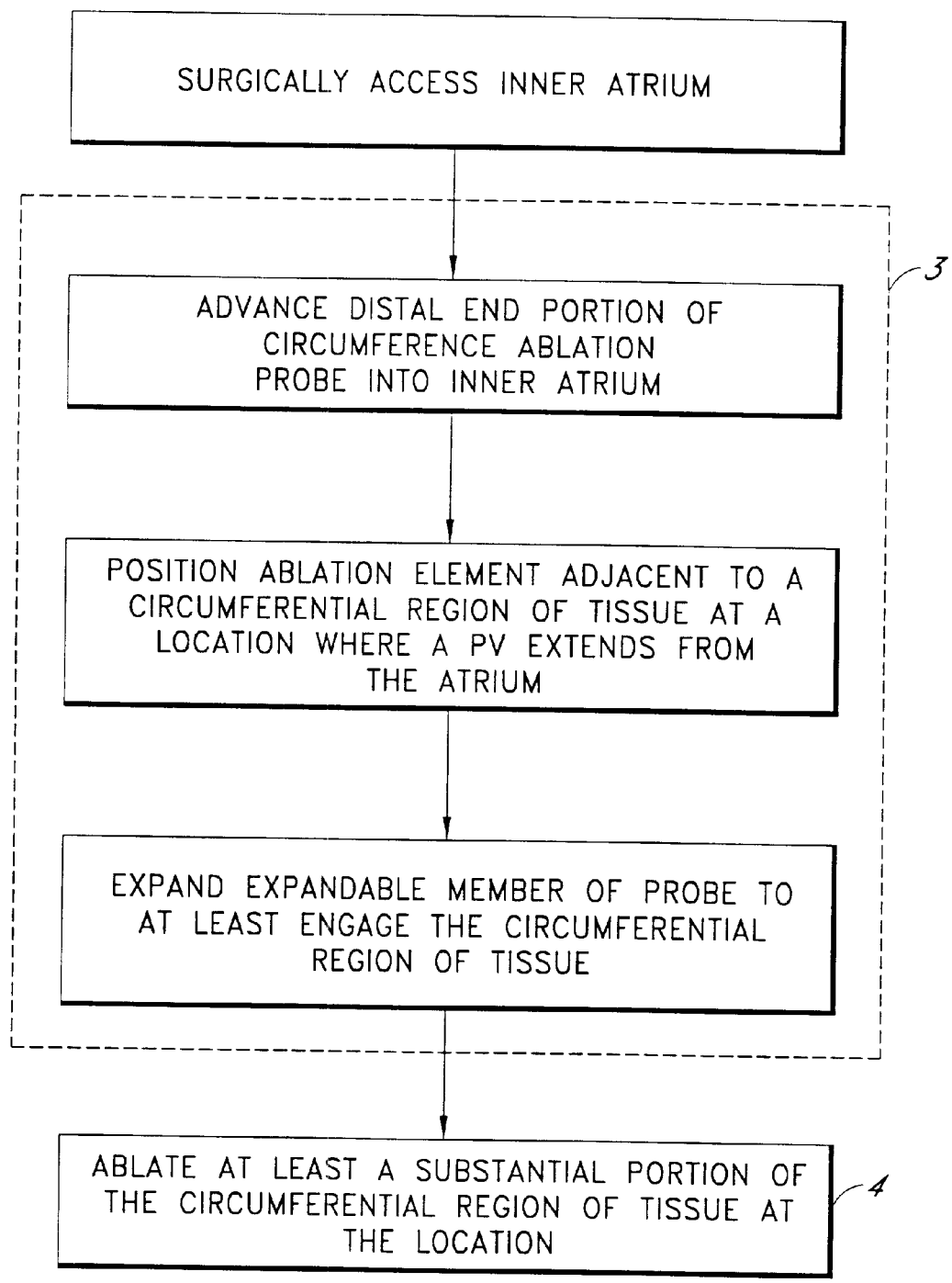
FIG. 3 diagrammatically shows the steps of forming a conduction block at a location where a pulmonary vein extends from an atrium.

FIG. 3 diagrammatically shows the sequential steps of a method for using a circumferential ablation probe assembly to form a circumferential conduction block in a pulmonary vein. The circumferential ablation method according to FIG. 3 includes: positioning a circumferential ablation element at an ablation region along the pulmonary vein according to a series of detailed steps shown collectively in FIG. 3 as positioning step (3); and thereafter ablating a continuous circumferential region of tissue in the pulmonary vein wall at the ablation region according to ablation step (4). Subsequent to gaining pulmonary vein access, positioning step (3) of FIG. 3 next includes positioning a circumferential ablation element at an ablation region of the pulmonary vein where the circumferential conduction block is to be desirably formed.

Figure 4:
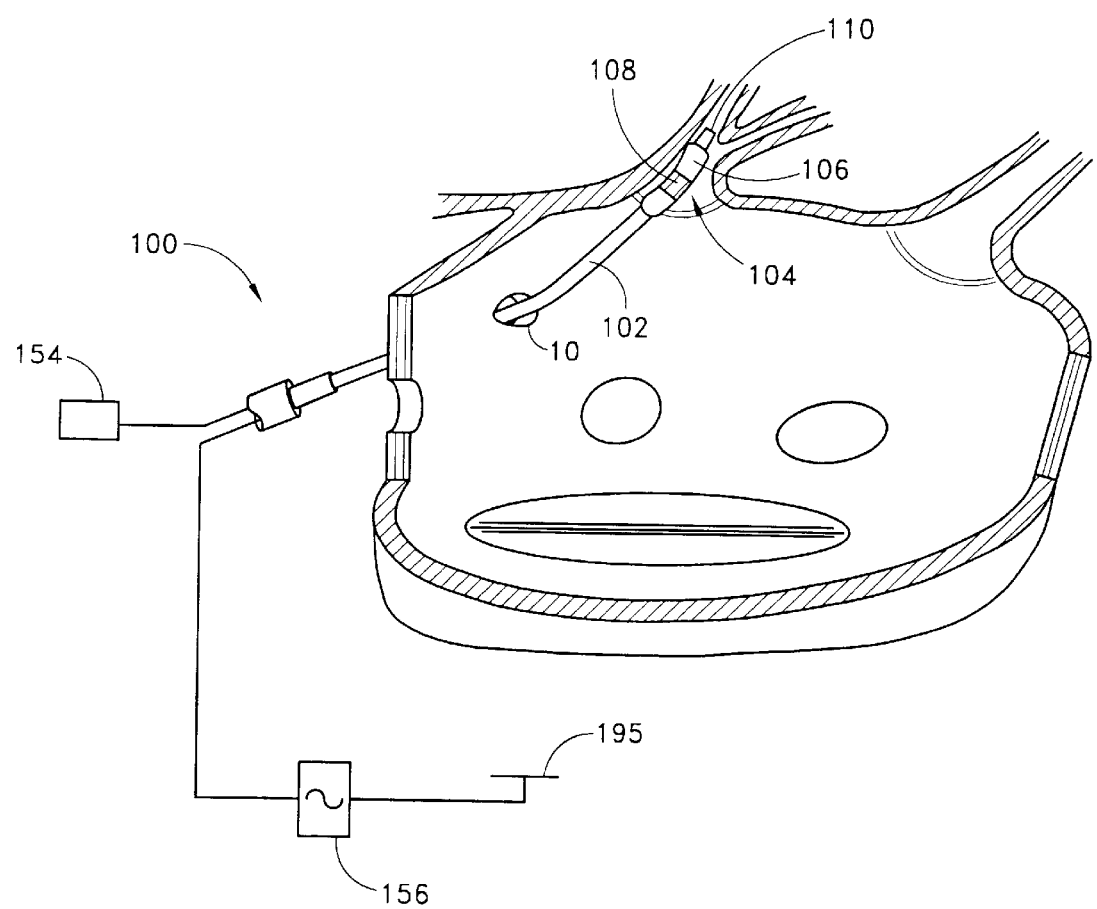
FIG. 4 shows a perspective view of a circumferential ablation probe during use in a left atrium subsequent to performing atrial access steps according to the method of FIG. 3.

FIG. 4 shows a circumferential ablation probe 100 during use in performing positioning step (3) just described with reference to FIG. 3. The circumferential ablation probe 100 generally comprises a shaft 102, an atraumatic tip 110, and a circumferential ablation member 104. The circumferential ablation member 104 includes an expandable member 106 and an ablation element 108. The ablation element 108 includes a circumferential band (shown in hatched) on the outer surface of the expandable member that ablatively couples to the surrounding tissue to form a circumferential lesion.

More specifically, FIG. 4 shows the circumferential ablation probe 100 subsequent to advancing the distal end portion into the inner atrium according to step (3) of FIG. 3, and also subsequent to advancement and positioning of the circumferential ablation member 104 within a pulmonary vein, also according to step (3) of FIG. 3. FIG. 4 also schematically illustrates the proximal end of the circumferential ablation probe 100 including an expansion actuator 154, an ablation actuator 156, and a ground patch 195.

Figure 5:
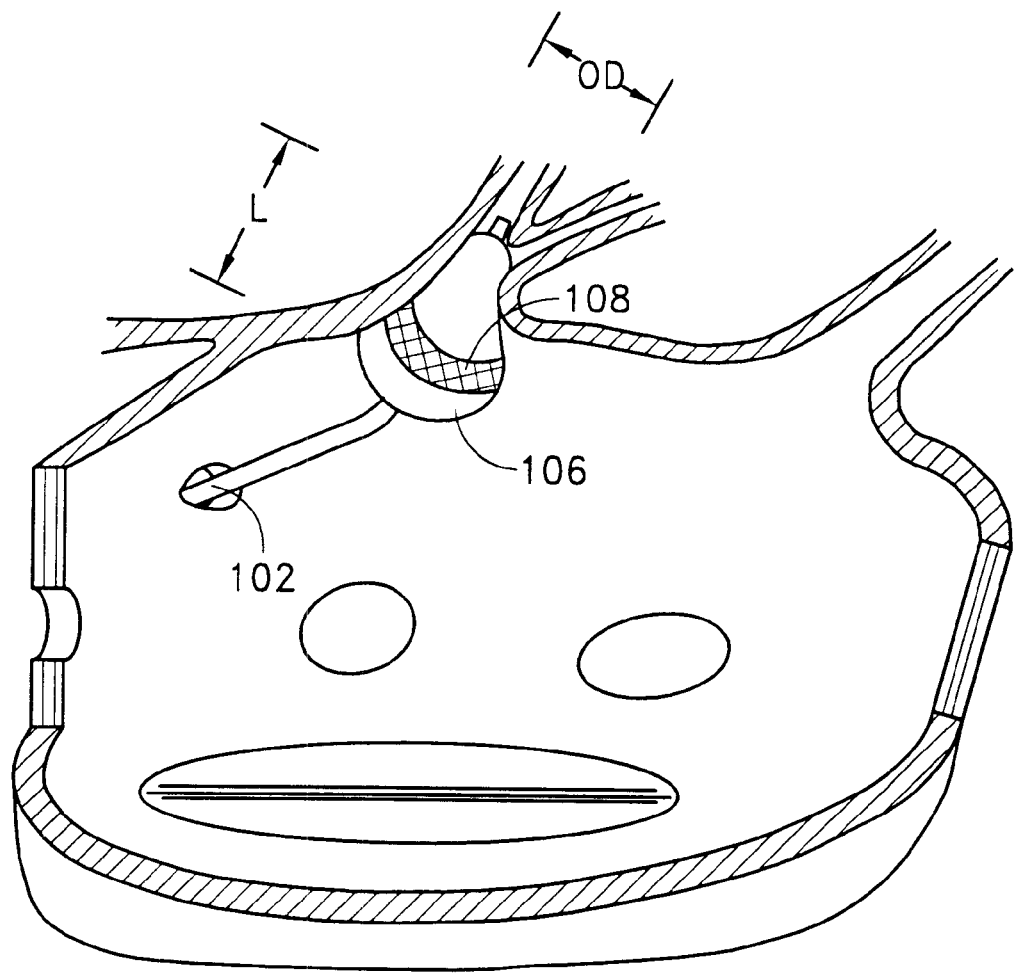
FIG. 5 shows a similar perspective view of the circumferential ablation device assembly shown in FIG. 4, and further shows the circumferential ablation probe with an expandable member shown in a radially expanded condition during use in ablating a circumferential region of tissue along a pulmonary vein wall.

FIG. 4 shows the circumferential ablation probe 100 with the expandable member 106 in a radially collapsed position adapted for delivery into the pulmonary vein according to positioning step (3) of FIG. 3. However, the expandable member 106 is adjustable to a radially expanded position when actuated by the expansion actuator 154, as shown in FIG. 5. The expansion actuator 154 may include, but is not limited to, a pressurizable fluid source. According to the expanded state shown in FIG. 5, the expandable member 106 includes a working length L relative to the longitudinal axis of the elongate catheter body which has a larger expanded outer diameter OD than when in the radially collapsed position. Furthermore, the expanded outer diameter OD is sufficient to circumferentially engage the ablation region of the pulmonary vein. Therefore, the terms "working length" are herein intended to mean the length of an expandable member which, when in a radially expanded position, has an expanded outer diameter that is: (a) greater than the outer diameter of the expandable member when in a radially collapsed position; and (b) sufficient to engage a body space wall or adjacent ablation region surrounding the expandable member, at least on two opposing internal sides of the body space wall or adjacent ablation region, with sufficient surface area to anchor the expandable member.

The circumferential ablation element 108 includes a circumferential band on the outer surface of the expandable member 106 which is coupled to an ablation actuator 156 at a proximal end portion of the probe shaft (shown schematically in FIG. 4). The ablation element 108 is actuated by ablation actuator 156 to ablatively couple to the surrounding circumferential path of tissue in the pulmonary vein wall, thereby forming a circumferential lesion that circumscribes the pulmonary vein lumen and transects the electrical conductivity of the pulmonary vein to block conduction in a direction along its longitudinal axis.

Figure 6:
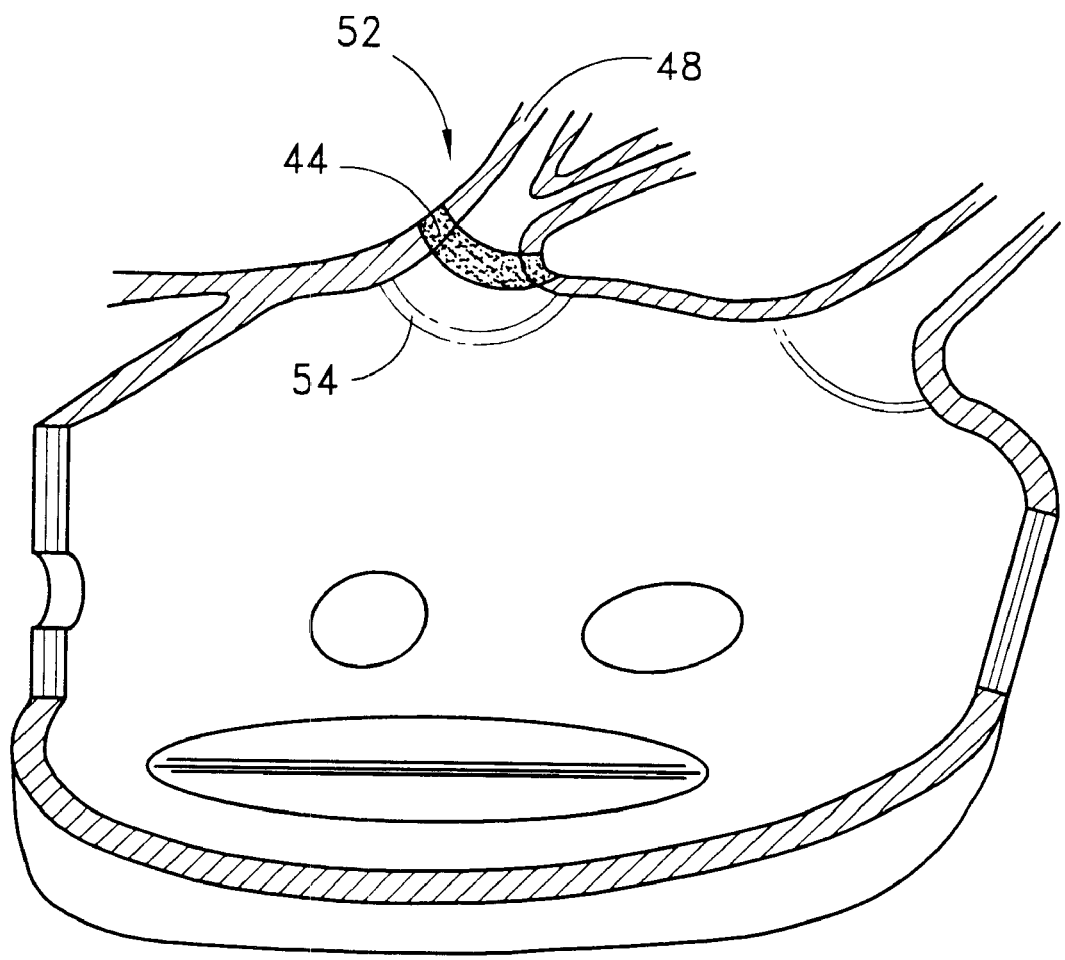
FIG. 6 shows a similar perspective view of the left atrium that is shown in FIGS. 4–5, although illustrating a cross-sectional view of a circumferential lesion after being formed by the circumferential probe ablation according to the method of FIG. 3.

FIG. 6 shows pulmonary vein 52 after removing the circumferential ablation device assembly subsequent to forming a circumferential lesion 44 around the ablation region of the pulmonary vein wall 48 according to the use of the circumferential ablation probe assembly 100 shown in stepwise fashion in FIGS. 3–5. The circumferential lesion 44 is shown located along the pulmonary vein adjacent to the pulmonary vein ostium 54, and is shown to also be "transmural," which is herein intended to mean extending completely through the wall, from one side to the other. Also, the circumferential lesion 44 is shown in FIG. 6 as a "continuous" lesion, which is herein intended to mean without gaps around the pulmonary vein wall circumference, thereby circumscribing the pulmonary vein lumen.

However, it is believed that a circumferential ablation probe with a circumferential ablation element may leave some tissue, either transmurally or along the circumference of the lesion, which is not actually ablated, but which is not substantial enough to allow for the passage of conductive signals. Therefore, the terms "transmural" and "continuous" as just defined are intended to have functional limitations, wherein some tissue in the ablation region may be unablated but there are no functional gaps which allow for symptomatically arrhythmogenic signals to conduct through the conduction block and into the atrium from the pulmonary vein.

Moreover, it is believed that the functionally transmural and continuous lesion qualities just described are characteristic of a completed circumferential conduction block in the pulmonary vein. Such a circumferential conduction block thereby transects the vein, isolating conduction between the portion of the vein on one longitudinal side of the lesion and the portion on the other side. Therefore, any foci of originating arrhythmogenic conduction which is opposite the conduction block from the atrium is prevented by the conduction block from conducting down into the atrium and atrial arrhythmic affects are therefore nullified.

Figure 7:
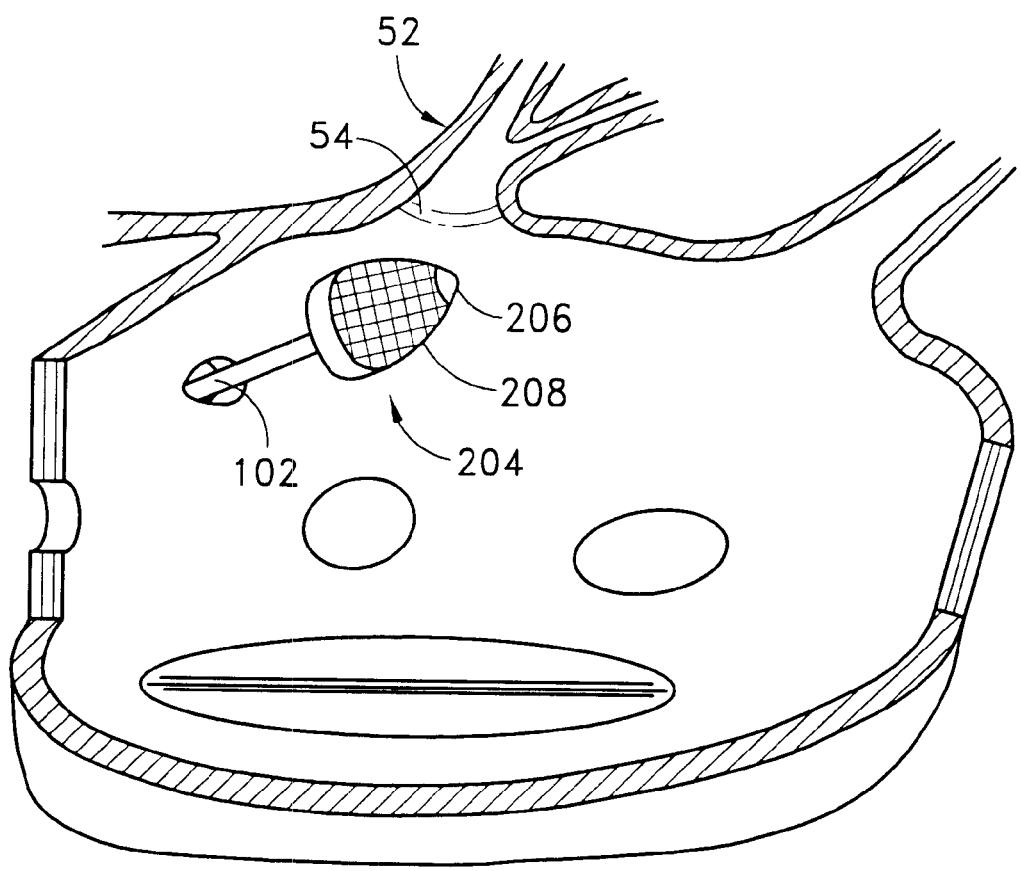
FIG. 7 shows a perspective view of another circumferential ablation probe variation during use in a left atrium according to the method of FIG. 3 wherein the ablation element is formed to also engage a circumferential path of tissue along the left posterior wall which surrounds the pulmonary vein ostium.
Figure 8:
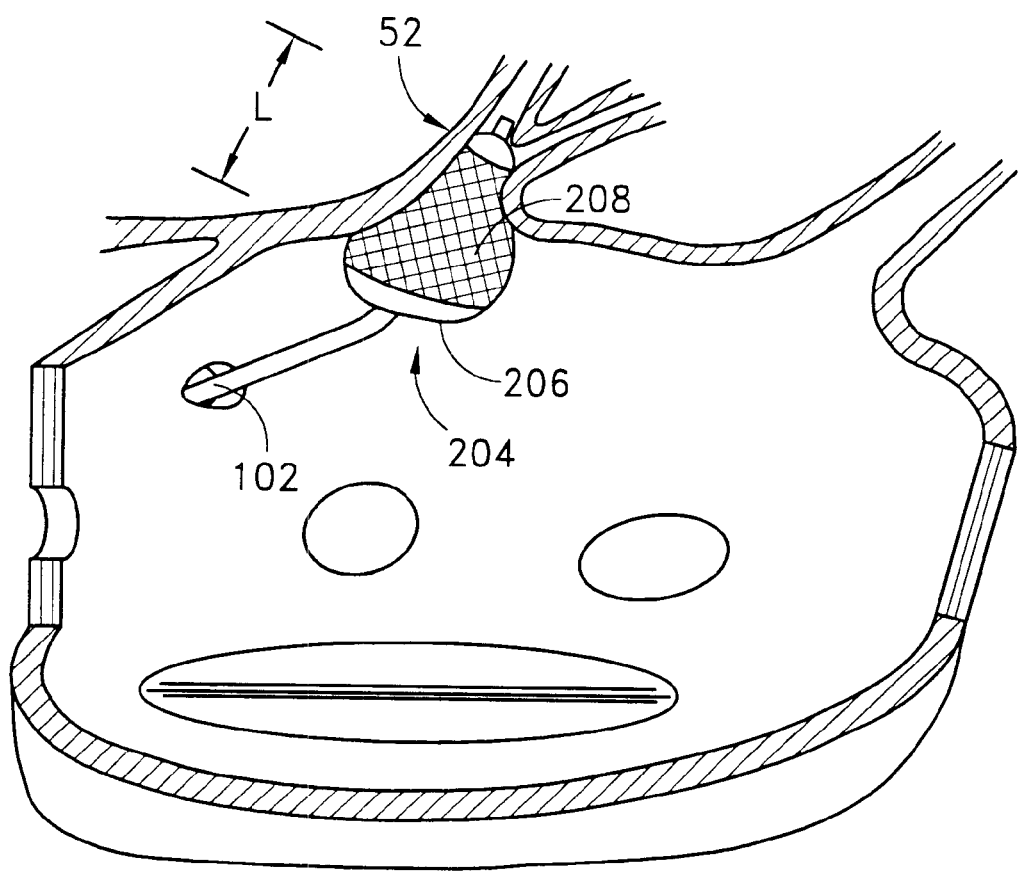
FIG. 8 shows a perspective view of the circumferential ablation probe of the FIG. 7 variation during use in a left atrium according to the method of FIG. 3, showing the expandable member after advancing it into and engaging a pulmonary vein ostium while in the radially expanded position.
Figure 9:
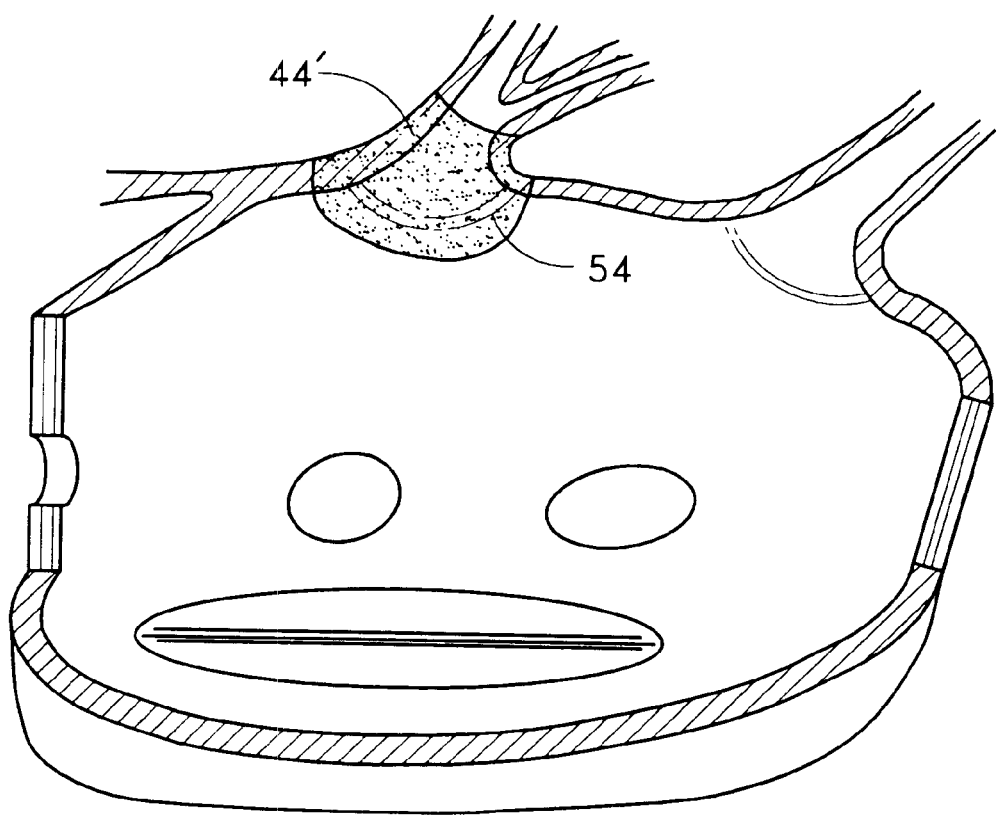
FIG. 9 shows the same perspective view of the left atrium shown in FIGS. 7–8, although shown after forming a circumferential conduction block according to the circumferential ablation procedure of FIG. 3 wherein the circumferential lesion extends onto the left posterior wall.

FIGS. 7–8 illustrate another variation of a circumferential ablation member 204 that includes a radially compliant expandable member 206 and an ablation element 208 adapted to ablatively couple to a larger region of tissue. FIG. 7 illustrates the expandable member 206 after being adjusted to a radially expanded position while located in the left atrium. FIG. 8 further shows the expandable member 206 after being advanced into the pulmonary vein 52 until at least a portion of the expanded working length L of the ablation element 208, which includes a circumferential band, engages the pulmonary vein ostium (shown as 54 in FIG. 7). FIG. 9 illustrates a portion of the circumferential lesion 44' that provides a circumferential conduction block in the region of the pulmonary vein ostium 54 subsequent to actuating the circumferential ablation element.

In the embodiment described in FIGS. 7–8, the expandable member 206 is formed to also engage a circumferential path of tissue along the left posterior atrial wall that surrounds the ostium 54. Moreover, the ablation element 208 of the circumferential ablation member 204 is also thereby adapted to engage that atrial wall tissue. Therefore, the circumferential lesion 44' formed according to the method shown in part in FIG. 9, and just described in sequential steps by reference to FIGS. 7–8, includes ablating a circumferential path of atrial wall tissue which surrounds the ostium 54. Accordingly, the entire pulmonary vein 52, including the ostium 54, is thereby electrically isolated from at least a substantial portion of the left atrial wall. The circumferential lesion 44' also isolates the other of the pulmonary vein ostia, as would be apparent to one of ordinary skill according to the sequential method steps shown in FIGS. 7–8 and by further reference to the resulting circumferential lesion 44' shown in FIG. 9.

Figure 10:
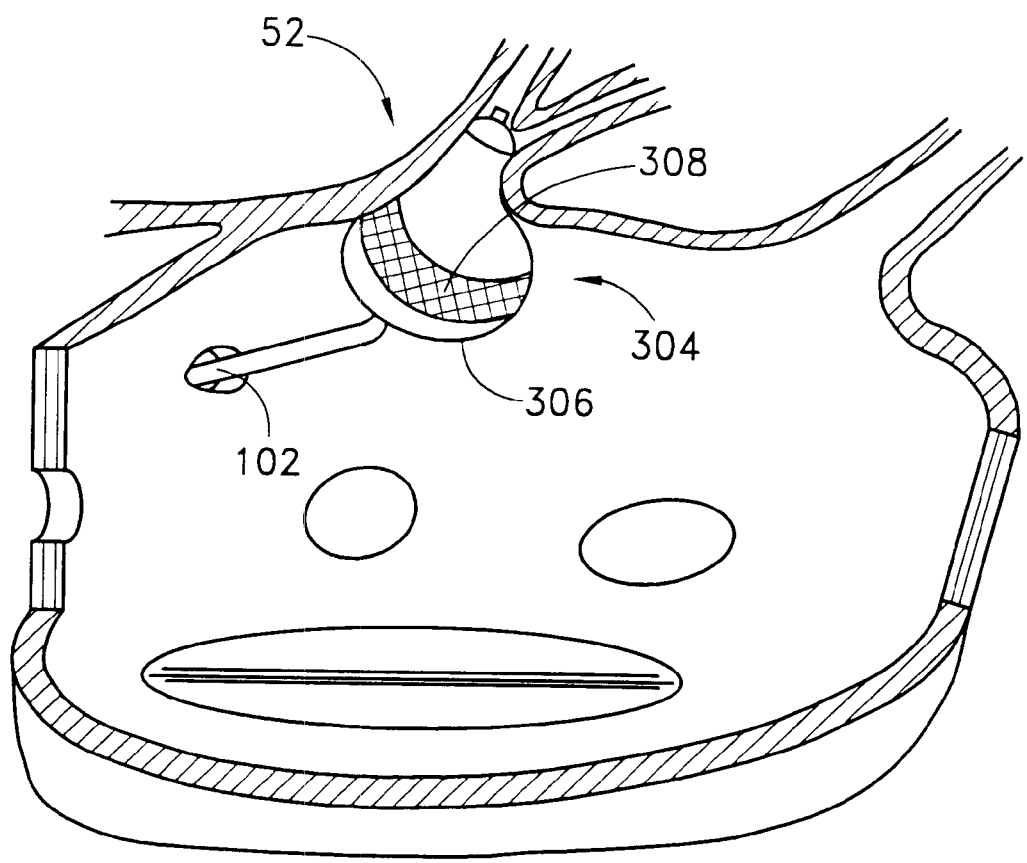
FIG. 10 shows a perspective view of another circumferential ablation probe during use in a left atrium wherein the ablation element is formed to engage only a circumferential path of tissue along the left posterior wall and does not extend into the pulmonary vein.

FIG. 10 shows yet another variation of a circumferential ablation member 308 and use thereof for electrically isolating a pulmonary vein and ostium from a substantial portion of the left posterior atrial wall. However, unlike the embodiment previously shown and described by reference to FIGS. 7–8, the FIG. 10 embodiment isolates the pulmonary vein without also ablating tissue along the lumen or lining of the pulmonary vein or ostium. This is apparent by reference to the resulting circumferential conduction block 44" shown in FIG. 11.

Figure 11:
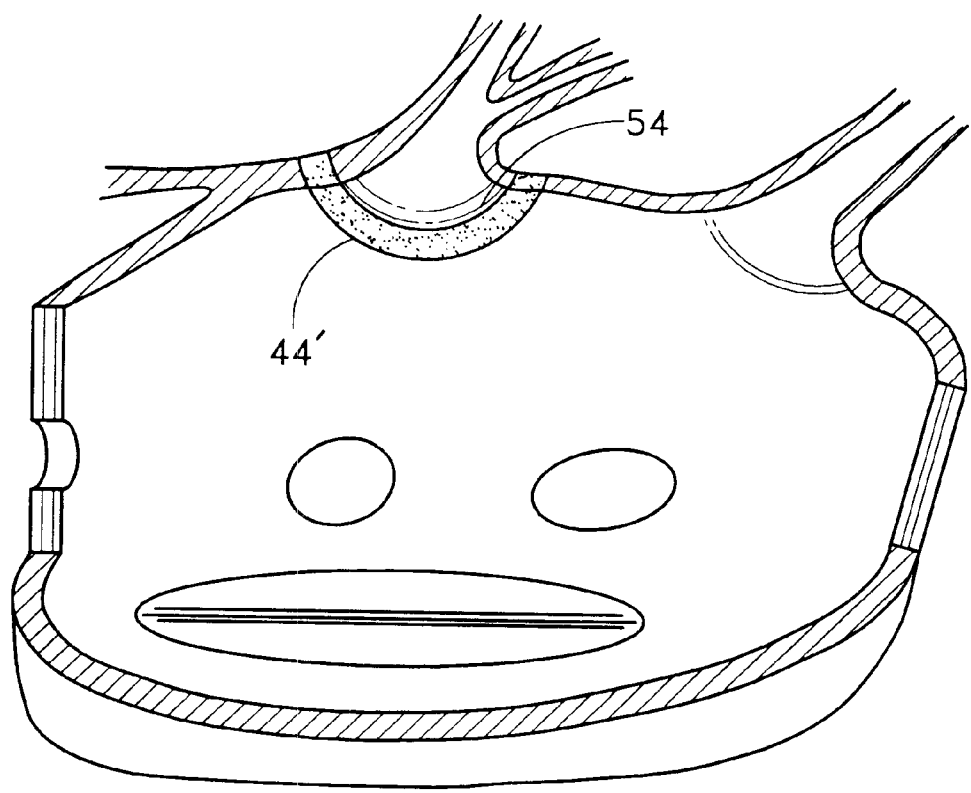
FIG. 11 shows a resulting circumferential conduction block or lesion which may be formed with the assembly and the method of use shown in FIG. 10.

In more detail, FIG. 10 shows a similar device assembly as that shown in FIGS. 7–8, except that ablation element 308 is adapted to ablatively couple with only a circumferential path of tissue along the left posterior atrial wall which surrounds the pulmonary vein ostium. In one aspect of this embodiment, the compliant nature of the expandable member 306 may be self-conforming to the region of the ostium such that the ablation element 308 is placed against this atrial wall tissue merely by way of conformability. FIG. 11 illustrates a circumferential lesion 44" formed by the device assembly discussed with reference to FIG. 10. As shown, the circumferential lesion 44" is located along the posterior wall and does not extend into or around the ostium 54.

In another aspect of this embodiment, a "pear"-shaped expandable member or balloon that includes a contoured taper may be suitable for use according to the FIG. 10 embodiment. Such a pear shape may be preformed into the expandable member or balloon, or the member may be adapted to form this shape by way of controlled compliance as it expands, such as for example by the use of composite structures within the balloon construction. In any case, according to the "pear"-shaped variation, the circumferential band of the ablation member is preferably placed along the surface of the contoured taper which is adapted to face the left posterior atrial wall during use according to the method illustrated by FIG. 10. It is further contemplated that the ablation element may be further extended or alternatively positioned along other portions of the taper.

The method of forming a circumferential conduction block along a circumferential path of tissue along a left posterior atrial wall and which surrounds a pulmonary vein ostium without ablating the tissue of the vein or ostium should not be limited to the particular device embodiments just illustrated by reference to FIG. 10. Other device variations may be acceptable substitute for use according to this method. In one particular example which is believed to be suitable, a "looped" ablation member such as the embodiment illustrated below by reference to FIG. 28 may be adapted to form a "looped" ablation element within the left atrium and then be advanced against the left posterior atrial wall such that the loop engages the circumferential path of tissue along the atrial wall and which surrounds a vein ostium. Thereafter, the looped ablation element may be actuated to ablate the engaged tissue, such as for further illustration like a branding iron forming the predetermined pattern around the pulmonary vein ostium. In addition, other device or method variations may also be suitable substitutes according to one of ordinary skill.

Combining Circumferential Lesions with Long Linear Lesions

FIGS. 12–17 collectively illustrate a circumferential ablation device assembly and method as used to form a circumferential lesion in combination with the formation of long linear lesions in a less-invasive "maze"-type procedure, as described above for the treatment of multiwavelet reentrant type fibrillation along the left atrial wall. As described in part by the flow diagram of FIG. 12, the physician may use a linear ablation element to form linear conduction blocks between the pulmonary vein ostia, wherein the circumferential ablation probe of the present invention is used to connect the linear lesions by forming circumferential ablation lesions around the pulmonary vein ostia.

Figure 12:
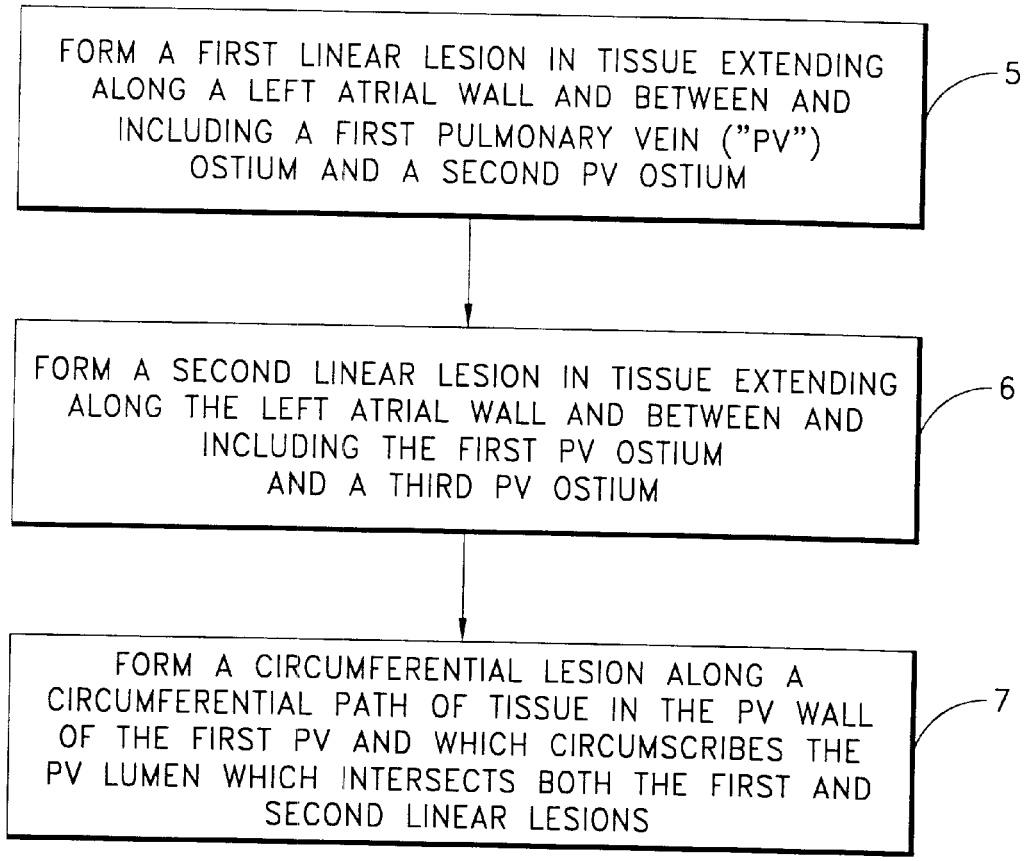
FIG. 12 diagrammatically shows a method for using a circumferential ablation device assembly to form a circumferential conduction block in a pulmonary vein in combination with a method for forming long linear lesions between pulmonary vein ostia in a less-invasive "maze"-type procedure.
Figure 13:
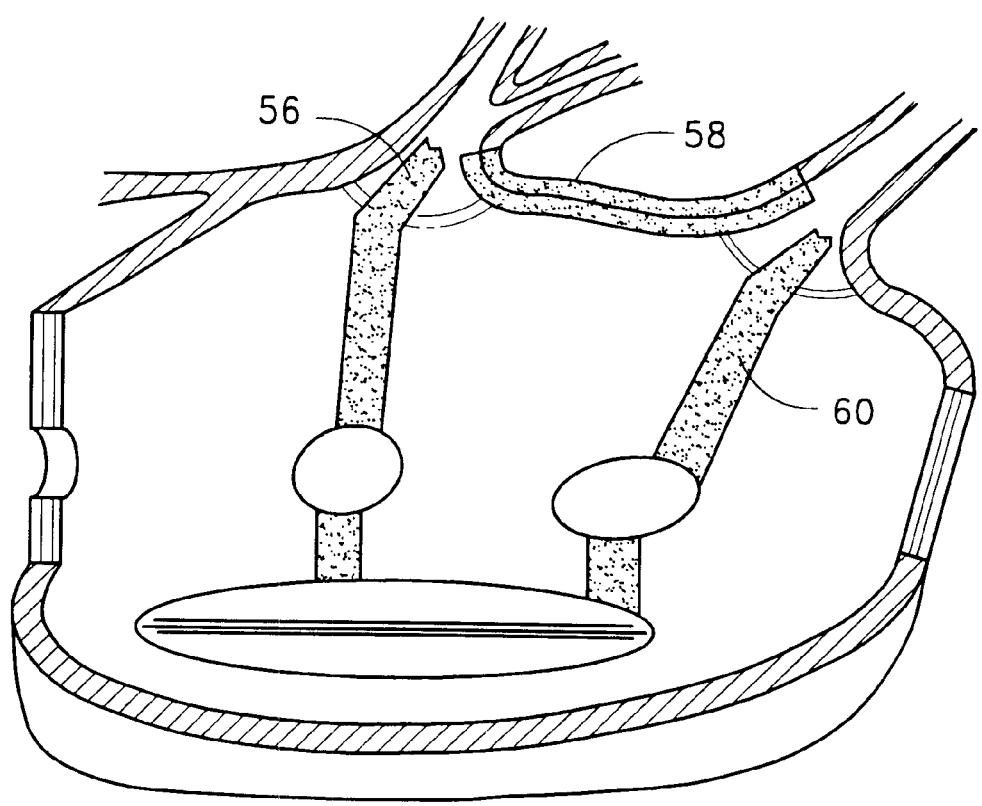
FIG. 13 shows a perspective view of a segmented left atrium after forming several long linear lesions between adjacent pairs of pulmonary vein ostia according to the method of FIG. 12.

More specifically, FIG. 12 diagrammatically shows a summary of steps for performing a "maze"-type procedure by forming circumferential conduction blocks that intersect with long linear conduction blocks formed between the pulmonary veins. As disclosed in U.S. Pat. No. 5,971,983 to Lesh entitled "Tissue Ablation Device and Method of Use", which is herein incorporated in its entirety by reference thereto, a box-like conduction block surrounding an arrhythmogenic atrial wall region bounded by the pulmonary veins may be created by forming long linear lesions between anchors in all pairs of adjacent pulmonary vein ostia. This procedure is summarized in steps (5) and (6) of FIG. 12. However, it is further believed that, in some particular applications, such linear lesions may be made sufficiently narrow with respect to the surface area of the pulmonary vein ostia that they may not intersect, thereby leaving gaps between them which may present proarrhythmic pathways for abnormal conduction into and from the box. This is illustrated in FIG. 13 by the gaps between lesion 56 and 58 and also between lesions 58 and 60. Therefore, by forming a circumferential conduction block according to step (7) of FIG. 12, and as shown by use of ablation element 208 in FIG. 14, the linear lesions are thereby bridged and the gaps are closed. FIG. 15 illustrates a lesion pattern formed by steps (5)–(7) of FIG. 12. With the addition of circumferential lesion 44', there are no gaps between the linear lesions and therefore there are no proarrhythmic pathways for abnormal conduction into and out of the box.

Figure 14:
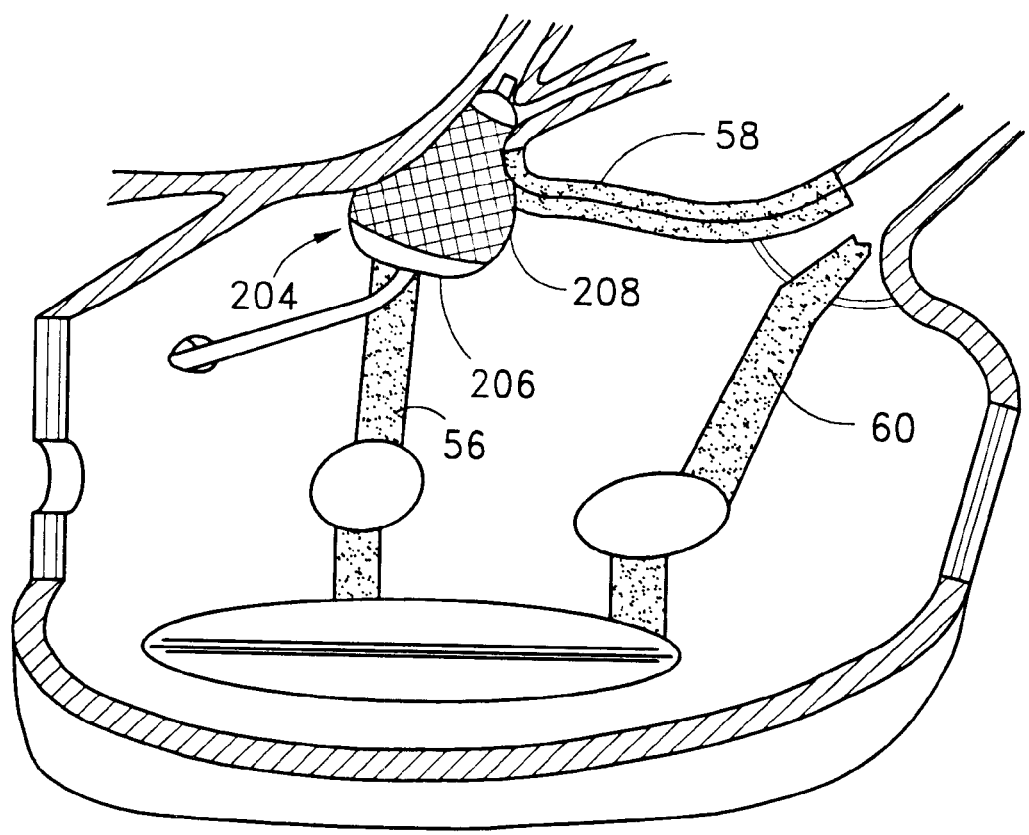
FIG. 14 shows a similar perspective view as that shown in FIG. 13, although showing a circumferential ablation device assembly during use in forming a circumferential lesion in a pulmonary vein which intersects with two linear lesions that extend into the pulmonary vein, according to the method of FIG. 12.
Figure 15:
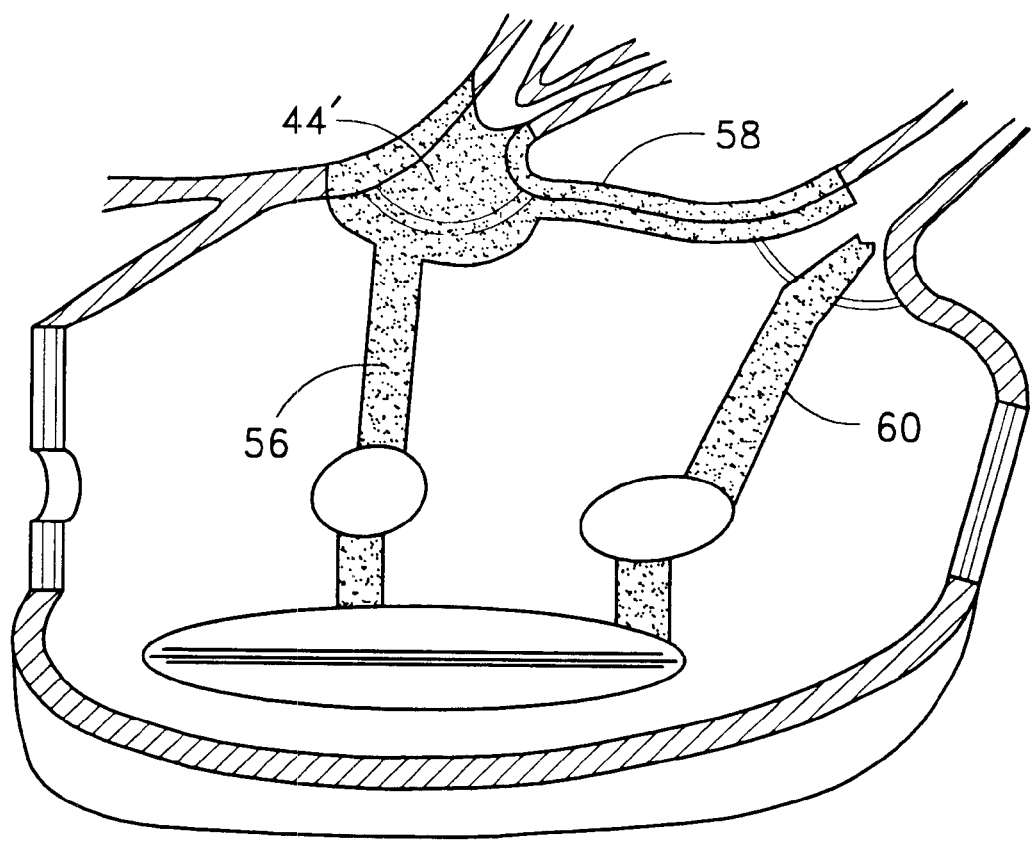
FIG. 15 shows a perspective view of a segmented left posterior atrial wall with a lesion pattern which results from combining the formation of two linear lesions according to FIG. 12 with the formation of a circumferential conduction block according to the methods and devices shown in FIGS. 7–8.
Figure 16:
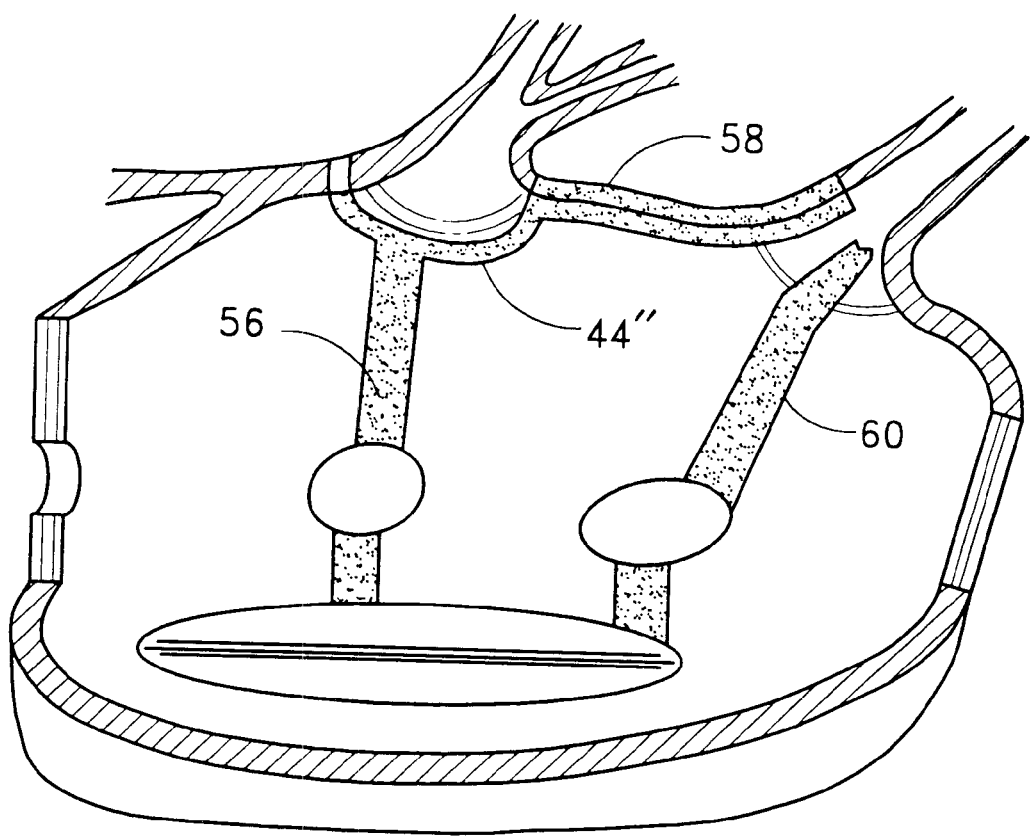
FIG. 16 shows a perspective view of a segmented left posterior atrial wall with a lesion pattern which results from combining the formation of two linear lesions according to FIG. 12 with the formation of a circumferential conduction block according to the methods and devices shown in FIGS. 10–11.

Moreover, the method shown schematically in FIG. 12 and also in various detail by reference to FIGS. 13–15 provides a specific sequence of steps for the purpose of illustration. According to this illustrative sequence, the linear lesions are formed first and then are connected thereafter with the circumferential conduction block. However, a circumferential conduction block may be formed prior to the formation of the linear lesions or conduction blocks, or in any other combination or sub-combination of sequential steps, so long as the resulting combination of lesions allows for the circumferential block to intersect with and connect with the linear lesions. In addition, the circumferential conduction block which connects the linear lesions may also include a circumferential path of tissue which surrounds and electrically isolates the pulmonary vein ostium from the rest of the left posterior atrial wall.

In addition to the particular embodiments just shown and described by reference to FIGS. 12–15, other methods are also contemplated for combining circumferential and linear conduction blocks device assemblies and uses in order to perform a less-invasive "maze"-type procedure. In a further example shown in FIG. 16, another lesion pattern is formed by combining the pair of linear lesions of FIG. 13 with a circumferential conduction block 44". While the resulting lesion patterns of FIGS. 15 and 16 differ slightly as regards the particular geometry and position of the circumferential conduction block formed, the two variations are also similar in that the circumferential conduction block includes a circumferential path of atrial wall tissue. When such circumferential conduction blocks are formed between adjacent pulmonary vein ostia, shorter linear lesions are therefore sufficient to bridge the circumferential lesions during the overall "maze"-type procedure.

To this end, according to one contemplated less-invasive "maze"-type procedure (not shown) wherein multiple circumferential conduction blocks are formed in atrial wall tissue such that each pulmonary vein ostium is surrounded by and is electrically isolated with one circumferential conduction block. A series of four linear lesions may be formed between the various pairs of adjacent ostia and with just sufficient length to intersect with and bridge the corresponding adjacent circumferential blocks. A box-like conduction block is thereby formed by the four circumferential conduction blocks and the four bridging linear lesions. A fifth linear lesion may be also formed between at least a portion of the box-like conduction block and another predetermined location, such as for example the mitral value annulus.

Figure 17:
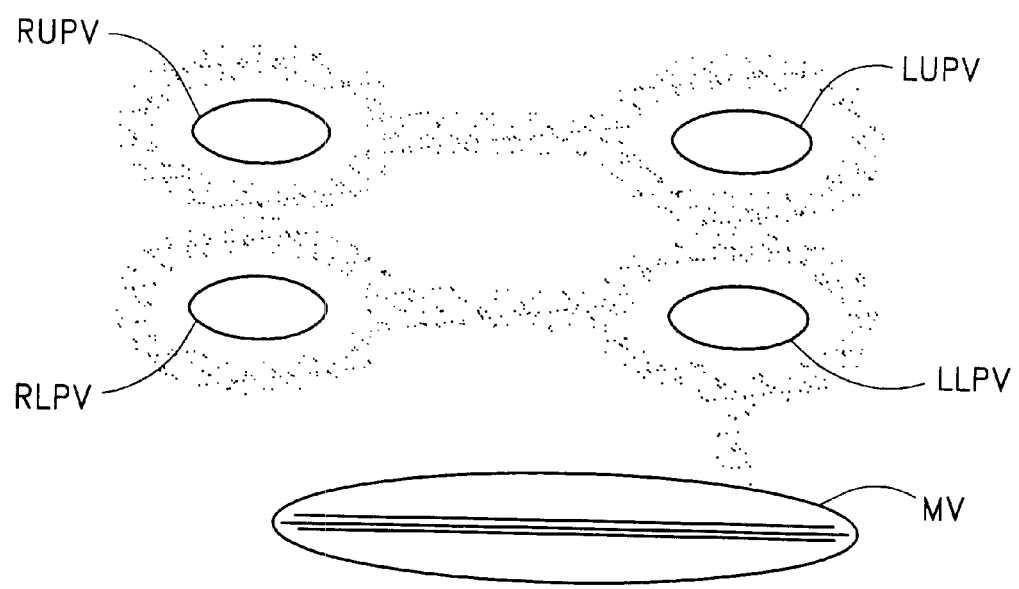
FIG. 17 shows a schematic perspective view of a left posterior atrial wall with one complete lesion pattern in a variation of a less-invasive "maze"-type procedure wherein circumferential conduction blocks are formed along circumferential paths of tissue along a left posterior atrial wall such that each circumferential conduction block surrounds a pulmonary vein ostium, each pair of vertically adjacent circumferential conduction blocks intersects, and each pair of horizontally adjacent circumferential conduction blocks are connected with one of two linear lesions extending between the respective pair of horizontally adjacent pulmonary vein ostia.

FIG. 17 schematically illustrates yet a further variation for forming circumferential conduction blocks along atrial wall tissue around the pulmonary vein ostia during a less invasive "maze"-type procedure. According to this further variation, the circumferential conduction block patterns formed around each of two adjacent superior and inferior pulmonary vein ostia are shown in FIG. 17 to intersect, thereby alleviating the need for a linear lesion in order to form a conduction block between the ostia. Furthermore, the distances between the inferior and superior ostia, both on the right and left side of the posterior atrial wall, are believed to be significantly shorter than the distances between the two adjacent superior or inferior ostia. Therefore, FIG. 17 only shows the overlapping circumferential conduction blocks as just described to be positioned vertically between the inferior-superior pairs of adjacent ostia, and further shows linear lesions which are used to connect the right and left sided ostia of the superior and inferior pairs. In some instances these linear lesions will not be required to cure, treat or prevent a particular atrial arrhythmia condition. However, other combinations of these patterns are further contemplated, such as for example using only overlapping circumferential conduction blocks between all adjacent pairs of ostia in order to form the entire "maze"-type left atrial pattern.

Monitoring Electrical Signals During Surgical Procedure

Figure 18:
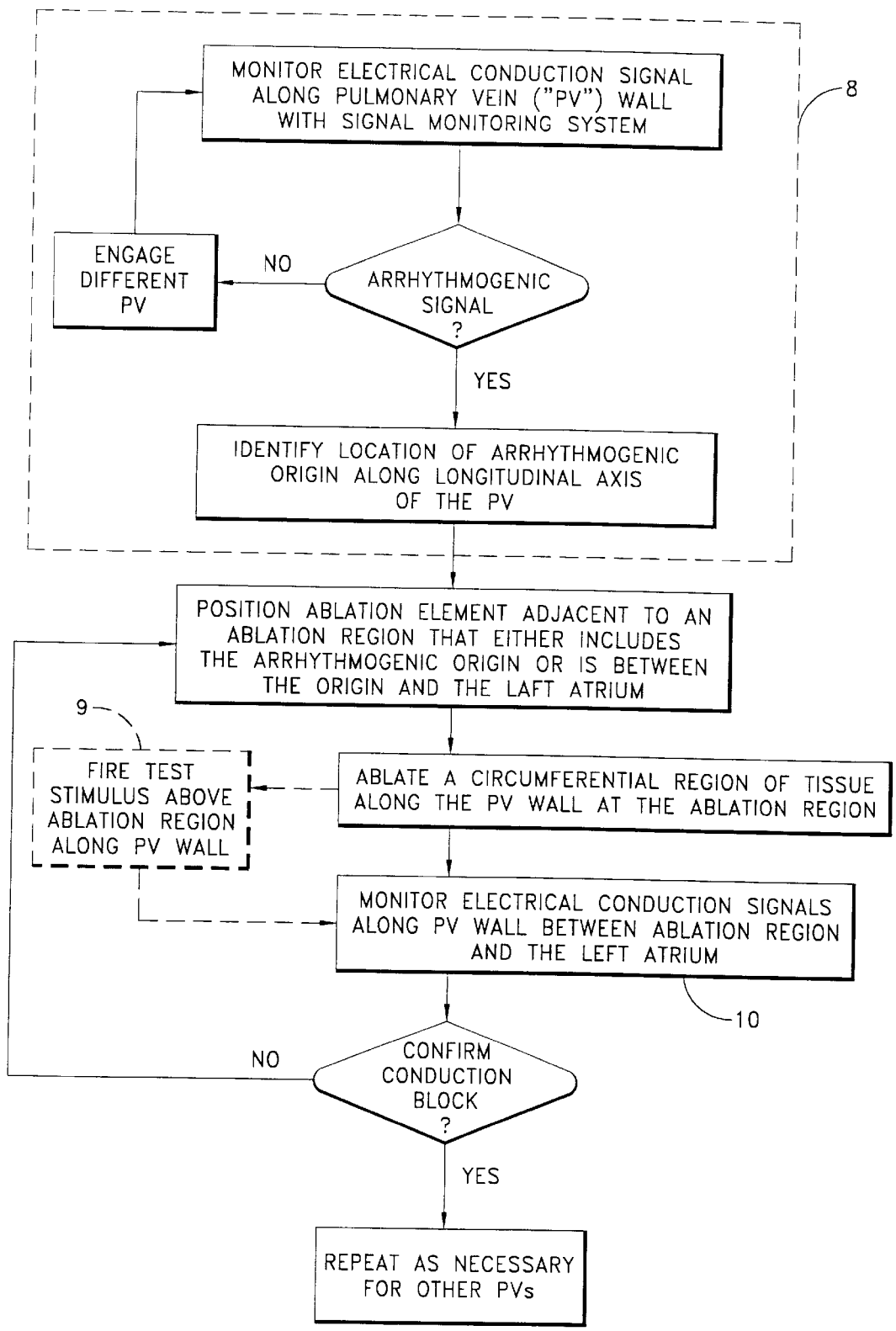
FIG. 18 diagrammatically shows a further method for using the circumferential ablation device assembly of the present invention to form a circumferential conduction block in a pulmonary vein wall, wherein signal monitoring and "post-ablation" test elements are used to locate an arrhythmogenic origin along the pulmonary vein wall and to test the efficacy of a circumferential conduction block in the wall, respectively.

FIG. 18 diagrammatically shows a further method for using a circumferential ablation device assembly wherein electrical signals along the pulmonary vein are monitored with a sensing element before and after ablation according to steps (8) and (9), respectively. Signals within the pulmonary vein are monitored prior to forming a conduction block, as indicated in step (8) in FIG. 18, in order to confirm that the pulmonary vein chosen contains an arrhythmogenic origin for atrial arrhythmia. Failure to confirm an arrhythmogenic origin in the pulmonary vein, particularly in the case of a patient diagnosed with focal arrhythmia, may dictate the need to monitor signals in another pulmonary vein in order to direct treatment to the proper location in the heart. In addition, monitoring the pre-ablation signals may be used to indicate the location of the arrhythmogenic origin of the atrial arrhythmia, which helps determine the best location to form the conduction block. As such, the conduction block may be positioned to include and therefore ablate the actual focal origin of the arrhythmia, or may be positioned between the focus and the atrium in order to block aberrant conduction from the focal origin and into the atrial wall.

In addition or in the alternative to monitoring electrical conduction signals in the pulmonary vein prior to ablation, electrical signals along the pulmonary vein wall may also be monitored by the sensing element subsequent to circumferential ablation, according to step (9) of the method of FIG. 18. This monitoring method aids in testing the efficacy of the ablation in forming a complete conduction block against arrhythmogenic conduction. Arrhythmogenic firing from the identified focus will not be observed during signal monitoring along the pulmonary vein wall when taken below a continuous circumferential and transmural lesion formation, and thus would characterize a successful circumferential conduction block. In contrast, observation of such arrhythmogenic signals between the lesion and the atrial wall characterizes a functionally incomplete or discontinuous circumference (gaps) or depth (transmurality) which would potentially identify the need for a subsequent follow-up procedure, such as a second circumferential lesioning procedure in the ablation region.

A test electrode may also be used in a "post ablation" signal monitoring method according to step (10) of FIG. 18. In one particular embodiment not shown, the test electrode is positioned on the distal end portion of a probe shaft and is electrically coupled to a current source for firing a test signal into the tissue surrounding the test electrode when it is placed distally or "upstream" of the circumferential lesion in an attempt to simulate a focal arrhythmia. This test signal generally challenges the robustness of the circumferential lesion in preventing atrial arrhythmia from any such future physiologically generated aberrant activity along the suspect vein.

Further to the signal monitoring and test stimulus methods just described, such methods may be performed with a separate electrode or electrode pair located on the probe distal end portion adjacent to the region of the circumferential ablation element, or may be performed using one or more electrodes which form the circumferential ablation element itself, as will be further developed below.

Surgical Ablation Probe for Forming a Circumferential Lesion

Circumferential ablation devices disclosed in the past are translumenal catheter-based devices that are inserted into a peripheral vein (such as the femoral vein) and are advanced through a guide catheter into the right atrium and then across the septum into the left atrium. However, during certain open-heart or minimally invasive cardiac surgeries, the left atrium may be accessible through an opening in a patient's chest, thereby obviating the need for a catheter-based apparatus. When the physician can access the left atrium through an opening in a patient's chest, a relatively short and rigid surgical ablation probe is better suited for placing an ablation element in a selected pulmonary vein for the creation of a circumferential lesion.

Figure 19:
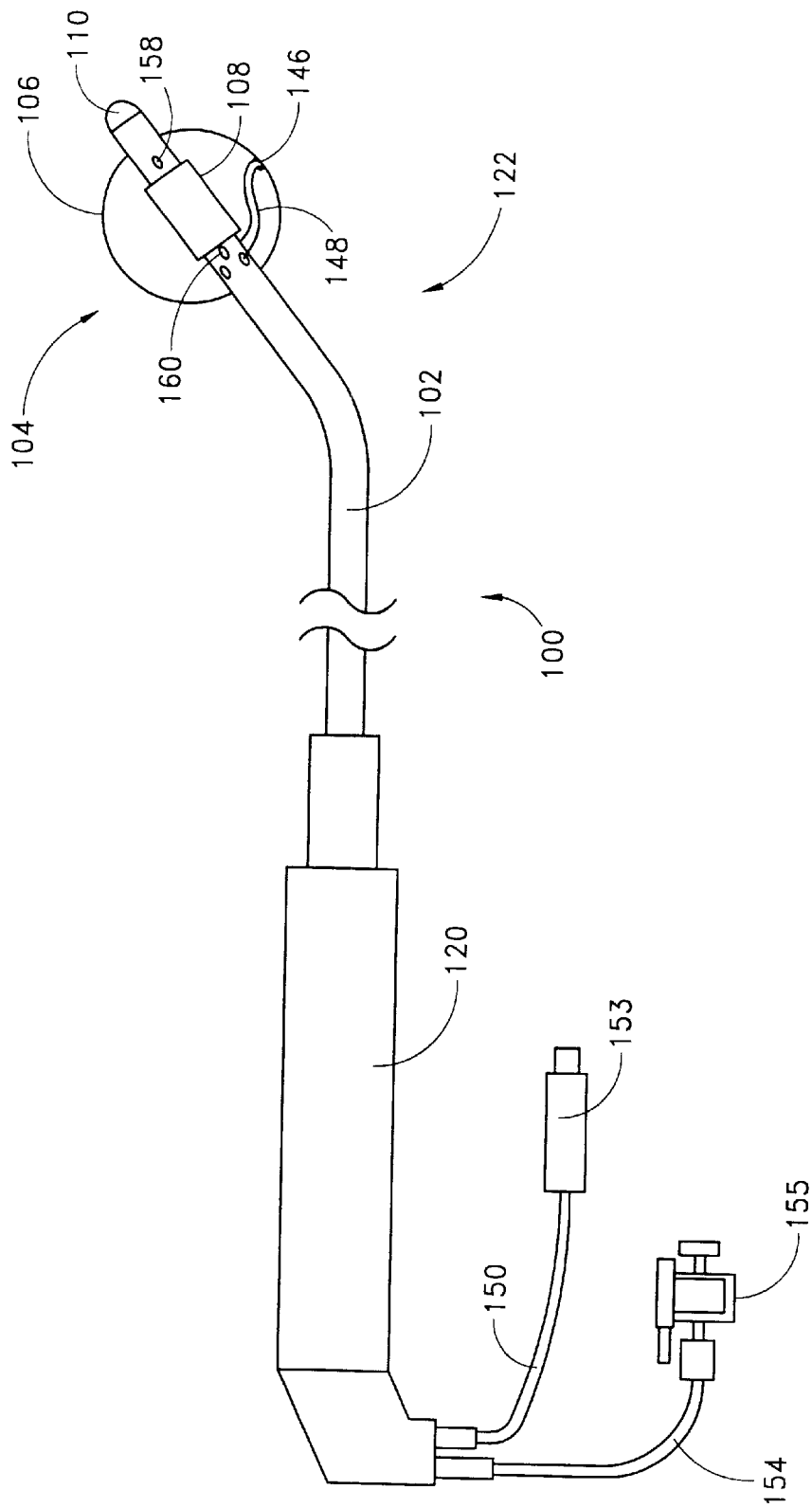
FIG. 19 shows a circumferential ablation probe in accordance with a preferred mode of the present invention having an inflatable balloon and an ultrasonic transducer disposed on the distal end for forming a circumferential lesion to treat atrial fibrillation.

With general reference to FIG. 19, a preferred mode of the surgical ablation probe in accordance with the present invention will now be described. The surgical ablation probe 100 comprises a handle 120 that includes multiple lumens and is ergonomically designed to fit comfortably in the physician's hand. The handle 120 preferably is made of a molded or machined plastic. A suitable handle design would be similar to known handles used on the following types of devices: a laser device to perform trans-myocardial revascularization (TMR); a hand-held RF ablation probe; and a hand-held cryo-ablation probe. In the case of a deflectable tip version of the probe, several exemplifying types of control handles are described in U.S. Pat. Nos. 6,024,739 and 5,465,716, which are hereby incorporated by reference.

The handle 120 supports a multi-lumen probe shaft 102 that is relatively short in length and is generally rigid. The majority of the shaft 102 is significantly less flexible than the catheter-based ablation devices described in U.S. Pat. No. 6,024,740. The distal end 122 preferably includes an atraumatic distal tip 110 made of a soft thermoplastic. The shaft 102 preferably has a diameter ranging from about 7 to about 12 F. However, this range of diameters merely exemplifies suitable diameters for use in the described surgical procedure, and other diameter probes of course are also within the scope of the invention.

Figure 22:
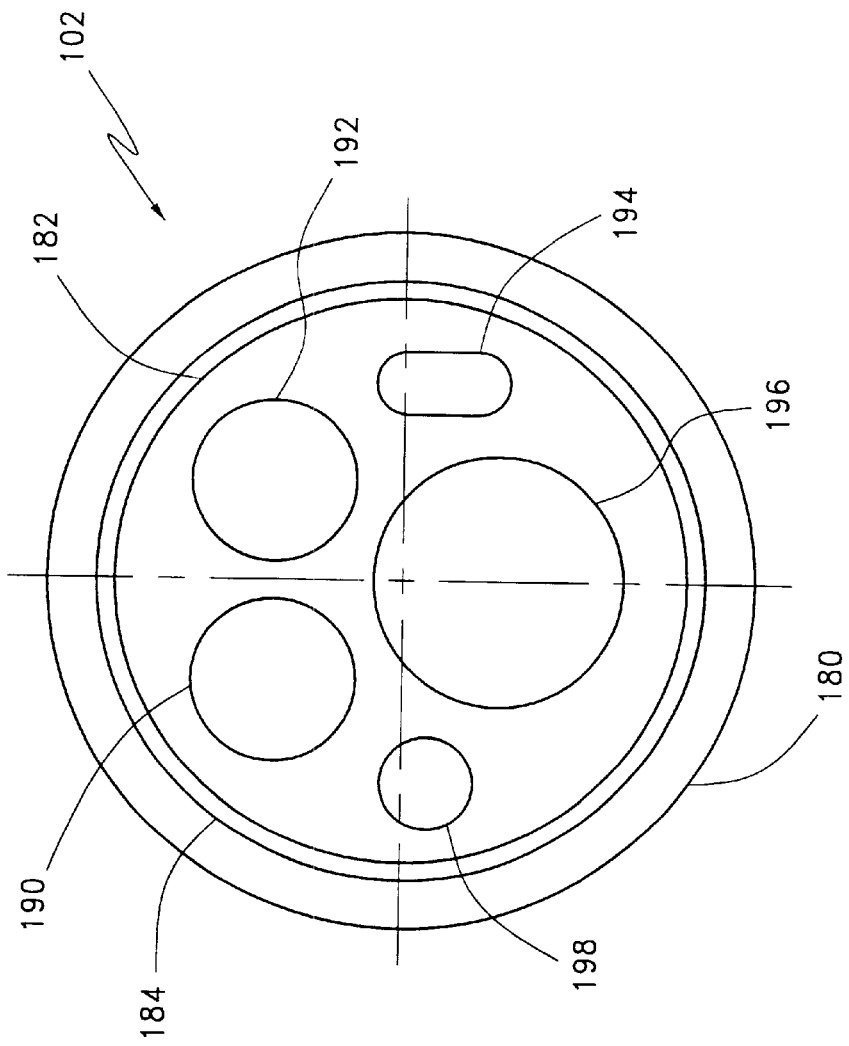
FIG. 22 is a cross-sectional view taken along line 22—22 of the circumferential ablation probe shown in FIG. 20.
Figure 23:
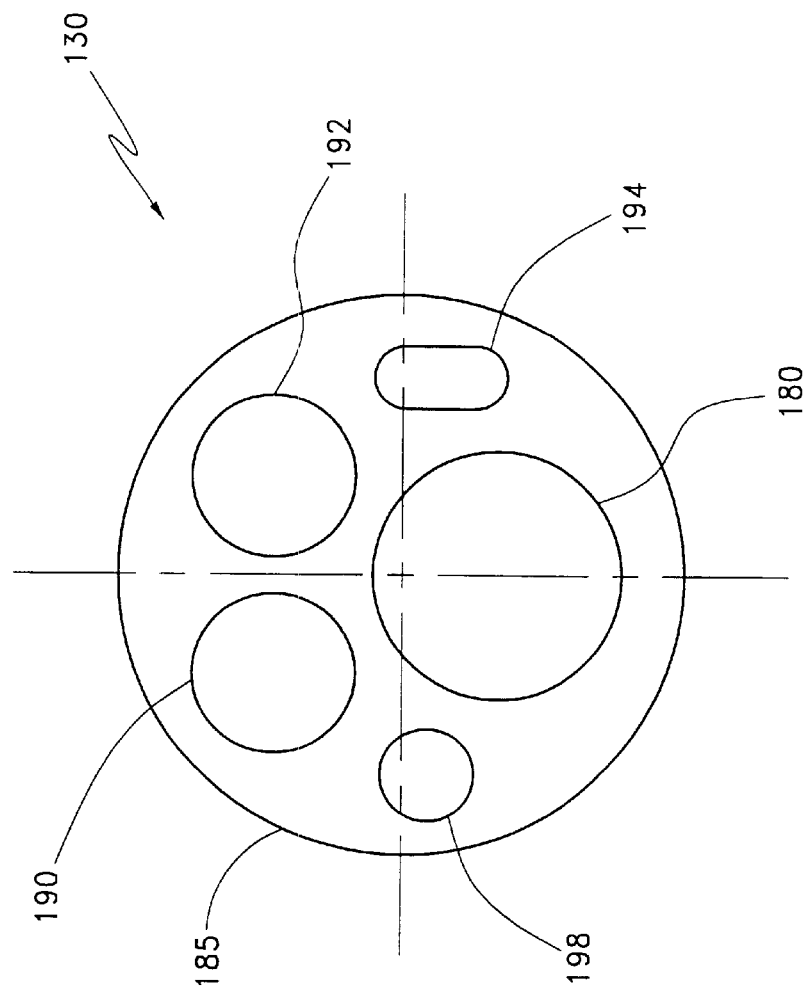
FIG. 23 is a cross-sectional view taken along line 23—23 of the circumferential ablation probe shown in FIG. 20.

The surgical ablation probe 100 also preferably includes sensor leads 148, a power cable 150, preferably a coaxial cable, and actuation means 154 for deploying the expandable member 106. These components extend from the handle 120, through the lumens in the probe shaft 102, to the corresponding components of the probe disposed on the distal end 122. The proximal ends of the cables and lumens connect to corresponding connectors 153, 155 that extend from the proximal end of the probe handle 120. The probe shaft 102 desirably includes a plurality of lumens (examples of which are illustrated in FIGS. 22–23). Various wires and electrical leads are routed to the distal end portion 122 through at least some of these lumens. In a preferred device, these lumens generally run the length of the shaft 102; however, for some applications, the lumens can be shorter.

The shaft 102 of the surgical ablation probe 100 is preferably formed with a distal port 158 located distal to the ablation member 104 and a proximal port 160 located proximal of the ablation member 104. The distal port 158 allows the clinician to introduce fluids into the patient, take fluid samples from the patient, and take fluid pressure reading on the distal side of the ablation member 104. Similarly, the proximal port 160 allows the clinician to introduce fluids into the patient, take fluid samples from the patient, and take fluid pressure reading on the proximal side of the ablation member 104. These ports and lumens are particularly useful when pressure or X-ray positioning techniques are employed, as explained below; however, the probe assembly 100 need not include such ports and lumens, such as when only an A-mode or Doppler position monitoring system is used with the probe assembly.

The probe is primarily designed for use during transthoracic (open heart) or minimally invasive cardiac surgery and can be used to form a conduction block during the same surgery in which another procedure is being performed, e.g., when repairing or replacing a mitral valve. For example, the physician may insert the probe through a chest access device, e.g., a trocar, or through an incision during open chest surgery. As illustrated in FIG. 5, the probe shaft 102 is introduced into an atrium through an atriotomy 10 in the left atrial appendage, and is then placed at a location where a pulmonary vein extends from the posterior atrial wall. Referring again to FIG. 19, the expandable member 106 is then expanded from its collapsed to its expanded state, (e.g., by inflation of a balloon by injection of inflation fluid). Once the expandable member 106 is positioned, in some cases engaged with, along the circumferential region of tissue, the physician actuates the ablation element 108 to ablate the region of tissue. During open chest surgery, the short, rigid, and adjustable nature of the probe shaft 102 and handle make placement and ablation more efficient and precise than with a translumenal catheter-based apparatus.

It should be noted that an open-heart procedure would require cardiopulmonary bypass wherein the patient's blood is diverted and oxygenated by an extracorporeal device. In this case, the atrium and pulmonary vein region will be devoid of blood, flushed clear by saline. This would allow a relatively clear field of view in which to operate. It may be desirable for the entire atrium to be flooded with saline, such that the balloon is engulfed in fluid while inflated. This may help avoid a "dry interface" between the balloon and the tissue to be ablated; such a "dry interface" could be an impediment to ultrasound energy conduction into the tissue because ultrasound energy is substantially reflected by even a thin layer of air.

Minimally invasive surgical procedures can be performed in similar fashion, i.e. with cardiopulmonary bypass. On the other hand, minimally invasive cardiac procedures are often done on a "beating heart", in which case blood flows normally through the cardiopulmonary system. In this case, the probe would be used in an environment identical to that of the percutaneous translumenal catheter (i.e. with normal pulmonary vein/atrial blood flow). In such cases, it may be necessary to have a separate visualization system employed to aid placement of the ablation probe, such as an endoscopic camera, intracardiac ultrasound probe, or fluoroscopic x-ray machine. It may also be desirable to include a perfusion lumen (not shown) that extends between ports located proximal and distal to the expandable member. Passive perfusion during expansion of the expandable member is believed to minimize stasis and allow the target pulmonary vein to continue in its atrial filling function during the atrial arrythmia treatement procedure. Without this perfusion feature, the expandable member blocks the flow of blood from the vein to the atrium and may result in undesirable thrombogenesis in the pulmonary vein distal to the expandable member.

Figure 21:
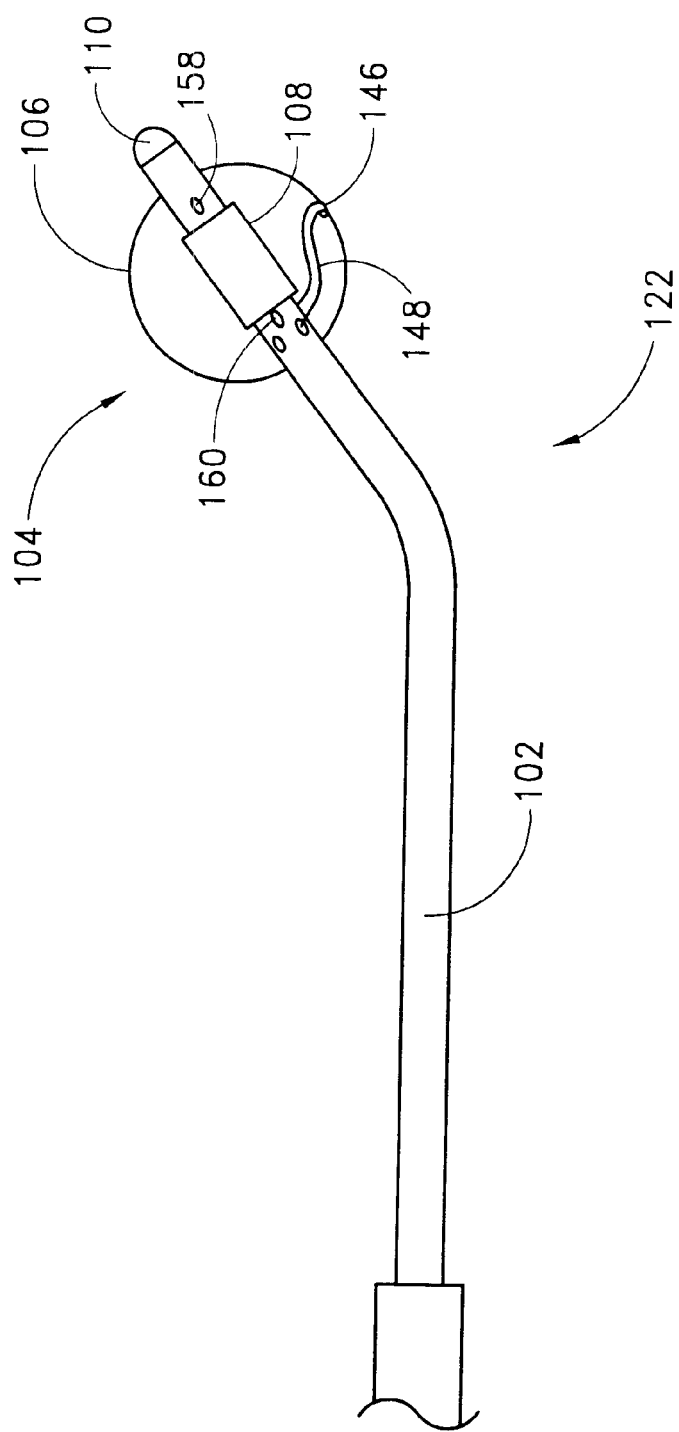
FIG. 21 shows the distal end portion of the circumferential ablation probe of FIG. 19 wherein the inflatable balloon is in an inflated state.

FIG. 21 illustrates an enlarged view of the distal end 122 of the probe shaft 102. The distal end 122 comprises a circumferential ablation member 104 having an expandable member 106 and an ablation element 108 (shown here as an ultrasound transducer). The expandable member 106 may be provided with one or more sensors 146 (e.g., temperature sensors or electrodes) on the exterior portion thereof for providing feedback to the physician during the ablation procedure.

The distal end 122 of the shaft 102 is preferably shaped to facilitate placement initially into the atrium and then into a pulmonary vein ostium. For example, the distal end may be angled to an angle of about 45°. The shaft 102 may have a length ranging from about 20 to about 60 cm. These lengths and angles, however, only exemplify one preferred form of the ablation probe 100 that has been found useful for a specific surgical procedure, and other lengths and shapes of the probe are also intended to be within the scope of this invention. In one variation, the shaft 102 may be shaped, by the physician manipulating the shaft, so that the shaft takes on a desired shape. In another variation, the probe may have a deflectable distal end which can be deflected by manipulation of a pull-wire system, as described in further detail below.

It is also understood that the probe shaft 102 can be configured for following different access paths into the atrium, such as, for example, but without limitation, via a retrograde procedure through the mitral valve, transeptally from a right atriotomy, or through a left atriotomy. The probe shaft 102 may be made of Pebax or any other materials that provide adjustable shape, flexibility, and maneuverability of the probe. Other materials include for example, stainless steel, Nitinol, thermoplastic braided material, polyamide braided tubing, etc.

Figure 20:
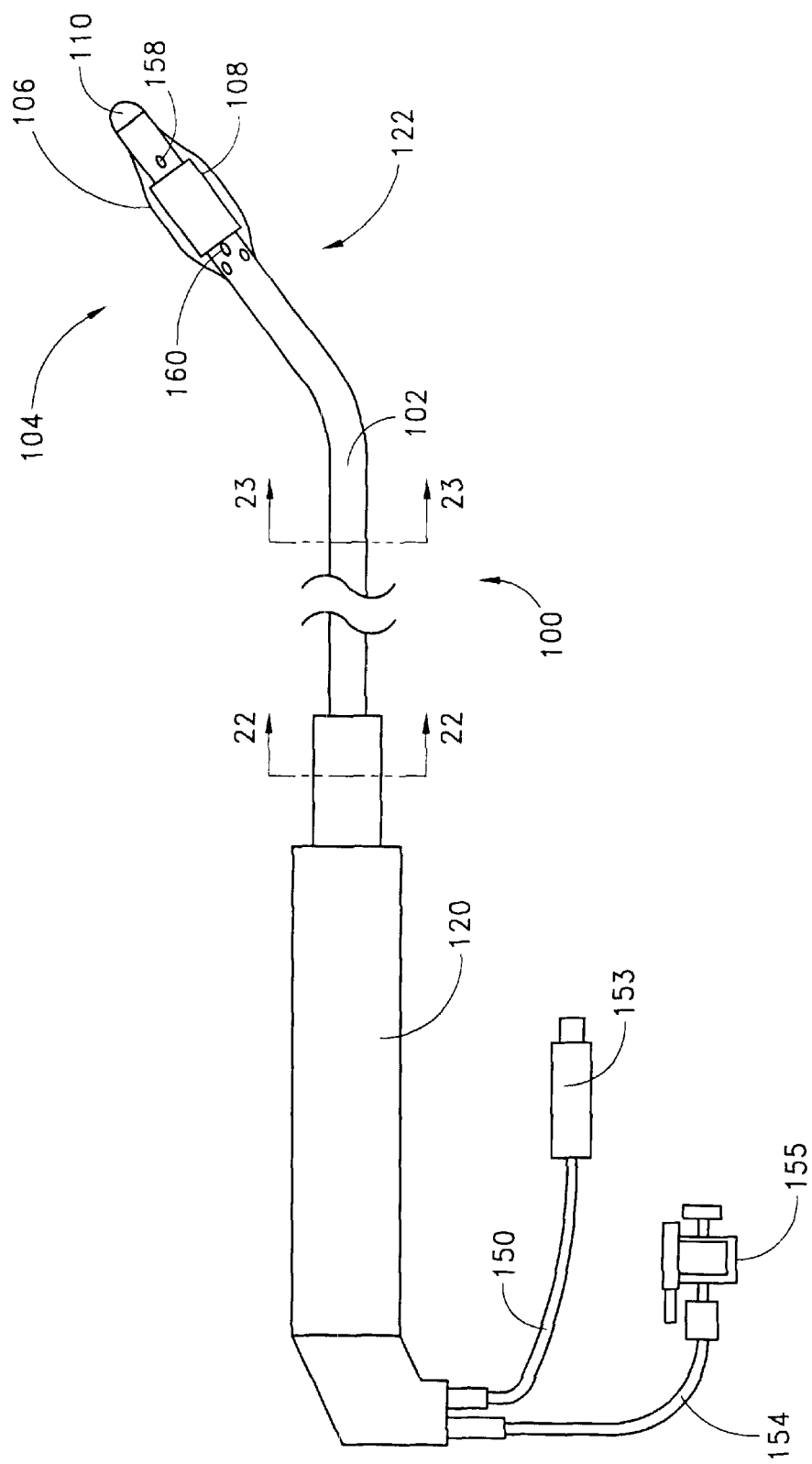
FIG. 20 shows the circumferential ablation probe of FIG. 19 wherein the inflatable balloon is in a collapsed state.

FIG. 20 shows the circumferential ablation probe 100 with the expandable member 106 in a radially collapsed condition. In this configuration, the ablation probe 100 is adapted for delivery into the pulmonary vein according to positioning step (3) of FIG. 3. The expandable member 106 is adjustable to a radially expanded position when actuated by an expansion actuator 154. In a preferred embodiment, the expansion actuator 154 comprises a pressurizeable fluid source.

With reference to FIG. 22, there is shown a cross-sectional view of the probe shaft 102 taken along line 22—22 of the circumferential ablation probe shown in FIG. 20. An outer extrusion 180 formed of a thin-walled, resilient tubing defining the outer surface of the probe shaft 102. The outer extrusion 180 may be formed of any of the biocompatible resilient plastics typically used in catheters, with polyimide and polyurethane available under the trade name PEBAX (from Atochem of Glen Rock, N.J.) being preferred materials.

Disposed within the outer extrusion 180, and radially outside of the inner probe surface 182 is an intermediate layer 184, which is adapted to transmit torque along the probe shaft 102 so that a physician can turn the probe distal end portion 152 by suitable manipulation of the handle 120. A preferred torque-transmitting material for the intermediate layer 184 is a metal braid formed of interleaved lengths of stainless steel encapsulated within the resilient plastic outer extrusion 180.

As illustrated in FIG. 22, several lumens may be disposed within the probe shaft 102, including, for example, a deflecting wire lumen 198, a coaxial cable lumen 192, a perfusion lumen 196, and a thermocouple leads lumen 194. When an inflatable balloon is used as an expandable member, the probe shaft 102 also includes an inflation lumen 190. The inflation lumen 190 preferably has an inner diameter of about 0.020 inch in order to allow for rapid deflation times, although this may vary based upon the viscosity of inflation medium used, length of the lumen 190, and other dynamic factors relating to fluid flow and pressure.

With reference to FIG. 23, there is shown a cross-sectional view of the probe shaft 102 taken along line 23—23 of the circumferential ablation probe shown in FIG. 20. The same lumens are present within the shaft 102 as described with reference to the proximal region shown in FIG. 22, however, the intermediate, torque-transmitting braid (184 in FIG. 22) is not present within the outer extrusion (180 in FIG. 22). Moreover, the outer extrusion itself is thinner, to reduce the stiffness of the distal end portion 152. Thus, for illustrative purposes, because of the relative thinness of the shaft wall 185 in the distal region, the wall (inner and outer surfaces) is labeled using a single reference numeral 185.

Figure 24:
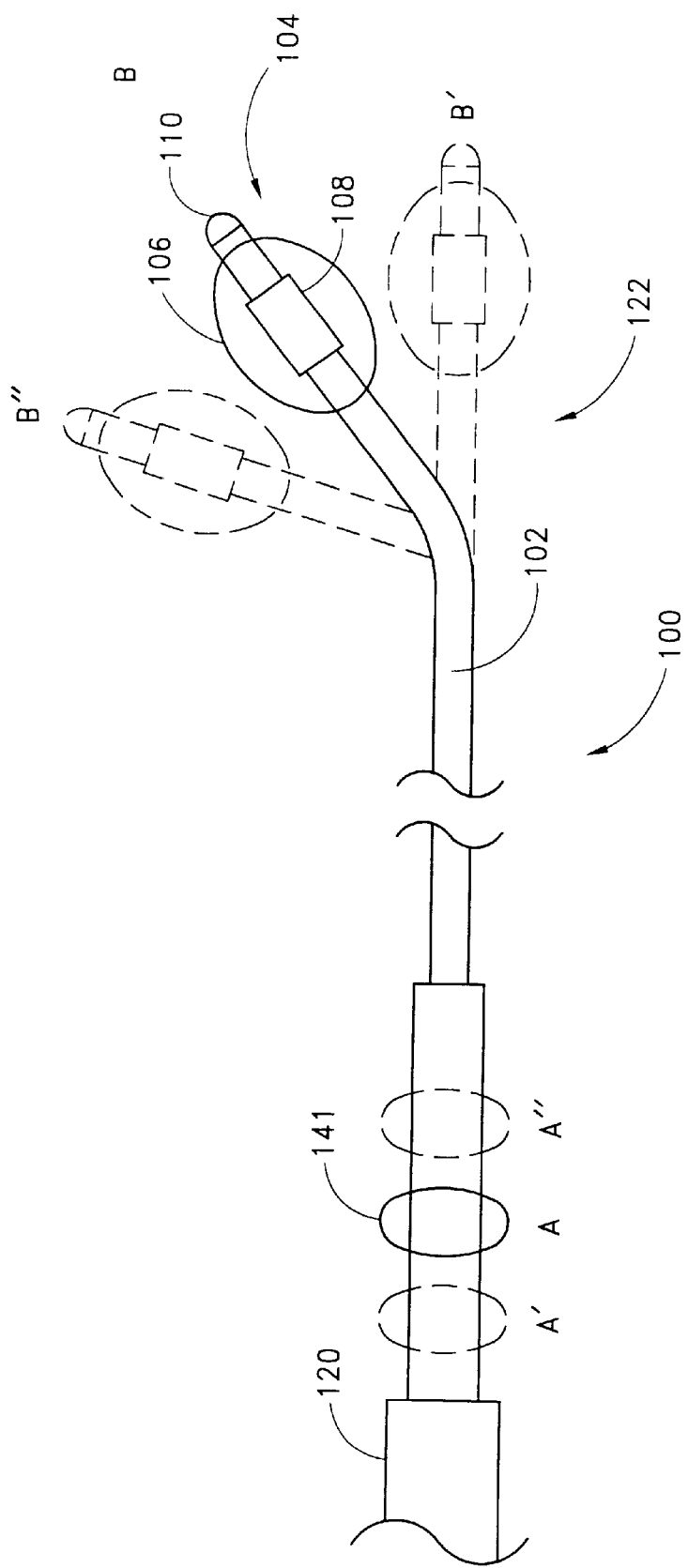
FIG. 24 is a perspective view of a circumferential ablation probe having a deflectable tip portion whereby the distal end is shown in various deflected positions.

Referring now to FIG. 24, a preferred embodiment of the surgical ablation probe 100 further comprises a deflectable tip design to independently select a desired pulmonary vein and direct the transducer assembly toward the desired location. Further to the deflectable variation, a deflecting pull wire is incorporated into the probe shaft 102. The pull wire is attached to the atraumatic tip 110 of the shaft 102, slidably engaged within a pull-wire lumen (198 in FIGS. 22 and 23) in the shaft 102, and attached to a deflection mechanism within the handle 120. The pull wire is adapted to deflect the distal probe tip by applying tension along varied stiffness transitions along the probe's length. Still further to this pull wire variation, acceptable pull wires may have a diameter within the range from about 0.008 inch to about 0.020 inch, and may further include a taper, such as, for example, a tapered outer diameter from about 0.020 inch to about 0.008 inch.

Still referring to FIG. 24, deflection of the distal end 122 of the ablation probe 100 is preferably produced by manipulation of a thumb slide 141 located on the handle 120. When the thumb slide 141 is moved from position A to position A' (drawn in phantom), the distal end portion 122 of probe shaft 102 is deflected from position B (zero deflection) to position B'. Likewise, when the thumb slide 141 is moved from position A to position A" (drawn in phantom), the distal end portion 122 of the shaft 102 is deflected from position B (zero deflection) to position B". Although, a variety of deflection handles are known in the art, they generally operate like the BIOSENSE/WEBSTER handles by placing tension on the proximal end of a pull wire which is slidably engaged within the probe shaft and fixed to the distal end portion.

Figure 25:
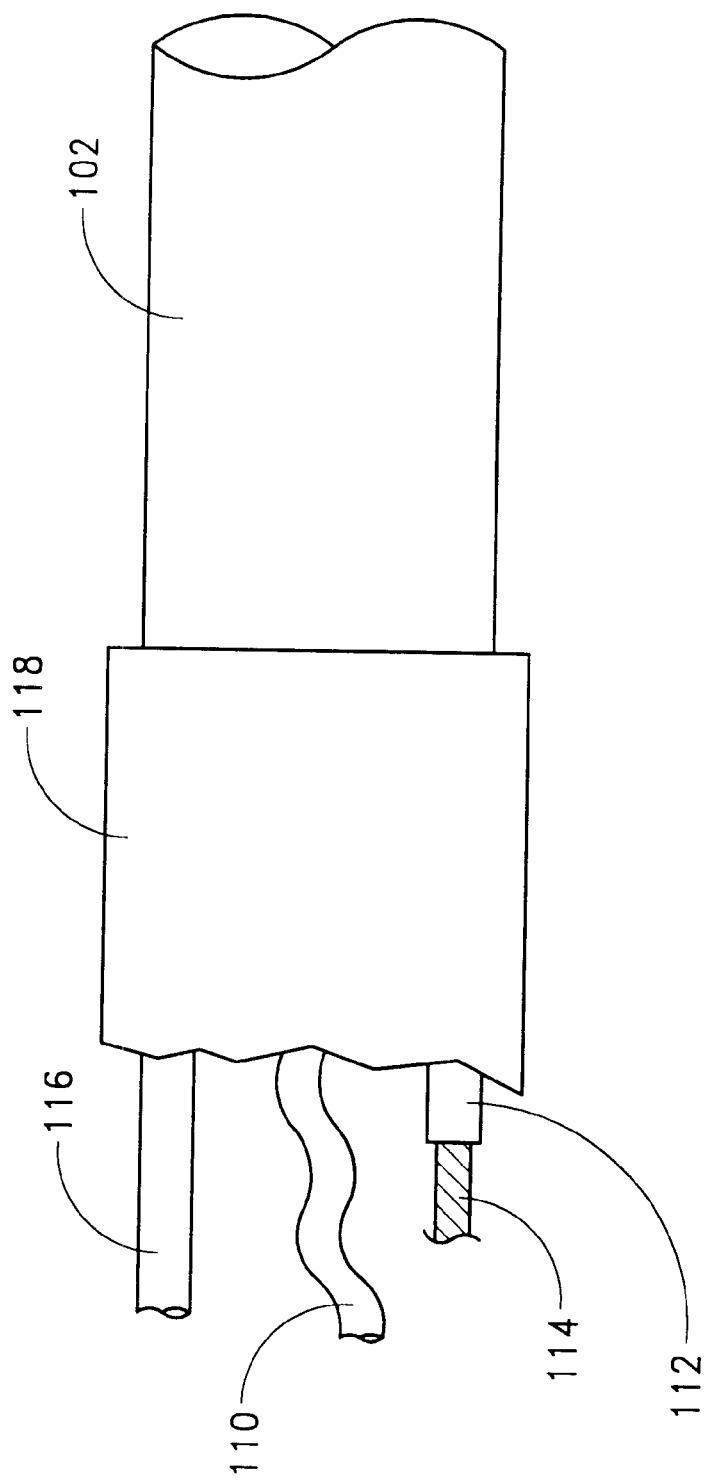
FIG. 25 is a schematic view of the proximal end of a circumferential ablation probe of FIG. 19, showing proximal extensions of the various lumens in the multilumen probe shaft.

FIG. 25 illustrates an expanded schematic view of one preferred embodiment of the proximal end portion of the probe shaft. It is understood, however, that any other extensions and modifications within the skill of those in the art are encompassed within the scope of the present disclosure. Here, surrounding the proximal end of the probe shaft 102 is a shrink-wrap layer 118, formed from ⅛ inch plastic shrink-wrap, such as for example PET. The inflation lumen is preferably extended about 16.5 cm using a hypotube 116, preferably of 0.042"/0.035". The coaxial cable 110 extends about 16 cm proximally from the proximal end portion 126. A 0.008" PTFE-coated mandrel was used for the deflecting pull wire 114, which is shown slidably engaged in a 0.026"/0.013" Teflon tube 112. The Teflon tubing 112 extends only about 1 cm past the proximal end portion and the pull wire 114 extends about 4 cm beyond the proximal end portion, where it connects to the handle (not shown).

Referring again to FIG. 19, the circumferential ablation member 104 of the probe 100 will be discussed in further detail. The expandable member 106 of ablation probe 100 preferably comprises a compliant elastomeric balloon or a non-compliant balloon made from silicone, latex, rubber, and polyvinylchloride, with an expandable diameter of between about 10 and about 40 mm. The probe shaft 102 includes an inflation lumen that communicates with the interior of the balloon, and the handle includes a balloon inflation/deflation port. The port is coupled to a source of pressurized inflation medium in a known manner to inflate the balloon.

The ablation element 108 is disposed on the distal tip 122 and cooperates with the expandable member 106 such that the ablation element 108 is held in a generally fixed position relative to the target circumferential region of tissue. In the preferred embodiment, the ablation element 108 is an ultrasound transducer adapted to emit ultrasonic sound waves sufficient to ablate a circumferential region of tissue when coupled to a suitable excitation source. It is believed that driving the ultrasonic transducer at 20 acoustical watts at an operating frequency within the range of 7–10 megahertz will form a sufficiently sized circumferential lesion about the pulmonary vein ostium in a relatively short period of time (e.g., 1 to 2 minutes or less).

The ablation element can be located outside or inside the expandable member, or can be located at least partially outside the expandable member. The ablation element, in some forms, also includes a portion of the expandable member. The preferred embodiment illustrated in FIG. 19 shows the ultrasonic transducer 108 located within the expandable member 106. Electrical leads extend through lumens in the probe shaft 102 and connect to one or more electrical connectors that extend from the probe handle.

It is also contemplated that the control level of energy can be delivered, then tested for lesion formation with a test stimulus in the pulmonary vein, either from an electrode provided at the tip area of the probe or on a separate device. Therefore, the procedure may involve ablation at a first energy level in time, then check for the effective conductive block provided by the resulting lesion, and then subsequent ablations and testing until a complete conductive block is formed.

In addition to the particular embodiment just described, the ultrasonic ablation element and expandable member located at the distal end 122 of the probe shaft 102 can take a variety of other configurations. With regard to the inflatable balloon 106 shown in FIG. 19, a central region is generally coaxially disposed over the probe shaft and is bordered at its end neck regions by proximal and distal adaptions. The proximal adaption is sealed over the elongate body proximally of the distal inflation and the electrical lead ports and the distal adaption is sealed over the probe shaft proximal of the distal tip. According to this arrangement, a fluid tight interior chamber is formed within the inflatable balloon 106. This interior chamber is fluidly coupled to a pressurizeable fluid source via the inflation lumen within the probe shaft. In addition to the inflation lumen, the electrical lead lumen also communicates with the interior chamber of expandable balloon so that the ultrasound transducer, which is positioned within that chamber and over the shaft, may be electrically coupled to the ultrasound drive source or actuator.

The inflatable balloon 106 may be constructed from a variety of known materials, although the balloon preferably is adapted to conform to the contour of a pulmonary vein ostium. For this purpose, the balloon material can be of the highly compliant variety or of a predefined shape. Because the probe is not restricted in profile as is a percutaneous translumenal catheter, the balloon can have a significantly larger collapsed profile than the shaft diameter. This allows greater latitude in the possible balloon configurations and expanded diameter, including non-compliant balloons, complex shaped balloons, balloons with dramatic surface features such as bumps or ridges, and non-balloon expandable members. These features may allow treatment of veins with large diameter or difficult shape that are not conducive to the limitations of a percutaneous translumenal catheter design.

The designs for an expandable member and circumferential ablation element for use in a circumferential ablation device assembly have been described generically with reference to the embodiments shown in the previous figures. Examples of more specific expandable member and ablation element embodiments which are adapted for use in such ablation device assemblies are further provided as follows.

Notwithstanding their somewhat schematic detail, the circumferential ablation members shown in the previous figures illustrate one particular embodiment wherein a circumferential electrode element circumscribes an outer surface of an expandable member. The expandable member of the embodiments shown may take one of several different forms, although the expandable member is generally herein shown as an inflatable balloon that is coupled to an expansion actuator 154 and wherein the expansion actuator 154 comprises a pressurizeable fluid source. The balloon is preferably made of a polymeric material and forms a fluid chamber which communicates with a fluid passageway (not shown in the figures) that extends proximally along the elongate probe body and terminates proximally in a proximal fluid port that is adapted to couple to the pressurizeable fluid source.

In one expandable balloon variation, the balloon is constructed of relatively inelastic plastics (e.g., polymers or monomers) such as a polyethylene ("PE"; preferably linear low density or high density or blends thereof), polyolefin copolymer ("POC"), polyethylene terephthalate ("PET"), polyimide, or a nylon material. In this construction, the balloon has a low radial yield or compliance over a working range of pressures and may be folded into a predetermined configuration when deflated in order to facilitate introduction of the balloon into the desired ablation location. In this variation, one balloon size may not suitably engage all pulmonary vein walls for performing the circumferential ablation methods herein described on all needy patients. Therefore, it is further contemplated that a kit of multiple ablation probes, with each balloon working length having a unique predetermined expanded diameter, may be provided from which a treating physician may chose a particular device to meet a particular patient's pulmonary vein anatomy.

In an alternative expandable balloon variation, the balloon is constructed of a relatively compliant, elastomeric material, such as, for example (but not limited to), a silicone, latex, polyurethane, or mylar elastomer. In this construction, the balloon takes the form of a tubular member in the deflated, non-expanded state. When the elastic tubular balloon is pressurized with fluid such as in the previous, relatively non-compliant example, the material forming the wall of the tubular member elastically deforms and stretches radially to a predetermined diameter for a given inflation pressure. It is further contemplated that the compliant balloon may be constructed as a composite, such as, for example, a latex or silicone balloon skin which includes fibers, such as metal, Kevlar, or nylon fibers, which are embedded into the skin. Such fibers, when provided in a predetermined pattern such as a mesh or braid, may provide a controlled compliance along a preferred axis, preferably limiting longitudinal compliance of the expandable member while allowing for radial compliance.

It is believed that, among other features, the relatively compliant variation may provide a wide range of working diameters, which may allow for a wide variety of patients, or of vessels within a single patient, to be treated with just one or a few devices. Furthermore, this range of diameters is achievable over a relatively low range of pressures, which is believed to diminish a potentially traumatic vessel response that may otherwise be presented concomitant with higher pressure inflations, particularly when the inflated balloon is oversized to the vessel. In addition, the low-pressure inflation feature of this variation is suitable because the functional requirement of the expandable balloon is merely to engage the ablation element against a circumferential path along the inner lining of the pulmonary vein wall.

Moreover, a circumferential ablation member is adapted to conform to the geometry of the pulmonary vein ostium, at least in part by providing substantial compliance to the expandable member, as was shown and described previously by reference to FIGS. 10–11. Further to this conformability to pulmonary vein ostium as provided in the specific design of FIG. 10, the working length L of expandable member 306 is also shown to include a taper which has a distally reducing outer diameter from a proximal end to a distal end. In either a compliant or the non-compliant balloon, such a distally reducing tapered geometry adapts the circumferential ablation element to conform to the funneling geometry of the pulmonary veins in the region of their ostia in order to facilitate the formation of a circumferential conduction block there.

The circumferential ablation probe of the present invention preferably comprises an ultrasound ablation element for ablating the surrounding tissue. However, the circumferential ablation probe may be used with a wide variety of ablation elements. For example, in another preferred embodiment, the outer surface of the expandable member includes one or more electrode bands adapted to ablatively couple to the surrounding tissue to form circumferential lesions. The electrode bands are energized by an ablation actuator that generally includes a radio-frequency ("RF") current source (not shown) coupled to both the RF electrode element and also a ground patch 195 which is in skin contact with the patient to complete an RF circuit. In addition, the ablation actuator preferably includes a monitoring circuit (not shown) and a control circuit (not shown) which together use either the electrical parameters of the RF circuit or tissue parameters such as temperature in a feedback control loop to drive current through the electrode element during ablation. Also, where a plurality of ablation elements or electrodes in one ablation element are used, a switching means may be used to multiplex the RF current source between the various elements or electrodes.

Figure 26A:
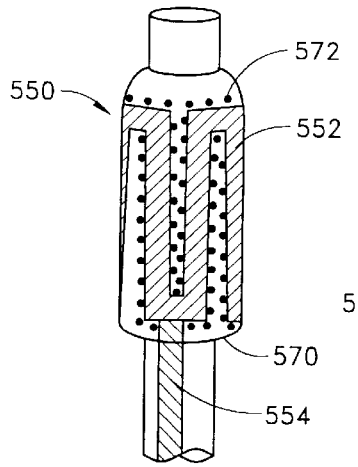
FIGS. 26A–B show perspective views of another circumferential ablation member variation for use in a circumferential ablation device assembly for pulmonary vein isolation, showing a circumferential ablation electrode circumscribing the working length of an expandable member with a secondary shape along the longitudinal axis of the working length which is a modified step shape, the expandable member being shown in a radially collapsed position and also in a radially expanded position, respectively.
Figure 26B:
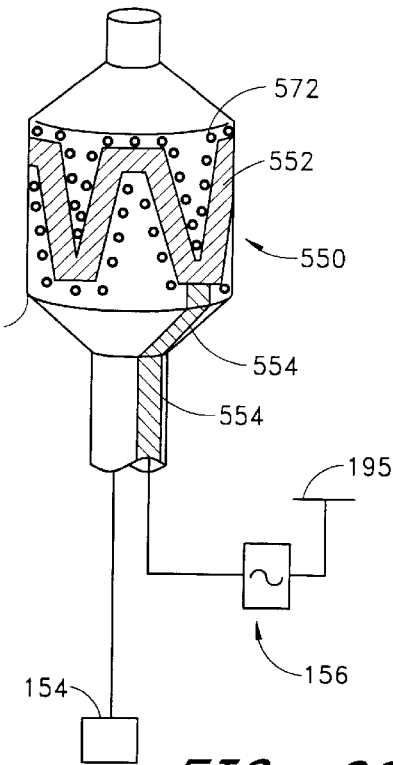

FIGS. 26A–D show various patterns of electrically conductive, circumferential electrode bands used as electrode ablation elements, each circumscribing an outer surface of the working length of an expandable member. FIGS. 26A–B show circumferential ablation member 550 to include a continuous circumferential electrode band 552 that circumscribes an outer surface of an expandable member 570. FIG. 26B more specifically shows expandable member 570 as a balloon which is fluidly coupled to a pressurizeable fluid source), and further shows electrode band (circumferential ablation element) 552 electrically coupled via electrically conductive lead 554 to ablation actuator 156. In addition, a plurality of apertures 572 is shown in the balloon skin wall of expandable member 570 adjacent to electrode band 552. The purpose of these apertures 572 is to provide a positive flow of fluid such as saline or ringers lactate fluid into the tissue surrounding the electrode band 552. Such fluid flow is believed to reduce the temperature rise in the tissue surrounding the electrode element during RF ablation.

The shapes shown collectively in FIGS. 26A–D allow for a continuous electrode band to circumscribe an expandable member's working length over a range of expanded diameters, a feature which is believed to be particularly useful with a relatively compliant balloon as the expandable member. In the particular embodiments of FIGS. 26A–D, this feature is provided primarily by a secondary shape given to the electrode band relative to the longitudinal axis of the working length of the expandable member. Electrode band 552 is thus shown in FIGS. 26A–B to take the specific secondary shape of a modified step curve. Other shapes than a modified step curve are also suitable, such as the serpentine or sawtooth secondary shapes shown respectively in FIGS. 26C–D. Other shapes in addition to those shown in FIGS. 26A–D and which meet the defined functional requirements are further contemplated.

Figure 26C:
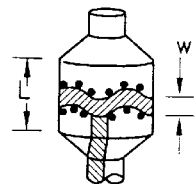
FIGS. 26C–D show perspective views of two circumferential ablation electrodes which form equatorial or otherwise circumferentially placed bands that circumscribe the working length of an expandable member and that have serpentine and sawtooth secondary shapes, respectively, relative to the longitudinal axis of the expandable member when adjusted to a radially expanded position.
Figure 26D:
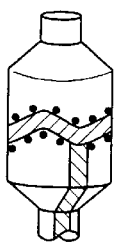

In addition, the electrode band provided by the circumferential ablation elements shown in FIGS. 26C–D has a functional band width w relative to the longitudinal axis of the working length which is only required to be sufficiently wide to form a complete conduction block against conduction along the walls of the pulmonary vein in directions parallel to the longitudinal axis. In contrast, the working length L of the respective expandable element is adapted to securely anchor the distal end portion in place such that the ablation element is firmly positioned at a selected region of the pulmonary vein for ablation. Accordingly, the band width w is relatively narrow compared to the working length L of the expandable element, and the electrode band may thus form a relatively narrow equatorial band which has a band width that is less than two-thirds or even one-half of the working length of the expandable element. Additionally, it is to be noted here and elsewhere throughout the specification, that a narrow band may be placed at locations other than the equator of the expandable element, preferably as long as the band is bordered on both sides by a portion of the working length L.

In another aspect of the narrow equatorial band variation for the circumferential ablation element, the circumferential lesion formed may also be relatively narrow when compared to its own circumference, and may be less than two-thirds or even one-half its own circumference on the expandable element when expanded. In one arrangement which is believed to be suitable for ablating circumferential lesions in the pulmonary veins as conduction blocks, the band width w is less than 1 cm with a circumference on the working length when expanded that is greater than 1.5 cm.

Figure 26E:
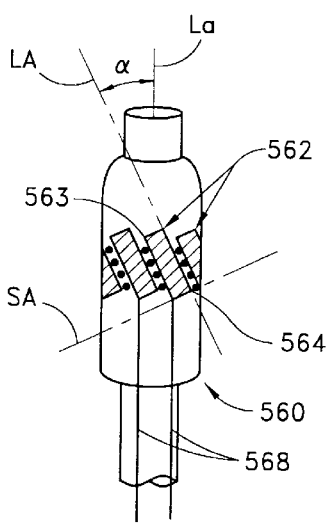
FIGS. 26E–F show perspective views of another circumferential ablation element which includes a plurality of individual ablation electrodes that are spaced circumferentially to form an equatorial band which circumscribes the working length of an expandable member either in an equatorial location or an otherwise circumferential location that is bounded both proximally and distally by the working length, and which are adapted to form a continuous circumferential lesion while the working length is adjusted to a radially expanded position.
Figure 26F:
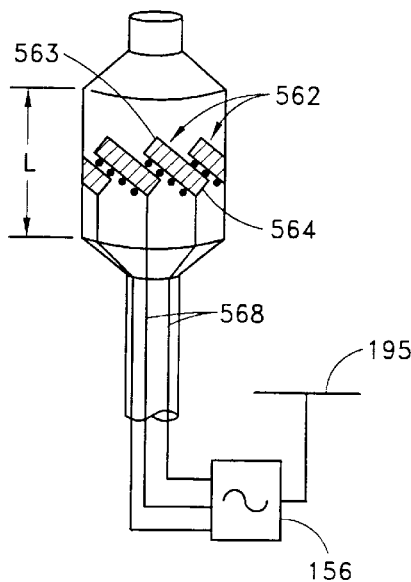

FIGS. 26E–F show a further variation of a circumferential ablation element which is adapted to maintain a continuous circumferential lesion pattern over a range of expanded diameters and which includes electrode elements that form a relatively narrow equatorial band around the working length of an expandable balloon member. In this variation, a plurality of individual electrode/ablation elements 562 are included in the circumferential ablation element and are positioned in spaced arrangement along an equatorial band which circumscribes an outer surface of the expandable member's working length L.

The size and spacing between these individual electrode elements 562, when the balloon is expanded, is adapted to form a substantially continuous circumferential lesion in pulmonary vein wall tissue when in intimal contact adjacent thereto, and is further adapted to form such a lesion over a range of band diameters as the working length is adjusted between a variety of radially expanded positions. Each individual electrode element 562 has two opposite ends 563, 564, respectively, along a long axis LA and also has a short axis SA, and is positioned such that the long axis LA is at an acute angle relative to the longitudinal axis LA of the elongate probe body and expandable member 560. At least one of the ends 563, 564 along the long axis LA overlaps with an end of another adjacent individual electrode element, such that there is a region of overlap along their circumferential aspect, i.e., there is a region of overlap along the circumferential coordinates. The terms "region of overlap along their circumferential coordinate" are herein intended to mean that the two adjacent ends each are positioned along the working length with a circumferential and also a longitudinal coordinate, wherein they share a common circumferential coordinate. In this arrangement, the circumferential compliance along the working length, which accompanies radial expansion of the expandable member also, moves the individual electrode elements apart along the circumferential axis. However, the spaced, overlapping arrangement described allows the individual ablation elements to maintain a certain degree of their circumferential overlap, or at least remain close enough together, such that a continuous lesion may be formed without gaps between the elements.

The construction for suitable circumferential electrode elements in the RF variations herein described, such as the various electrode embodiments described with reference to FIGS. 26A–F, may comprise a metallic material deposited on the outer surface of the working length using conventional techniques, such as by plasma depositing, sputter coating, chemical vapor deposition, other known techniques which are equivalent for this purpose, or otherwise affixing a metallic shaped member onto the outer surface of the expandable member such as through known adhesive bonding techniques. Other RF electrode arrangements are also considered, so long as they form a circumferential conduction block as previously described. For example, a balloon skin may itself be metallized, such as by mixing conductive metal, including but not limited to gold, platinum, or silver, with a plastic (e.g., polymer) to form a compounded, conductive matrix as the balloon skin.

Still further to the RF electrode embodiments, another circumferential ablation member variation (not shown) may also include an expandable member, such as an inflatable balloon, that includes a porous skin that is adapted to allow fluid, such as hypertonic saline solution, to pass from an internal chamber defined by the skin and outwardly into surrounding tissues. Such a porous skin may be constructed according to several different methods, such as by forming holes in an otherwise contiguous plastic (e.g., polymeric) material, including mechanically drilling or using laser energy, or the porous skin may simply be an inherently porous membrane. In any case, by electrically coupling the fluid within the porous balloon skin to an RF current source (preferably monopolar), the porous region of the expandable member serves as an RF electrode wherein RF current flows outwardly through the pores via the conductive fluid. In addition, it is further contemplated that a porous outer skin may be provided externally of another, separate expandable member, such as a separate expandable balloon, wherein the conductive fluid is contained in a region between the porous outer skin and the expandable member contained therein. Various other "fluid electrode" designs than those specifically herein described may also be suitable according to one of ordinary skill upon review of this disclosure.

In the alternative, or in addition to the RF electrode variations just described, the circumferential ablation element may also include other ablative energy sources or sinks, and particularly may include a thermal conductor that circumscribes the outer circumference of the working length of an expandable member. Examples of suitable thermal conductor arrangements include a metallic element which may, for example, be constructed as previously described for the more detailed RF embodiments above. However, in the thermal conductor embodiment such a metallic element would be generally either resistively heated in a closed loop circuit internal to the probe, or conductively heated by a heat source coupled to the thermal conductor. In the latter case of conductive heating of the thermal conductor with a heat source, the expandable member may be, for example, a plastic (e.g., polymeric) balloon skin which is inflated with a fluid that is heated either by a resistive coil or by bipolar RF current. In any case, it is believed that a thermal conductor on the outer surface of the expandable member is suitable when it is adapted to heat tissue adjacent thereto to a temperature between 40° and 80° Celsius.

Further to the thermal conduction variation for the circumferential ablation element, a perfusion balloon embodiment may be particularly useful in such a design. It is believed that ablation through increased temperatures, as provided by example above may also enhance coagulation of blood in the pulmonary vein adjacent to the expandable member, which blood would otherwise remain stagnant without such a perfusion feature.

One further circumferential ablation element design which is believed to be highly useful in performing the ablation methods herein described is shown in FIG. 27A to include a circumferential ablation member 600 with two insulators 602, 604 that encapsulate the proximal and distal ends, respectively, of the working length L of an expandable member 610. In the particular embodiment shown, the insulators 602, 604 are thermal insulators, such as a thermal insulator comprising a Teflon material. Expandable member 610 is an inflatable balloon which has a balloon skin 612 that is thermally conductive to surrounding tissue when inflated with a heated fluid which may contain a radiopaque agent, saline fluid, ringers lactate, combinations thereof, other known biocompatible fluids having acceptable heat transfer properties for these purposes, further to the thermal conductor embodiments previously described. By providing these spaced insulators, a circumferential ablation element is formed as an equatorial band 603 of uninsulated balloon skin is located between the opposite insulators. In this configuration, the circumferential ablation element is able to conduct heat externally of the balloon skin much more efficiently at the uninsulated equatorial band 603 than at the insulated portions, and thereby is adapted to ablate only a circumferential region of tissue in a pulmonary vein wall which is adjacent to the equatorial band. It is further noted that this embodiment is not limited to an "equatorial" placement of the ablation element. Rather, a circumferential band may be formed anywhere along the working length of the expandable member and circumscribing the longitudinal axis of the expandable member as previously described.

FIG. 27A further shows use of a radiopaque marker 620 to identify the location of the equatorial band 603 in order to facilitate placement of that band at a selected ablation region of a pulmonary vein via X-ray visualization. Radiopaque marker 620 is opaque under X-ray, and may be constructed, for example, of a radiopaque metal such as gold, platinum, or tungsten, or may comprise a radiopaque plastic (e.g., polymer) such as a metal loaded polymer. Such a radiopaque marker may also be combined with the other embodiments herein shown and described. To note, when the circumferential ablation member which forms an equatorial band includes a metallic electrode element, such electrode may itself be radiopaque and may not require use of a separate marker as just described.

The thermal insulator embodiment just described by reference to FIG. 27A is illustrative of a broader embodiment, wherein a circumferential ablation member has an ablating surface along the entire working length of an expandable member, but is shielded from releasing ablative energy into surrounding tissues except for along an unshielded or uninsulated equatorial band. As such, the insulator embodiment contemplates other ablation elements, such as the RF embodiments previously described above, which are provided along the entire working length of an expandable member and which are insulated at their ends to selectively ablate tissue only about an uninsulated equatorial band.

In a further example using the insulator embodiment in combination with a circumferential RF electrode embodiment, a metallized balloon which includes a conductive balloon skin may have an electrical insulator, such as a plastic (e.g., polymeric) coating, at each end of the working length and thereby selectively ablate tissue with electricity flowing through the uninsulated equatorial band. In this and other insulator embodiments, it is further contemplated that the insulators described may be only partial and still provide the equatorial band result. For instance, in the conductive RF electrode balloon case, a partial electrical insulator will allow a substantial component of current to flow through the uninsulated portion due to a "shorting" response to the lower resistance in that region.

In still a further example of an insulator combined with a RF ablation electrode, a porous membrane comprises the entire balloon skin of an expandable member. By insulating the proximal and distal end portions of the working length of the expandable member, only the pores in the unexposed equatorial band region are allowed to effuse the electrolyte which carries an ablative RF current.

Further to the expandable member design for use in a circumferential ablation member as herein described, other expandable members than a balloon are also considered suitable. For example, in one expandable cage embodiment shown in FIG. 27B, cage 650 comprises coordinating wires 651 and is expandable to engage a desired ablation region in a pulmonary vein.

The radial expansion of cage 650 is accomplished as follows. Sheath 652 is secured around the wires proximally of cage 650. However, core 653, which may be a metallic mandrel such as stainless steel, extends through sheath 652 and distally within cage 650 wherein it terminates in a distal tip 656. Wires 651 are secured to distal tip 656, for example, by soldering, welding, adhesive bonding, heat shrinking a plastic (e.g., polymeric) member over the wires, or any combination of these methods. Core 653 is slidable within sheath 652, and may, for example, be housed within a tubular lumen (not shown) within sheath 652, the wires being housed between a coaxial space between the tubular lumen and sheath 652. By moving the sheath 652 relative to core 653 and distal tip 656, the cage 650 is collapsible along its longitudinal axis in order to force an outward radial bias to wires 651 in an organized fashion to formed a working length of cage 650 which is expanded (not shown).

Further to the particular expandable cage embodiment shown in FIG. 27B, a plurality of ablation electrodes 655 is shown, each being positioned on one of wires 651 and being similarly located along the longitudinal axis of the cage 650. The radial bias given to wires 651 during expansion, together with the location of the ablation electrodes 655, serves to position the plurality of ablation electrodes/elements 655 along a circumferential, equatorial band along the expanded working length of cage 650. The wires forming a cage according to this embodiment may also have another predetermined shape when in the radially expanded position. For example, a taper similar to that shown for expandable member 106 in FIG. 19 may be formed by expanding cage 650, wherein the ablation element formed by ablation electrodes 655 may be positioned between the proximal end and the distal end of the taper.

Further to the construction of the embodiment shown in FIG. 27B, wires 651 are preferably metal, and may comprise stainless steel or a superelastic metal alloy, such as an alloy of nickel and titanium, or a combination of both. Regarding the case of nickel and titanium construction for wires 655, a separate electrical conductor may be required in order to actuate ablation electrodes 655 to efficiently emit ablative current into surrounding tissues. In the case where wires 651 are constructed of stainless steel, they may also serve as electrical conductors for ablation electrodes 655. Further to the stainless steel design, the wires 651 may be coated with an electrical insulator to isolate the electrical flow into surrounding tissues at the site of the ablation electrodes 655. Moreover, the ablation electrodes 655 in the stainless steel wire variation may be formed simply by removing electrical insulation in an isolated region to allow for current to flow into tissue only from that exposed region.

In a further cage embodiment (not shown) to that shown in FIG. 27B, a circumferential strip of electrodes may also be secured to the cage 650 such that the strip circumscribes the cage at a predetermined location along the cage's longitudinal axis. By expanding cage 650 as previously described, the strip of electrodes are adapted to take a circumferential shape according to the shape of the expanded cage 650. Such an electrode strip is preferably flexible, such that it may be easily reconfigured when the cage is adjusted between the radially collapsed and expanded positions and such that the strip may be easily advanced and withdrawn with the cage within the delivery sheath. Furthermore, the electrode strip may be a continuous circumferential electrode such as a conductive spring coil, or may be a flexible strip which includes several separate electrodes along its circumferential length. In the latter case, the flexible strip may electrically couple all of the electrodes to a conductive lead that interfaces with a drive circuit, or each electrode may be separately coupled to one or more such conductive leads.

Figure 28:
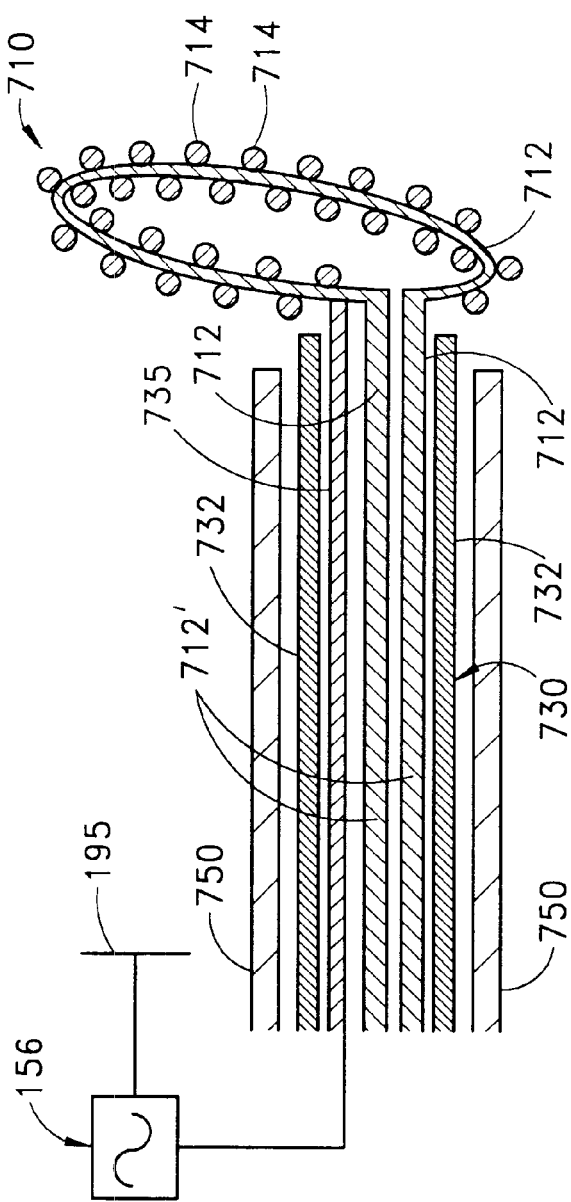
FIG. 28 shows a cross-sectional view of another circumferential ablation element which is adapted for use in a circumferential ablation device assembly for pulmonary vein isolation. A superelastic, looped electrode element is shown at the distal end of a pusher and is adapted to circumferentially engage pulmonary vein wall tissue to form a circumferential lesion as a conduction block that circumscribes the pulmonary vein lumen.

Another circumferential ablation element adapted for use in a circumferential conduction block assembly of the type herein described is shown in FIG. 28, wherein circumferential ablation member 700 includes a looped member 710 attached, preferably by heat shrinking, to a distal end of a pusher 730. Looped member 710 and pusher 730 are slidably engaged within delivery sheath 750 such that looped member 710 is in a first collapsed position when positioned and radially confined within delivery sheath 750, and expands to a second expanded position when advanced distally from delivery sheath 750.

Looped member 710 is shown in more detail in FIG. 28 to include a core 712 which is constructed of a superelastic metal alloy such as a nickel-titanium alloy and which has a looped portion with shape memory in the looped configuration. This looped configuration is shown in FIG. 28 to be in a plane which is off-axis, preferably perpendicular, to the longitudinal axis of the pusher 730. This off-axis orientation of the loop is adapted to engage a circumferential path of tissue along a pulmonary vein wall which circumscribes the pulmonary vein lumen when the looped member 710 is delivered from the delivery sheath 750 when the delivery sheath is positioned within the vein lumen parallel to its longitudinal axis. An ablation electrode 714 is also shown in FIG. 28 as a metallic coil which is wrapped around core 712 in its looped portion.

Pusher 730 is further shown in FIG. 28 to include a tubular pusher member 732 which is heat shrunk over two ends 712' of core 712 which extend proximally of looped member 710 through pusher 730 in the particular variation shown. While in this embodiment core 712 extends through the pusher in order to provide stiffness to the composite design for the pusher, it is further contemplated that the superelastic metal of the core may be replaced or augmented in the pusher region with another different mandrel or pusher core (not shown), such as a stiffer stainless steel mandrel. Also shown within pusher 730 is an electrically conductive lead 735 which is coupled to the ablation electrode 714 and which is also adapted in a proximal region of the pusher (not shown) to couple to an ablation actuator 156 such as an RF current source (shown schematically).

FIGS. 29A–31B show various specific embodiments of a broader circumferential ablation device assembly which utilizes an ultrasonic energy source to ablate tissue. The present circumferential ablation device has particular utility in connection with forming a circumferential lesion within or about a pulmonary vein ostium or within the vein itself in order to form a circumferential conductive block. This application of the present ablation device, however, is merely exemplary, and it is understood that those skilled in the art can readily adapt the present ablation device for applications in other body spaces.

As common to each of the following embodiments, a source of acoustic energy is provided for a delivery device that also includes an anchoring mechanism. In one mode, the anchoring mechanism comprises an expandable member that also positions the acoustic energy source within the body; however, other anchoring and positioning devices may also be used, such as, for example, a basket mechanism. In a more specific form, the acoustic energy source is located within the expandable member and the expandable member is adapted to engage a circumferential path of tissue either about or along a pulmonary vein in the region of its ostium along a left atrial wall. The acoustic energy source in turn is acoustically coupled to the wall of the expandable member and thus to the circumferential region of tissue engaged by the expandable member wall by emitting a circumferential and longitudinally collimated ultrasound signal when actuated by an acoustic energy driver. The use of acoustic energy, and particularly ultrasonic energy, offers the advantage of simultaneously applying a dose of energy sufficient to ablate a relatively large surface area within or near the heart to a desired heating depth without exposing the heart to a large amount of current. For example, a collimated ultrasonic transducer can form a lesion, which has about a 1.5 mm width, about a 2.5 mm diameter lumen, such as a pulmonary vein and of a sufficient depth to form an effective conductive block. It is believed that an effective conductive block can be formed by producing a lesion within the tissue that is transmural or substantially transmural. Depending upon the patient as well as the location within the pulmonary vein ostium, the lesion may have a depth of 1 millimeter to 10 millimeters. It has been observed that the collimated ultrasonic transducer can be powered to provide a lesion having these parameters so as to form an effective conductive block between the pulmonary vein and the posterior wall of the left atrium.

With specific reference now to the embodiment illustrated in FIGS. 29A through 29D, a circumferential ablation device assembly 800 includes a shaft 802 with proximal and distal end portions 810,812, an expandable balloon 820 located along the distal end portion 812 of elongate body 802, and a circumferential ultrasound transducer 830 which forms a circumferential ablation member which is acoustically coupled to the expandable balloon 820. In more detail, FIGS. 29A–C variously show shaft 802 to include inflation lumen 806 and electrical lead lumen 808.

Each lumen extends between a proximal port (not shown) and a respective distal port, which distal ports are shown as distal inflation port 807 for inflation lumen 806, and distal lead port 809 for electrical lead lumen 808. Although the inflation and electrical lead lumens are generally arranged in a side-by-side relationship, the elongate body 802 can be constructed with one or more of these lumens arranged in a coaxial relationship, or in any of a wide variety of configurations that will be readily apparent to one of ordinary skill in the art.

In addition, the shaft 802 is also shown in FIGS. 29A and 29C to include an inner member 803 which extends distally beyond distal inflation and lead ports 807, 809, through an interior chamber formed by the expandable balloon 820, and distally beyond expandable balloon 820 where the shaft terminates in a distal tip. The inner member 803 provides a support member for the cylindrical ultrasound transducer 830 and for the distal neck of the expansion balloon, as described in more detail below.

In addition to providing the requisite lumens and support members for the ultrasound transducer assembly, the shaft 802 of the present embodiment must also be adapted to be introduced into the left atrium such that the distal end portion with balloon and transducer may be placed within the pulmonary vein ostium. Therefore, the distal end portion 812 is preferably flexible. In one further more detailed construction which is believed to be suitable, the proximal end portion is adapted to be at least 30% more stiff than the distal end portion. According to this relationship, the proximal end portion may be suitably adapted to provide push transmission to the distal end portion while the distal end portion is suitably adapted to track through bending anatomy during in vivo delivery of the distal end portion of the device into the desired ablation region.

The body may also comprise a "pullwire" lumen and associated fixed pullwire which is adapted to deflect the probe tip by applying tension along varied stiffness transitions along the probe's length. Still further to this pullwire variation, acceptable pullwires may have a diameter in the range from about 0.008 inch to about 0.020 inch, and may further include a taper, such as, for example, a tapered outer diameter from about 0.020 inch to about 0.008 inch.

More specifically regarding expandable balloon 820 as shown in varied detail between FIGS. 29A and 29C, a central region 822 is generally coaxially disposed over the inner member 803 and is bordered at its end neck regions by proximal and distal adaptions 824, 826. The proximal adaption 824 is sealed over shaft 802 proximally of the distal inflation and the electrical lead ports 807,809, and the distal adaption 826 is sealed over inner member 803. According to this arrangement, a fluid tight interior chamber is formed within expandable balloon 820. This interior chamber is fluidly coupled to a pressurizeable fluid source (not shown) via inflation lumen 806. In addition to the inflation lumen 806, electrical lead lumen 808 also communicates with the interior chamber of expandable balloon 820 so that the ultrasound transducer 830, which is positioned within that chamber and over the inner member 803, may be electrically coupled to an ultrasound drive source or actuator, as will be provided in more detail below.

The expandable balloon 820 may be constructed from a variety of known materials, although the balloon 820 preferably is adapted to conform to the contour of a pulmonary vein ostium. For this purpose, the balloon material can be of the highly compliant variety, such that the material elongates upon application of pressure and takes on the shape of the body lumen or space when fully inflated. Suitable balloon materials include elastomers, such as, for example, but without limitation, Silicone, latex, or low durometer polyurethane (for example, a durometer of about 80A).

In addition or in the alternative to constructing the balloon of highly compliant material, the balloon 820 can be formed to have a predefined fully inflated shape (i.e., be preshaped) to generally match the anatomic shape of the body lumen in which the balloon is inflated. For instance, as described below in greater detail, the balloon can have a distally tapering shape to generally match the shape of a pulmonary vein ostium, and/or can include a bulbous proximal end to generally match a transition region of the atrium posterior wall adjacent to the pulmonary vein ostium. In this manner, the desired seating within the irregular geometry of a pulmonary vein or vein ostium can be achieved with both compliant and non-compliant balloon variations.

Notwithstanding the alternatives which may be acceptable as just described, the balloon 820 is preferably constructed to exhibit at least 300% expansion at 3 atmospheres of pressure, and more preferably to exhibit at least 400% expansion at that pressure. The term "expansion" is herein intended to mean the balloon outer diameter after pressurization divided by the balloon inner diameter before pressurization, wherein the balloon inner diameter before pressurization is taken after the balloon is substantially filled with fluid in a taught configuration. In other words, "expansion" is herein intended to relate to change in the diameter that is attributable to the material compliance in a stress strain relationship. In one more detailed construction which is believed to be suitable for use in most conduction block procedures in the region of the pulmonary veins, the balloon is adapted to expand under a normal range of pressure such that its outer diameter may be adjusted from a radially collapsed position of about 5 millimeters to a radially expanded position of about 2.5 centimeters (or approximately 500% expansion ratio).

The ablation member, which is illustrated in FIGS. 30A–D, takes the form of annular ultrasonic transducer 830.

In the illustrated embodiment, the annular ultrasonic transducer 830 has a unitary cylindrical shape with a hollow interior (i.e., is tubular shaped); however, the transducer applicator 830 can have a generally annular shape and be formed of a plurality of segments. For instance, the transducer applicator 830 can be formed by a plurality of tube sectors that together form an annular shape. The tube sectors can also be of sufficient arc lengths so as when joined together, the sectors assembly forms a "clover-leaf" shape. This shape is believed to provide overlap in heated regions between adjacent elements. The generally annular shape can also be formed by a plurality of planar transducer segments which are arranged in a polygon shape (e.g., hexagon). In addition, although in the illustrated embodiment the ultrasonic transducer comprises a single transducer element, the transducer applicator can be formed of a multi-element array, as described in greater detail below.

Cylindrical ultrasound transducer 830 includes a tubular wall 831 which includes three concentric tubular layers. The central layer 832 is a tubular shaped member of a piezoceramic or piezoelectric crystalline material. The transducer preferably is made of type PZT-4, PZT-5 or PZT-8, quartz or Lithium-Niobate type piezoceramic material to ensure high power output capabilities. These types of transducer materials are commercially available from Stavely Sensors, Inc. of East Hartford, Conn., or from Valpey-Fischer Corp. of Hopkinton, Mass.

The outer and inner tubular members 833, 834 enclose central layer 832 within their coaxial space and are constructed of an electrically conductive material. In the illustrated embodiment, these transducer electrodes 833, 834 comprise a metallic coating, and more preferably a coating of nickel, copper, silver, gold, platinum, or alloys of these metals.

One more detailed construction for a cylindrical ultrasound transducer for use in the present application is as follows. The length of the transducer 830 or transducer assembly (e.g., multi-element array of transducer elements) desirably is selected for a given clinical application. In connection with forming circumferential condition blocks in cardiac or pulmonary vein wall tissue, the transducer length can fall within the range of approximately 2 mm up to greater than 10 mm, and preferably equals about 5 mm to 10 mm. A transducer accordingly sized is believed to form a lesion of a width sufficient to ensure the integrity of the formed conductive block without undue tissue ablation. For other applications, however, the length can be significantly longer.

Likewise, the transducer outer diameter desirably is selected to account for delivery through a particular access path (e.g., percutaneously and transeptally), for proper placement and location within a particular body space, and for achieving a desired ablation effect. In the given application within or proximate of the pulmonary vein ostium, the transducer 830 preferably has an outer diameter within the range of about 1.8 mm to greater than 2.5 mm. It has been observed that a transducer with an outer diameter of about 2 mm generates acoustic power levels approaching 20–50 Watts per centimeter radiator or greater within myocardial or vascular tissue, which is believed to be sufficient for ablation of tissue engaged by the outer balloon for up to about 2 cm outer diameter of the balloon. For applications in other body spaces, the transducer applicator 830 may have an outer diameter within the range of about 1 mm to greater than 3–4 mm (e.g., as large as 1 to 2 cm for applications in some body spaces).

The central layer 832 of the transducer 830 has a thickness selected to produce a desired operating frequency. The operating frequency will vary of course depending upon clinical needs, such as the tolerable outer diameter of the ablation and the depth of heating, as well as upon the size of the transducer as limited by the delivery path and the size of the target site. As described in greater detail below, the transducer 830 in the illustrated application preferably operates within the range of about 5 MHz to about 30 MHz, and more preferably within the range of about 7 MHz to about 10 MHz. Thus, for example, the transducer can have a thickness of approximately 0.3 mm for an operating frequency of about 7 MHz (i.e., a thickness generally equal to ½ the wavelength associated with the desired operating frequency).

Figure 30A:
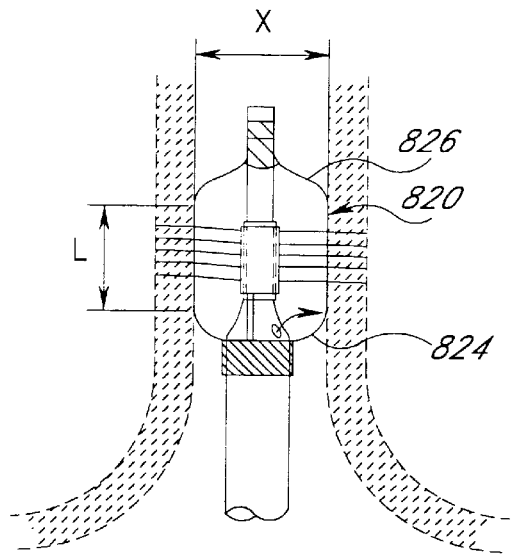
FIG. 30A shows a perspective view of a circumferential ablation probe similar to the probe shown in FIG. 29A, and shows the distal end portion of the circumferential ablation probe during one mode of use in forming a circumferential conduction block in a pulmonary vein in the region of its ostium along a left atrial wall (shown in cross-section in shadow).

The transducer 830 is vibrated across the wall thickness and to radiate collimated acoustic energy in the radial direction. For this purpose, as best seen in FIGS. 30A and 30D, the distal ends of electrical leads 836, 837 are electrically coupled to outer and inner tubular members or electrodes 833, 834, respectively, of the transducer 830, such as, for example, by soldering the leads to the metallic coatings or by resistance welding. In the illustrated embodiment, the electrical leads are 4–8 mil (0.004 to 0.008 inch diameter) silver wire or the like.

The proximal ends of these leads are adapted to couple to an ultrasonic driver or actuator 840, which is schematically illustrated in FIG. 29D. FIGS. 29A–D further show leads 836, 837 as separate wires within electrical lead lumen 808, in which configuration the leads must be well insulated when in close contact. Other configurations for leads 836, 837 are therefore contemplated. For example, a coaxial cable may provide one cable for both leads which is well insulated as to inductance interference. Or, the leads may be communicated toward the distal end portion 812 of the elongate body through different lumens which are separated by the probe body.

The transducer also can be sectored by scoring or notching the outer transducer electrode 833 and part of the central layer 832 along lines parallel to the longitudinal axis L of the transducer 830, as illustrated in FIG. 29E. A separate electrical lead connects to each sector in order to couple the sector to a dedicated power control that individually excites the corresponding transducer sector. By controlling the driving power and operating frequency to each individual sector, the ultrasonic driver 840 can enhance the uniformity of the ultrasonic beam around the transducer 830, as well as can vary the degree of heating (i.e., lesion control) in the angular dimension.

The ultrasound transducer just described is combined with the overall device assembly according to the present embodiment as follows. In assembly, the transducer 830 desirably is "air-backed" to produce more energy and to enhance energy distribution uniformity, as known in the art. In other words, the inner member 803 does not contact an appreciable amount of the inner surface of transducer inner tubular member 834. This is because the piezoelectric crystal which forms central layer 832 of ultrasound transducer 830 is adapted to radially contract and expand (or radially "vibrate") when an alternating current is applied from a current source and across the outer and inner tubular electrodes 833, 834) of the crystal via the electrical leads 836, 837. This controlled vibration emits the ultrasonic energy which is adapted to ablate tissue and form a circumferential conduction block according to the present embodiment. Therefore, it is believed that appreciable levels of contact along the surface of the crystal may provide a dampening effect which would diminish the vibration of the crystal and thus limit the efficiency of ultrasound transmission.

For this purpose, the transducer 830 seats coaxial about the inner member 803 and is supported about the inner member 803 in a manner providing a gap between the inner member 803 and the transducer inner tubular member 834. That is, the inner tubular member 834 forms an interior bore 835 which loosely receives the inner member 803. Any of a variety of structures can be used to support the transducer 830 about the inner member 803. For instance, spacers or splines can be used to coaxially position the transducer 830 about the inner member 803 while leaving a generally annular space between these components. In the alternative, other conventional and known approaches to support the transducer can also be used. For instance, O-rings that circumscribe the inner member 803 and lie between the inner member 803 and the transducer 830 can support the transducer 830 in a manner similar to that illustrated in U.S. Pat. No. 5,606,974; 5,620,479; and 5,606,974, the disclosures of which were previously incorporated by reference above.

In a further mode, the probe shaft 802 can also include additional lumens which lie either side by side to or coaxial, which terminate at ports located within the space between the inner member 803 and the transducer 830. A cooling medium can circulate through space defined by the stand-off 838 between the inner member 803 and the transducer 830 via these additional lumens. By way of example, carbon dioxide gas, circulated at a rate of 5 liters per minute, can be used as a suitable cooling medium to maintain the transducer at a lower operating temperature. It is believed that such thermal cooling would allow more acoustic power to transmit to the targeted tissue without degradation of the transducer material.

The transducer 830 desirably is electrically and mechanically isolated from the interior of the balloon 820. Again, any of a variety of coatings, sheaths, sealants, tubings and the like may be suitable for this purpose, such as those described in U.S. Pat. Nos. 5,620,479 and 5,606,974. In the illustrated embodiment, as best illustrated in FIG. 30C, a conventional, flexible, acoustically compatible, and medical grade epoxy 842 is applied over the transducer 830. The epoxy 842 may be, for example, Epotek 301, Epotek 310, which is available commercially from Epoxy Technology, or Tracon FDA-8. In addition, a conventional sealant, such as, for example, General Electric Silicone II gasket glue and sealant, desirably is applied at the proximal and distal ends of the transducer 830 around the exposed portions of the inner member 803, wires 836, 837 and stand-off 838 to seal the space between the transducer 830 and the inner member 803 at these locations.

An ultra thin-walled polyester heat shrink tubing 844 or the like then seals the epoxy coated transducer. Alternatively, the epoxy covered transducer 830, inner member 803 and stand-off 838 can be instead inserted into a tight thin wall rubber or plastic tubing made from a material such as Teflon®, polyethylene, polyurethane, silastic or the like. The tubing desirably has a thickness of 0.0005 to 0.003 inches.

When assembling the ablation device assembly, additional epoxy is injected into the tubing after the tubing is placed over the epoxy coated transducer 830. As the tube shrinks, excess epoxy flows out and a thin layer of epoxy remains between the transducer and the heat shrink tubing 844. These layers 842, 844 protect the transducer surface, help acoustically match the transducer 830 to the load, makes the ablation device more robust, and ensures air-tight integrity of the air backing.

Although not illustrated in FIG. 29A in order to simplify the drawing, the tubing 844 extends beyond the ends of transducer 830 and surrounds a portion of the inner member 803 on either side of the transducer 830. A filler (not shown) can also be used to support the ends of the tubing 844. Suitable fillers include flexible materials such as, for example, but without limitation, epoxy, Teflon® tape and the like.

The ultrasonic actuator 840 generates alternating current to power the transducer 830. The ultrasonic actuator 840 drives the transducer 830 at frequencies within the range of about 5 to about 50 MHz, and preferably for the illustrated application within the range of about 7 MHz to about 10 MHz. In addition, the ultrasonic driver can modulate the driving frequencies and/or vary power in order to smooth or unify the produced collimated ultrasonic beam. For instance, the function generator of the ultrasonic actuator 840 can drive the transducer at frequencies within the range of 6.8 MHz and 7.2 MHz by continuously or discretely sweeping between these frequencies.

The ultrasound transducer 830 of the present embodiment sonically couples with the outer skin of the balloon 820 in a manner which forms a circumferential conduction block in a pulmonary vein as follows. Initially, the ultrasound transducer is believed to emit its energy in a circumferential pattern which is highly collimated along the transducer's length relative to its longitudinal axis L (see FIG. 30D). The circumferential band therefore maintains its width and circumferential pattern over an appreciable range of diameters away from the source at the transducer. Also, the balloon is preferably inflated with fluid which is relatively ultrasonically transparent, such as, for example, degassed water. Therefore, by actuating the transducer 830 while the balloon 820 is inflated, the circumferential band of energy is allowed to translate through the inflation fluid and ultimately sonically couple with a circumferential band of balloon skin which circumscribes the balloon 820. Moreover, the circumferential band of balloon skin material may also be further engaged along a circumferential path of tissue which circumscribes the balloon, such as, for example, if the balloon is inflated within and engages a pulmonary vein wall, ostium, or region of atrial wall. Accordingly, where the balloon is constructed of a relatively ultrasonically transparent material, the circumferential band of ultrasound energy is allowed to pass through the balloon skin and into the engaged circumferential path of tissue such that the circumferential path of tissue is ablated.

Further to the transducer-balloon relationship just described, the energy is coupled to the tissue largely via the inflation fluid and balloon skin. It is believed that, for in vivo uses, the efficiency of energy coupling to the tissue, and therefore ablation efficiency, may significantly diminish in circumstances where there is poor contact and conforming interface between the balloon skin and the tissue. Accordingly, it is contemplated that several different balloon types may be provided for ablating different tissue structures so that a particular shape may be chosen for a particular region of tissue to be ablated.

Figure 31A:
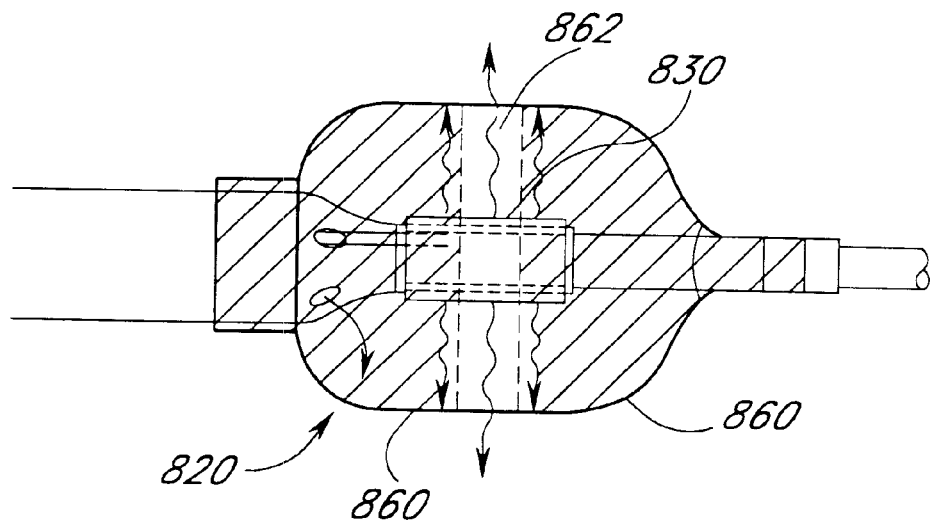
FIG. 31A shows a cross-sectional view of the distal end portion of another circumferential ablation probe, wherein an outer shield or filter is provided along the balloon's outer surface in order to form a predetermined shape for the circumferential ablation element created by sonic transmissions from the inner ultrasound transducer.

In one particular balloon-transducer combination shown in FIG. 29A and also in FIG. 31A, the ultrasound transducer preferably has a length such that the ultrasonically coupled band of the balloon skin, having a similar length d according to the collimated ultrasound signal, is shorter than the working length D of the balloon. According to this aspect of the relationship, the transducer is adapted as a circumferential ablation member which is coupled to the balloon to form an ablation element along a circumferential band of the balloon, therefore forming a circumferential ablation element band which circumscribes the balloon. Preferably, the transducer has a length which is less than two-thirds the working length of the balloon, and more preferably is less than one-half the working length of the balloon. By sizing the ultrasonic transducer length d smaller than the working length D of the balloon 820—and hence shorter than a longitudinal length of the engagement area between the balloon 820 and the wall of the body space (e.g., pulmonary vein ostium)—and by generally centering the transducer 830 within the balloon's working length D, the transducer 830 operates in a field isolated from the blood pool. A generally equatorial position of the transducer 830 relative to the ends of the balloon's working length also assists in the isolation of the transducer 830 from the blood pool. It is believed that the transducer placement according to this arrangement may be preventative of thrombus formation which might otherwise occur at a lesion sight, particularly in the left atrium.

The ultrasound transducer described in various levels of detail above has been observed to provide a suitable degree of radiopacity for locating the energy source at a desired location for ablating the conductive block. However, it is further contemplated that the probe shaft 802 may include an additional radiopaque marker or markers (not shown) to identify the location of the ultrasonic transducer 830 in order to facilitate placement of the transducer at a selected ablation region of a pulmonary vein via X-ray visualization. The radiopaque marker is opaque under X-ray, and can be constructed, for example, of a radiopaque metal such as gold, platinum, or tungsten, or can comprise a radiopaque plastic (e.g., polymer) such as a metal loaded polymer. The radiopaque marker is positioned coaxially over an inner tubular member 803.

The present circumferential ablation device is introduced into a pulmonary vein of the left atrium in a manner similar to that described previously. Once properly positioned within the pulmonary vein or vein ostium, the pressurized fluid source inflates the balloon 820 to engage the lumenal surface of the pulmonary vein ostium. Once properly positioned, the ultrasonic driver 840 is energized to drive the transducer 830. It is believed that by driving the ultrasonic transducer 830 at 20 acoustical watts at an operating frequency of 7 megahertz, that a sufficiently sized lesion can be formed circumferentially about the pulmonary vein ostium in a relatively short period of time (e.g., 1 to 2 minutes or less). It is also contemplated that the control level of energy can be delivered, then tested for lesion formation with a test stimulus in the pulmonary vein, either from an electrode provided at the tip area of the ultrasonic probe or on a separate device. Therefore, the procedure may involve ablation at a first energy level in time, then check for the effective conductive block provided by the resulting lesion, and then subsequent ablations and testing until a complete conductive block is formed. In the alternative, the circumferential ablation device may also include feedback control, for example, if thermocouples are provided at the circumferential element formed along the balloon outer surface. Monitoring temperature at this location provides indicia for the progression of the lesion. This feedback feature may be used in addition to or in the alternative to the multi-step procedure described above.

Figure 30B:
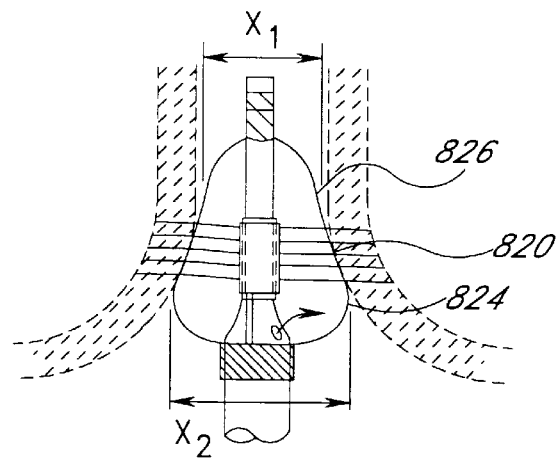
FIG. 30B shows a similar perspective and cross-sectional shadow view of a circumferential ablation probe and pulmonary vein ostium as that shown in FIG. 30A wherein the inflatable balloon has a tapered outer diameter for conforming to the shape of the ostium.
Figure 30C:
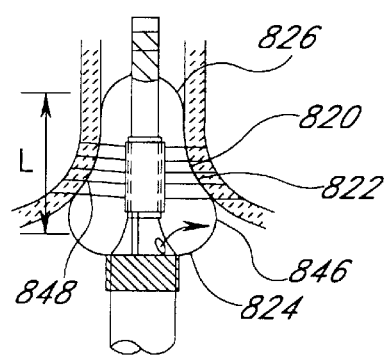
FIG. 30C shows a similar view to that shown in FIGS. 30A–B, although showing another circumferential ablation probe wherein the balloon has a "pear"-shaped outer diameter with a contoured surface along a taper which is adapted to seat in the ostium of a pulmonary vein.
Figure 30D:
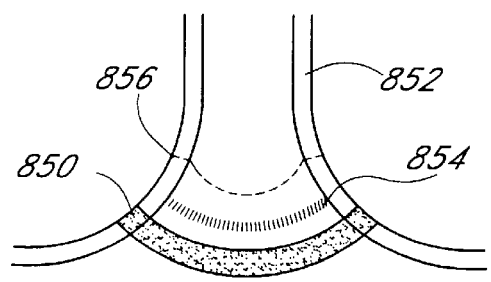
FIG. 30D shows a cross-sectional view of one circumferential conduction block which may be formed by use of a circumferential ablation probe such as that shown in FIG. 30C.

FIGS. 30A–C show various alternative designs for the purpose of illustrating the relationship between the ultrasound transducer and balloon of the assemblies just described above. More specifically, FIG. 30A shows the balloon 820 having "straight" configuration with a working length L and a relatively constant diameter X between proximal and distal tapers 824, 826. As is shown in FIG. 30A, this variation is believed to be particularly well adapted for use in forming a circumferential conduction block along a circumferential path of tissue which circumscribes and transects a pulmonary vein wall. However, unless the balloon is constructed of a material having a high degree of compliance and conformability, this shape may provide for gaps in contact between the desired circumferential band of tissue and the circumferential band of the balloon skin along the working length of the balloon 820.

The balloon 820 in FIG. 30A is also concentrically positioned relative to the longitudinal axis of the probe shaft 802. It is understood, however, that the balloon can be asymmetrically positioned on the elongate body, and that the ablation device can include more than one balloon.

FIG. 30B shows another circumferential ablation device assembly for pulmonary vein isolation, although this assembly includes a balloon 820 which has a tapered outer diameter from a proximal outer diameter $X_2$ to a smaller distal outer diameter $X_1$. (Like reference numerals have been used in each of these embodiments in order to identify generally common elements between the embodiments.) According to this mode, this tapered shape is believed to conform well to other tapering regions of space, and may also be particularly beneficial for use in engaging and ablating circumferential paths of tissue along a pulmonary vein ostium.

FIG. 30C further shows a similar shape for the balloon as that just illustrated by reference to FIG. 30B, except that the FIG. 30C embodiment further includes a balloon 820 and includes a bulbous proximal end 846. In the illustrated embodiment, the proximate bulbous end 846 of the central region 822 gives the balloon 820 a "pear"-shape. More specifically, a contoured surface 848 is positioned along the tapered working length L and between proximal shoulder 824 and the smaller distal shoulder 826 of balloon 820. As is suggested by view of FIG. 30C, this pear shaped embodiment is believed to be beneficial for forming the circumferential conduction block along a circumferential path of atrial wall tissue which surrounds and perhaps includes the pulmonary vein ostium. For example, the device shown in FIG. 30C is believed to be suited to form a similar lesion to that shown at circumferential lesion 850 in FIG. 30D. Circumferential lesion 850 electrically isolates the respective pulmonary vein 852 from a substantial portion of the left atrial wall. The device shown in FIG. 30C is also believed to be suited to form an elongate lesion which extends along a substantial portion of the pulmonary vein ostium 854, e.g., between the proximal edge of the illustrated lesion 850 and the dashed line 856 which schematically marks a distal edge of such an exemplary elongate lesion 850.

As mentioned above, the transducer 830 can be formed of an array of multiple transducer elements that are arranged in series and coaxial. The transducer can also be formed to have a plurality of longitudinal sectors. These modes of the transducer have particular utility in connection with the tapering balloon designs illustrated in FIGS. 30B and 30C. In these cases, because of the differing distances along the length of the transducer between the transducer and the targeted tissue, it is believed that a non-uniform heating depth could occur if the transducer were driven at a constant power. In order to uniformly heat the targeted tissue along the length of the transducer assembly, more power may therefore be required at the proximal end than at the distal end because power falls off as 1/radius from a source (i.e., from the transducer) in water. Moreover, if the transducer 830 is operating in an attenuating fluid, then the desired power level may need to account for the attenuation caused by the fluid. The region of smaller balloon diameter near the distal end thus requires less transducer power output than the region of larger balloon diameter near the proximal end. Further to this premise, in a more specific embodiment transducer elements or sectors, which are individually powered, can be provided and produce a tapering ultrasound power deposition. That is, the proximal transducer element or sector can be driven at a higher power level than the distal transducer element or sector so as to enhance the uniformity of heating when the transducer lies skewed relative to the target site.

The circumferential ablation device 800 can also include additional mechanisms to control the depth of heating. For instance, the probe shaft 802 can include an additional lumen which is arranged on the body so as to circulate the inflation fluid through a closed system, such as a heat exchanger. A heat exchanger can remove heat from the inflation fluid and the flow rate through the closed system can be controlled to regulate the temperature of the inflation fluid. The cooled inflation fluid within the balloon 820 can thus act as a heat sink to conduct away some of the heat from the targeted tissue and maintain the tissue below a desired temperature (e.g., 90 decrees C), and thereby increase the depth of heating. That is, by maintaining the temperature of the tissue at the balloon/tissue interface below a desired temperature, more power can be deposited in the tissue for greater penetration. Conversely, the fluid can be allowed to warm. This use of this feature and the temperature of the inflation fluid can be varied from procedure to procedure, as well as during a particular procedure, in order to tailor the degree of ablation to a given application or patient.

The depth of heating can also be controlled by selecting the inflation material to have certain absorption characteristics. For example, by selecting an inflation material with higher absorption than water, less energy will reach the balloon wall, thereby limiting thermal penetration into the tissue. It is believed that the following fluids may be suitable for this application: vegetable oil, silicone oil and the like.

Uniform heating can also be enhanced by rotating the transducer within the balloon. For this purpose, the transducer 830 may be mounted on a torquable member which is movably engaged within a lumen that is formed by the probe shaft 802.

In general as to the variations embodied by those figures, the circumferential ultrasound energy signal is modified at the balloon coupling level such that a third order of control is provided for the tissue lesion pattern (the first order of control is the transducer properties affecting signal emission, such as length, width, shape of the transducer crystal; the second order of control for tissue lesion pattern is the balloon shape, per above by reference to FIGS. 30A–C).

Figure 31B:
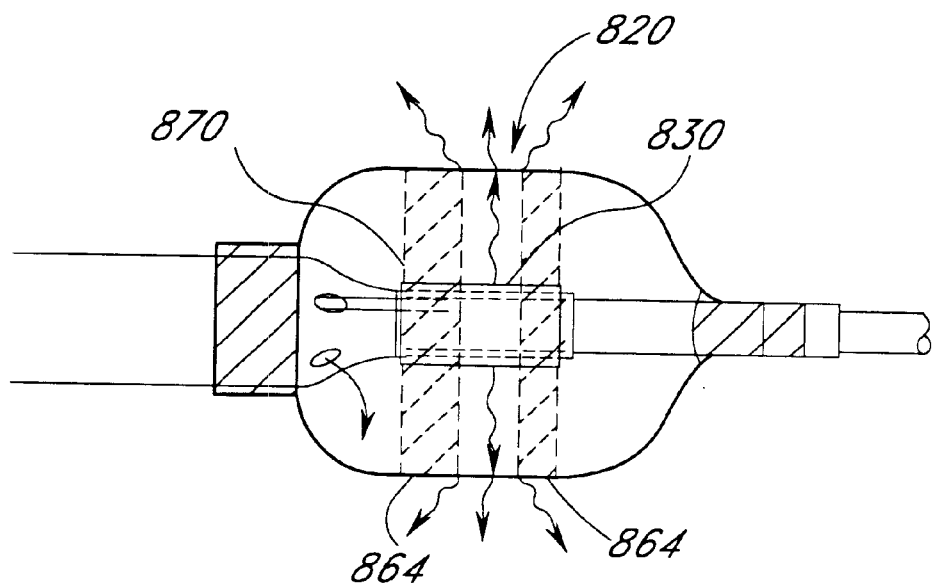
FIG. 31B shows a similar view as that shown in FIG. 31A, although showing the distal end portion of another circumferential ablation probe which includes a heat sink as an equatorial band within the circumferential path of energy emission from an inner ultrasound transducer.

Another aspect of the balloon-transducer relationship of the present embodiment is illustrated by reference to FIGS. 31A–B. In general, as to the variations embodied by those Figures, the circumferential ultrasound energy signal is modified at the balloon coupling level such that a third order of control is provided for the tissue lesion pattern (the first order of control is the transducer properties affecting signal emission, such as length, width, shape of the transducer crystal; the second order of control for tissue lesion pattern is the balloon shape, per above by reference to FIGS. 30A–C).

This third order of control for the tissue lesion pattern can be understood more particularly with reference to FIG. 31A, which shows balloon 820 to include a shield or filter 860. The filter 860 has a predetermined pattern along the balloon surface adapted to shield tissue from the ultrasound signal, for example, by either absorbing or reflecting the ultrasound signal. In the particular variation shown in FIG. 31A, the filter 860 is patterned so that the energy band which is passed through the balloon wall is substantially more narrow than the band that emits from the transducer 830 internally of the balloon 820. The filter 860 can be constructed, for example, by coating the balloon 820 with an ultrasonically reflective material, such as with a metal, or with an ultrasonically absorbent material, such as with a polyurethane elastomer. Or, the filter can be formed by varying the balloon's wall thickness such that a circumferential band 862, which is narrow in the longitudinal direction as compared to the length of the balloon, is also thinner (in a radial direction) than the surrounding regions, thereby preferentially allowing signals to pass through the band 862. The thicker walls of the balloon 820 on either side of the band 862 inhibit propagation of the ultrasonic energy through the balloon skin at these locations.

That is, the disclosed modes of suspension maintain an air gap between the transducer and the probe shaft. As mentioned above, air backing of a cylindrical acoustic transducer is desirable to ensure maximum radially outward propagation of the ultrasound waves. While the transducer is damped whenever it is in contact with any sort of mounting means between the back or inner side of the transducer and the probe shaft, even highly elastomeric ones, the disclosed designs of these Figures are constructed to minimize such damping. In addition, the air space desirably is sealed to prevent fluid infiltration, be it blood or water. These features are common to the following construction variations.

In each of the variations disclosed below, the transducer is constructed for use in applications involving forming a circumferential lesion at a base of or in a pulmonary vein to treat atrial fibrillation as described above. In this application, the transducer preferably is driven in a range of about 6 to about 12 MHz. The transducer for this purpose can have a thickness in the range of about 0.009 (0.23 mm) to about 0.013 inches (0.33 mm). For example, a preferred transducer in accordance with the suspended coaxial transducer embodiment may have an inner diameter of 0.070 inch (1.8 mm) and an outer diameter of 0.096 inch (2.4 mm); thus, having a thickness of 0.013 inch (0.3 mm).

While the probe assemblies and associated methods of manufacture disclosed for constructing a suspended, generally coaxial ultrasonic transducer have applications in connection with forming circumferential lesions to treat atrial fibrillation as described above, those skilled in the art will readily recognize that the present constructions and methods of manufacture can be used for constructing ultrasonic elements for the delivery into and the ablation of other body spaces in the treatment of other medical conditions, as well as in connection with other applications outside the medical field. For instance, the ultrasound ablation device described above and the variations thereof described below may be used for joining adjacent linear lesions in a less-invasive "maze"-type procedure, or be used within the coronary sinus to ablate the atrioventricular (AV) node to treat Wolff-Parkinson-White syndrome and any other accessory conductive pathway abnormality. In this latter application, it may be desirably to ablate only a portion of the circumference of the coronary sinus. In addition, these types of ablation devices can be mounted onto a pre-shaped probe shaft that has a curvature that generally matches a natural curvature of the coronary sinus about the exterior of the heart. Such pre-shaped probe may self-orient within the coronary sinus to position the active ultrasonic transducer toward the inner side of the coronary sinus (i.e., toward the interior of the heart) so as to direct transmission toward the AV node. A probe constructed with the ultrasonic transducer mounting assemblies disclosed herein can also be designed without an anchoring balloon for use on an end of a probe for the treatment of ventricular tachycardia.

For various reasons, the "narrow pass filter" device may be particularly well suited for use in forming circumferential conduction blocks in left atrial wall and pulmonary vein tissues according to the present invention. It is believed that the efficiency of ultrasound transmission from a piezoelectric transducer is limited by the length of the transducer, which limitations are further believed to be a function of the wavelength of the emitted signal. Thus, for some applications a transducer may be required to be longer than the length which is desired for the lesion to be formed. Many procedures intending to form conduction blocks in the left atrium or pulmonary veins, such as, for example, less-invasive "maze"-type procedures, require only enough lesion width to create a functional electrical block and to electrically isolate a tissue region. In addition, limiting the amount of damage formed along an atrial wall, even in a controlled ablation procedure, pervades as a general concern. However, a transducer that is necessary to form that block, or which may be desirable for other reasons, may require a length which is much longer and may create lesions which are much wider than is functionally required for the block. A "narrow pass" filter along the balloon provides one solution to such competing interests.

Another variation of the balloon-transducer relationship in an ultrasound ablation assembly according to the present invention has placement of an ultrasonically absorbent band along balloon and directly in the central region of the emitted energy signal from transducer. According to this variation, the ultrasonically absorbent band is adapted to heat to a significant temperature rise when sonically coupled to the transducer via the ultrasound signal. It is believed that some ablation methods may benefit from combining ultrasound/thermal conduction modes of ablation in a targeted circumferential band of tissue. In another aspect of this variation, ultrasonically absorbent band may operate as an energy sink as an aid to control the extent of ablation to a less traumatic and invasive level than would be reached by allowing the raw ultrasound energy to couple directly to the tissue. In other words, by heating the absorbent band the signal is diminished to a level that might have a more controlled depth of tissue ablation. Further to this aspect, absorbent band may therefore also have a width which is more commensurate with the length of the transducer.

It is further contemplated that, where outer shields, absorbent bands, or sinks are placed over and around the ultrasound transducer, use of the transducer as a position monitoring sensor, as described herein according to various devices, may be affected. For example, the ultrasonic shield or sink may produce a pronounced signal reflecting the distance of the expanded balloon from the transducer, which signal may mask or otherwise affect the ability to sense the signal that represents the desired anatomical information radially disposed from the ablation region along the balloon. Therefore, signal processing or other means to recognize distinctive characteristics of the desired anatomical signal may be required to decipher between the anatomical ultrasound data and sensed ultrasound data from the shield(s) or sink(s).

The ultrasonic transducer preferably has an annular shape so as to emit ultrasonic energy around the entire circumference of the balloon. The present circumferential ablation device, however, can emit a collimated beam of ultrasonic energy in a specific angular exposure. For instance, the transducer can be configured to have only a single active sector (e.g., 180° exposure). The transducer can also have a planar shape. By rotating the elongate body, the transducer can be swept through 360° in order to form a circumferential ablation. For this purpose, the transducer may be mounted on a torquible member, in the manner described above.

Another type of ultrasonic transducer, which can be mounted to a torquible member within the balloon, can be constructed as follows. The transducer is formed by curvilinear section and is mounted on the torquible member with its concave surface facing in a radially outward direction. The torquible member desirably is formed with recess that substantially matches a portion of the concave surface of the transducer. The torquible member also includes longitudinal ridges on the edges of the recess that support the transducer above the probe shaft such that an air gap is formed between the transducer and the torquible member. In this manner, the transducer is "air-backed." This spaced is sealed and closed in the manner described above.

The inverted transducer section produces a highly directional beam pattern. By sweeping the transducer through 360° of rotation, as described above, a circumferential lesion can be formed while using less power than would be required with a planar or tubular transducer. This rotation is achieved by rotating the torquible member, which rotates within a lumen of the probe shaft.

It is to be further understood that the various modes of the ultrasound-balloon devices just described may be used according to several different particular methods such as those methods otherwise set forth throughout this disclosure. For example, any of the ultrasound transducer devices may be used to form a conduction block in order to prevent or treat focal arrhythmia arising from a specific pulmonary vein, or may alternatively or additionally be used for joining adjacent linear lesions in a less-invasive "maze"-type procedure.

A circular array of ultrasonic transducers having the inner electrode may be used as a common electrode and the cylindrical piezoelectric material as a common element. The single outer electrode, however, is separated by four longitudinal grooves into four electrodes disposed about the outer surface of the piezoelectric material. The four electrodes correspond to the array of four sensors, each electrode corresponding to one sensor.

When an AC voltage is impressed between the inner electrode and a selected one of the four electrodes, the piezoelectric material vibrates in the region between the inner electrode and the selected electrode. For example, an AC voltage impressed between the inner electrode and the electrode will cause the region between the electrode and the electrode to vibrate. However, the piezoelectric material is a single piece of material, so a vibration between the inner electrode and the electrode will also cause some vibration in the regions between the electrodes. The vibration in the regions between the electrodes will generate a voltage. Thus, the sensors produced by the electrodes are not completely independent of one another and there will be some coupling between the sensors.

The coupling between the sensors produced by the electrodes can be reduced by extending the longitudinal grooves between the electrodes into the single piece of piezoelectric material to provide a zoned piezoelectric material. The grooves in the piezoelectric material will tend to physically separate the piezoelectric material into four zones. Each zone will have less mass than the single piece of piezoelectric material, and thus each of the four zones will typically provide a faster right-down time than the single piezoelectric material.

The coupling between the sensors produced by the electrodes can be further reduced by extending the longitudinal grooves all the way through the piezoelectric material, thereby producing four separate pieces of piezoelectric material.

The electrodes can be driven separately thereby providing four separate transducers. The electrodes can also be driven in unison to provide a single transducer.

Various forms of ablation elements may be suitable for use in an overall ablation assembly as contemplated within the present invention.

In one example, the band includes one or more conductive electrodes. In one device, the band includes a porous skin that is adapted to allow fluid, such as hypertonic saline solution, to pass from an internal chamber defined by the probe and outwardly to contact the tissues of the ostium. Such a porous skin can be constructed according to several different methods, such as by forming holes in an otherwise contiguous polymeric material, including mechanically drilling or using laser energy, or the porous skin may simply be an inherently porous construction, such as a porous fluoropolymer, e.g. polytetrafluoroethylene (PTFE), cellulose, polyurethane, or other porous material, blend, or construction. In any case, by electrically coupling the fluid within the porous balloon skin to an RF current source (preferably monopolar), the porous band serves as an electrode wherein RF current flows outwardly through the pores via the conductive fluid. In addition, it is further contemplated that a porous outer skin may be provided externally of another, separate expandable member, such as a separate expandable balloon, wherein the conductive fluid is contained in a region between the porous outer skin and the expandable member contained therein. Various other "fluid electrode" designs than those specifically herein described may also be suitable according to one of ordinary skill upon review of this disclosure.

In the alternative, or in addition to the RF electrode variations just described, the circumferential ablation element may also include other ablative energy sources or sinks, and particularly may include a thermal conductor that circumscribes the outer circumference of the working length of an expandable member. Examples of suitable thermal conductor arrangements include a metallic element, which can, for example, be constructed as previously described for the more detailed RF devices above. In one device, the thermal conductor, such a metallic element, can be generally either resistively heated in a closed loop circuit internal to the probe, or conductively heated by a heat source coupled to the thermal conductor. In the latter case of conductive heating of the thermal conductor with a heat source, the expandable member may be for example a polymeric balloon skin which is inflated with a fluid that is heated either by a resistive coil or by bipolar RF current. In any case, it is believed that a thermal conductor on the outer surface of the expandable member is suitable when it is adapted to heat tissue adjacent thereto to a temperature between 40° and 80° C.

As noted above, the probe assembly can include one or more temperature sensors (e.g., thermocouples) to (1) determine the position of the ablation member and/or (2) monitor tissue ablation. Thus, such temperature sensors can be used in conjunction with all of the position monitoring systems described above.

The probe assembly can also include one or more electrodes arranged to make contact with venous and/or cardiac tissue adjacent the targeted region of tissue. Such electrodes desirably are arranged for electrical mapping purposes as well as to check the integrity of the conductive block after ablation of the region of tissue. For instance, in one mode, an electrode is mounted distal of the ablation element and is used to invoke an arrythemogenic condition in venous/cardiac tissue distal of the formed lesion. This electrode can be used by itself or in combination with one or more electrodes that are positioned proximally of this distal-most electrode.

One or more of these proximal electrodes can be used to map the responsive electro-physiological response to determine whether the response transcends the formed lesion (i.e., the produced conductive block). In one variation, the probe includes only one distal electrode and a proximal electrode positioned on opposite sides of the ablation element. In another variation, the probe includes an array of electrodes positioned along a length of the probe. When the expandable member lies in a collapsed position, the distal portion of the delivery member can be manipulated to position the array of electrodes against the tissue and across the formed lesion. In this manner, the integrity of the formed conduction block being formed can be monitored and checked.

Both temperature sensors and electrodes desirably are arranged along at least a portion of the length of the expandable member (e.g., the inflatable balloon). The following provides a description of several ways to attach such sensors and electrodes to or use such sensors and electrodes with an expandable member.

The temperature sensor devices herein described are believed to be particularly well suited for use with highly elastomeric balloons, wherein such designs are at least in part intended to account for and accommodate high amounts of elongation at the balloon/sensor interface. More particular examples of such highly compliant or elastomeric balloons are described elsewhere in this disclosure.

Notwithstanding the highly beneficial aspects of such assemblies, the embodiments may also be combined with other non-compliant balloon varieties, or may be further coupled to other ablation members not incorporating balloons, such as for example those using expandable cages, wherein the outer perimeter of such cage may be interchangeably substituted with the balloon skin in the devices described. In other more isolated instances, the temperature monitoring sensor assemblies herein disclosed may be combined with certain circumferential ablation members without reliance on any particular circumferential ablation member design, such as in the event of deployable thermocouple splines that may be positioned in a circumferential pattern in order to monitor ablation in a manner that is relatively independent of the ablation member features.

Suitable shapes for the thermocouple include, but are not limited to, a loop, an oval loop, a "T" configuration, an "S" configuration, a hook configuration or a spherical ball configuration. Such shapes are desirable both for anchoring the thermocouple to the balloon and for sensing the temperature of tissue outside the balloon. That is, in each of the above shapes a portion of the thermocouple lies generally normal to, or at least skewed relative to, the axis of the thermocouple wire to enhance the coupling between the thermocouple and the adhesive that bonds it to the balloon wall, as described below. These shapes also provide more surface area for the thermocouple without lengthening the thermocouple. These thermocouples, with more exposed area than a straight thermocouple, are believed to have better accuracy and response time.

The thermocouple is attached to an inside wall of the balloon by a fastener. In one variation, the fastener is a bead of adhesive that is compatible with the material used for manufacturing the balloon. Suitable adhesives include, but are not limited to, epoxies, cyanoacetate adhesives, silicone adhesives, flexible adhesives, etc. In alternate embodiments, the fastener is a tape that is bonded to the balloon, a bead of material that is molded or heat-bonded to the balloon.

The thermocouple wire preferably has sufficient flexibility so that it does not seriously impede the expansion of the balloon. Additionally, according to one highly beneficial aspect of the embodiment, the thermocouple wire is provided with a looped or single-turn spring shape so that the wire expands with the balloon, and again does not seriously impede the expansion of the balloon, as well as not pull on the embedded thermocouple when the balloon is expanded.

Thermocouple wires may be cut to the desired length and then soldered where the temperature monitoring is to be made—such solder removes insulation between the individual strands of the bifilar and electrically couples the leads in a manner that is sensitive to changes in temperature. Notwithstanding the benefits provided by such thermocouples in the present embodiments, other well-known temperature sensors may be suitable substitutes for the thermocouples described herein without departing from the scope of the invention.

The attachment points are typically located in high-stress areas. In one embodiment, the wall of the balloon may be reinforced near attachment points. More specifically, a reinforcement wherein the wall surface of the balloon is thickened on an inner side near the attachment point. Thickening the inner surface wall provides increased strength while still maintaining a smooth outer surface of the balloon, thus allowing the balloon to be easily manipulated inside the body of the patient.

Where a thermocouple is positioned within the path of ablative coupling between an ablation element within the balloon and the balloon/tissue interface, there may be false temperature readings for that thermocouple due to a response of the thermocouple itself to the ablation energy (e.g. ultrasonic heating of the thermocouple within an ultrasonic ablation energy path may heat the thermocouple to a greater temperature than its surroundings). In this case, providing multiple thermocouples at different locations and comparing their operating parameters (e.g. response times, etc.) may provide useful information to allow certain such variables to be filtered and thereby calculate an accurate temperature at the thermocouple location.

An ablation system can be provided with electrodes to be used for mapping the conductivity of the pulmonary vein and to ascertain the effectiveness of the ablation. A distal electrode is distal to an ablated region of the tissue and the proximal electrode is proximal to the ablated region. According to this orientation, the distal and proximal electrodes are positioned to allow the monitoring of an action potential across the ablation zone where the thermocouple is located, thereby enabling a user to confirm formation of a conduction block either during or after performing an ablation procedure with the assembly.

Referring again to FIG. 19, the ablation probe 100 also desirably includes feedback control. For instance, the expandable member 106 can include one or more thermal sensors 146 (e.g., thermocouples, thermistors, etc.) that are provided to either the outer side or the inside of the expandable member 106. Monitoring temperature at this location provides indicia for the progression of the lesion. If the temperature sensors are located inside the expandable member 106, the feedback control may also need to account for any temperature gradient that occurs through the wall of the expandable member. If the sensors are placed on the exterior of the expandable member, they may also be used to record electrogram signals by reconnecting the signal leads to different input port of a signal-processing unit. Such signals can be useful in mapping the target tissue both before and after ablation.

The thermocouples and/or electrodes desirably are blended into the expandable member in order to present a smooth profile. Transition regions, which are formed by either adhesive or melted polymer tubing, "smooth out" the surface of the expandable member as the surface steps up from the outer surface of the expandable member to the thermocouple surface. Various constructions to integrate the thermocouples and/or electrodes into the expandable member, as well as various approaches to using thermocouples and electrodes with an expandable member, are described in detail below.

The ablation probe assembly of the present invention is designed for treatment of the more common forms of atrial fibrillation, resulting from perpetually wandering reentrant wavelets. Such arrhythmias are generally not amenable to localized ablation techniques, because the excitation waves may circumnavigate a focal lesion. Thus, the probe assembly uses the ablation element to form a substantially circumferential lesion, or lesions, to segment the atrial tissue so as to block conduction of the reentrant wave fronts.

Delivery of energy (e.g., thermal, RF, ultrasonic, electrical, etc.) to the tissue of the pulmonary vein ostium is commenced once the ablation element is positioned at the desired location and anchored there by expansion of the expandable member. Good coupling of the energy produced by the ablation element with the tissue facilitates creation of a continuous lesion. Energy from the ablation control system is typically delivered to the ablation element via electrical conductor leads. The ablation control system includes a current source for supplying current to the ablation element, a monitoring circuit, and a control circuit. The current source is coupled to the ablation element via a lead set (and to a ground patch in some modes). The monitor circuit desirably communicates with one or more sensors (e.g., temperature and/or current sensors) which monitor the operation of the ablation element. The control circuit is connected to the monitoring circuit and to the current source in order to adjust the output level of the current driving the ablation element based upon the sensed condition (e.g., upon the relationship between the monitored temperature and a predetermined temperature set point).

In some modes of the present deflectable ablation probe, a position monitoring system may be employed to facilitate positioning of the ablation member. The position monitoring system includes a sensor control system and a display. The sensor control system communicates with one or more sensor elements located in, or near the expandable member. In one variation, the ablation element and sensor element are combined in a single element that provides both sensing and ablation capabilities. In other variations, separate elements are used for the ablation element and the sensor element(s).

An ultrasonic position monitoring system uses a single, circumferentially symmetric ultrasonic transducer. The sensor can be the ultrasonic ablation element, or a separate ultrasonic transducer in addition to an ultrasonic ablation element. The transducer is positioned in a pulmonary vein, and the transducer is operably connected to a sensor control system. In one device, the sensor control system is a Panametrics Model 5073PR. The sensor control system includes a transmitter, a receiver, and a diplexer. An output from the transmitter is provided to a transmitter port (port 1)

of the diplexer. An output from a receiver port (port 3) of the diplexer is provided to an input of the receiver. A transducer port (port 2) of the diplexer is provided through a connector to the transducer. An output from the receiver is provided to the display.

A diplexer is commonly used in radar and sonar systems to isolate the transmitter output from the receiver input. Energy provided to the transmitter port of the diplexer (port 1) is provided to the transducer port (port 2) of the diplexer, but not to the receiver port of the diplexer (port 3). Energy provided from the transducer to the transducer port of the diplexer (port 2) is provided to the receiver port (port 3) of the diplexer, but not to the transmitter port (port 3) of the diplexer.

The diplexer can be a circulator or an electronically controlled switch controlled by a timing generator. The timing generator sets the switch to connect the transmitter to the transducer for a first time period. The timing generator then sets the switch to connect the receiver to the transducer for a second time period. By switching the transducer between the transmitter and the receiver, the diplexer effectively "timeshares" the transducer between the transmitter and the receiver.

The transmitter generates a signal that drives the transducer. When the diplexer connects the transmitter to the transducer, the drive signal from the transmitter causes the transducer to emit an ultrasonic sound wave. The ultrasonic sound wave propagates through the interior of the expandable member, through the wall of the expandable member, and reflects off of the inner wall of the ostium. The reflected ultrasonic energy returns to the transducer and causes the transducer to generate an echo signal. The echo signal is provided through the diplexer to the receiver. The receiver amplifies and processes the echo signal to produce a display signal. The display signal is provided to the display.

The transducer transmits a radiated wave. For a cylindrically symmetric transducer, the radiated wave will approximate a cylindrical wave that expands away from the transducer. When the cylindrical wave reaches the ostium, the wave will be reflected in a substantially cylindrically symmetric fashion to produce a reflected wave that is similar to a cylindrical wave as well. The reflected wave propagates back to the transducer.

Reflections will occur when the ultrasonic sound wave propagating in a medium strikes a transition (or interface) in the acoustic properties of the medium. Any interface between materials having different acoustic properties will cause a portion of the wave to be reflected.

The transmitted pulse causes the transducer to vibrate (in a manner very similar to a bell) during the ring-down period thereby producing the ring-down signal. The echo pulse is caused by ultrasonic energy that is reflected from the ostium back to the transducer. During the ring-down period it is difficult to see signals caused by reflections (such as the signal) because the signals produced by reflections are typically relatively small in amplitude and are easily masked by the relatively large amplitude portions of the ring-down signal. Thus, it is difficult to detect reflections from targets that are so close to the transducer that their reflections return during the ring-down period. This can limit the minimum useful range of the transducer.

The ring-down time of the transducer can be reduced by configuring the transmitter to provide a shaped transmit pulse. The shaped transmit pulse drives the transducer in a manner that reduces the amplitude of the ringing and shortens the ring-down period. Since the ring-down period is shorter, the shaped transmit pulse allows the transducer to be used to detect targets at a shorter distance.

In a device where the transducer is also used as the ablation element, the transmitter provides two power modes, a low-power mode used for position measurements, and a high-power mode used for ablation. When ablation is desired, the diplexer stops switching between the receiver and the transmitter, and stays locked on the transmitter while the transmitter operates in the high-power mode.

Ultrasonic ablation requires that the transducer produce an ultrasonic wave having relatively higher power. Higher power typically requires a transducer having a relatively large physical size. Larger transducers often have longer ring-down times. While the use of a shaped transmitter pulse will reduce ring-down times, for some transducers even the use of a shaped transmit pulse does not shorten the ring-down time sufficiently to allow the ablation element to be used for position sensing. Moreover, in some devices, the ablation element is not an ultrasonic transducer, and thus may be unsuitable for use as a position sensor. Thus, in some devices, it is desirable to add one or more ultrasonic transducers to be used for position sensing.

One more detailed construction for a cylindrical ultrasound transducer for use in the present application is as follows. The length of the transducer or transducer assembly (e.g., multi-element array of transducer elements) desirably is selected for a given clinical application. In connection with forming circumferential condition blocks in cardiac or pulmonary vein wall tissue, the transducer length can fall within the range of approximately 2 mm up to greater than 10 mm, and preferably equals about 5 mm to 10 mm. A transducer accordingly sized is believed to form a lesion of a width sufficient to ensure the integrity of the formed conductive block without undue tissue ablation. For other applications, however, the length can be significantly longer.

Likewise, the transducer outer diameter desirably is selected to account for delivery through a particular access path (e.g., percutaneously and transeptally), for proper placement and location within a particular body space, and for achieving a desired ablation effect. The positioning of the transducer within an inflatable member, e.g., a balloon, may be desirable for facilitating the positioning of the transducer within a pulmonary vein or pulmonary vein ostium at a suitable distance for delivering a circumferential lesion. The transducer preferably has an outer diameter within the range of about 1.8 mm to greater than 2.5 mm. It has been observed that a transducer with an outer diameter of about 2 mm generates acoustic power levels approaching 20 Watts per centimeter radiator or greater within myocardial or vascular tissue, which is believed to be sufficient for ablation of tissue engaged by an outer balloon for up to about 2 cm outer diameter of the balloon. For applications in other body spaces, the transducer applicator may have an outer diameter within the range of about 1 mm to greater than 3–4 mm (e.g., as large as 1 to 2 cm for applications in some body spaces).

For this purpose, the transducer seats coaxial about the inner member and is supported about the inner member in a manner providing a gap between the inner member and the transducer inner tubular member. That is, the inner tubular member forms an interior bore that loosely receives the inner member. Any of a variety of structures can be used to support the transducer about the inner member. For instance, spacers or splines can be used to coaxially position the transducer about the inner member while leaving a generally annular space between these components. In the alternative, other conventional and known approaches to support the transducer can also be used. For instance, O-rings that circumscribe the inner member and lie between the inner member and the transducer can support the transducer. More detailed examples of the alternative transducer support structures just described are disclosed in U.S. Pat. No. 5,620,479 to Diederich, issued Apr. 15, 1997, and entitled "Method and Apparatus for Thermal Therapy of Tumors," and U.S. Pat. No. 5,606,974 to Castellano, issued Mar. 4, 1997, and entitled "Catheter Having Ultrasonic Device."

Figure 32A:
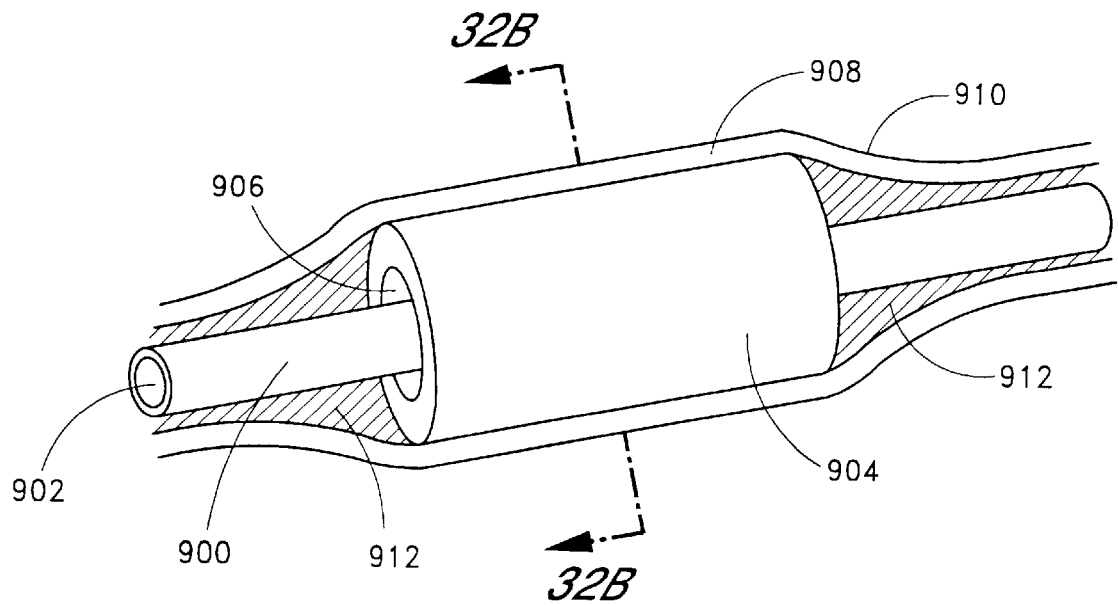
FIG. 32A is a perspective view of a suspended coaxial ultrasound transducer wherein an outer layer is used to suspend the transducer over the probe such that a radial separation is maintained therebetween.
Figure 32B:
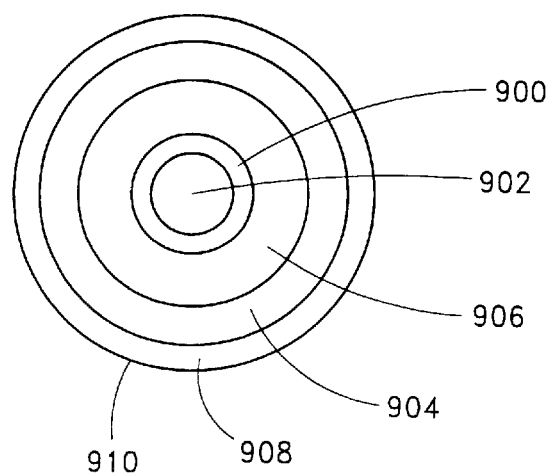
FIG. 32B is a cross-sectional view taken along line 32B—32B through the transducer of FIG. 32A.

In one embodiment, suspending the transducer from an external protective layer resolves problems associated with maintaining a minimally damped internal mounting scheme. With reference to FIGS. 32A and 32B, the external layer coupled to the transducer with a coupling adhesive is described below.

The transducer 904 is generally coaxially disposed over the tracking member 900; however, it is understood that the transducer 904 can be asymmetrically positioned relative to an axis of the guide member tracking member 900 provided an air gap exists between the transducer inner surface and the tracking member 900. An air space 906 exists between the transducer 904 and the tracking member 900, thereby providing an air-backing to maximize the outward radiation of the ultrasonic energy, as described above.

The transducer 904 is held suspended over the tracking member 900 by the cooperative arrangement of an outer cover 910, for example, a shrink-wrap polymeric material (e.g., PET), and end plugs 912 bonded to a length of the tracking member 900 proximal and distal to the transducer 904. In the embodiment illustrated in FIGS. 32A and B, the end plugs 912 are formed of adhesive and lie under the cover 910, and a layer of adhesive 908 covers the transducer 904 and couples the transducer 904 to an inner surface of the outer cover 910.

The proper air gap may be ensured during setting of the adhesive end plugs 912 by inserting three or more beading mandrels between the tracking member and the transducer. These mandrels would preferably be evenly distributed radially about the tracking member 900 and would run axially along the length of the transducer 910. The beading mandrels can be sized so as to create a desired air gap (e.g., 0.005 inches (0.13 mm)). Since the mandrels must be removed, it is preferred that the beading mandrels be made out of a material to which the epoxy adhesive will not stick, such as for example, metal or silicone, and extend beyond one end of the transducer 904 during the assembly process.

FIG. 32B is a cross-sectional view through the transducer along line B—B of FIG. 32A. The thickness of the adhesive layer can be in the range of about 0.0005 (0.013 mm) to about 0.001 inches (0.025 mm). The cover can have a thickness in the range of about 0.001 to about 0.003 inches.

In addition, the present embodiment may also include an external cover layer surrounding the ablation member. The material may be a thermoset elastomer, such as urethane or silicon rubber. Alternatively, the material could be a thermoplastic polymer, such as polyurethane, PET, or any other polymeric thermoplastic. The material could also be an adhesive.

In an alternative embodiment, the transducer may be suspended by mounting flanges which extend from either end of the transducer. The mounting flanges may be formed in a variety of configurations. An end cap made of suitable plastic or elastomer may also receive the mounting flange.

The embodiments described herein are particularly useful in assemblies adapted for ablating a circumferential region of tissue where a pulmonary vein extends from a left atrium in the treatment of atrial fibrillation, as noted above. The circumferential pulmonary vein ablation aspect of the invention is therefore suited for combination or aggregation with, or where appropriate in substitution for, the various features and embodiments disclosed in the following patents and co-pending U.S. Patent Applications that also address circumferential ablation at a location where a pulmonary vein extends from an atrium: U.S. Ser. No. 08/889,798 for "Circumferential Ablation Device Assembly" to Lesh et al., filed Jul. 8, 1997, now U.S. Pat. No. 6,024,740, issued on Feb. 15, 2000; U.S. Ser. No. 08/889,835 for "Device and Method for Forming a Circumferential Conduction Block in a Pulmonary Vein" to Lesh, filed Jul. 8, 1997, now U.S. Pat. No. 6,012,457, issued Jan. 11, 2000; U.S. Ser. No. 09/199, 736 for "Circumferential Ablation Device Assembly" to Diederich et al., filed Feb. 3, 1998, now U.S. Pat. No. 6,117,101, issued Sep. 12, 2000; and U.S. Ser. No. 09/260, 316 for "Tissue Ablation Device Assembly and Method of Forming a Conduction Block Along a Length of Tissue" to Langberg et al., filed Mar. 1, 1999. The disclosures of these references are herein incorporated in their entirety by reference thereto.

It is further contemplated that the embodiments and variations thereof shown and described herein may be combined, assembled together, or where appropriate substituted for, the various features and embodiments which are disclosed in the following patents and U.S. Patent Applications: U.S. Ser. No. 09/517,614, filed on Mar. 2, 2000 for "MEDICAL DEVICE WITH SENSOR COOPERATING WITH EXPANDABLE MEMBER"; U.S. Ser. No. 09/435, 283, filed on Nov. 5, 1999 for "CIRCUMFERENTIAL ABLATION DEVICE ASSEMBLY AND METHODS OF USE AND MANUFACTURE PROVIDING AN ABLATIVE CIRCUMFERENTIAL BAND ALONG AN EXPANDABLE MEMBER"; U.S. Ser. No. 09/569,735 for "BALLOON ANCHOR WIRE", filed May 11, 2000; U.S. Ser. No. 09/435,281, filed on Nov. 5, 1999 for "TISSUE ABLATION DEVICE ASSEMBLY AND METHOD FOR ELECTRICALLY ISOLATING A PULMONARY VEIN OSTIUM FROM A POSTERIOR LEFT ATRIAL WALL", U.S. Ser. No. 09/435,280, filed on Nov. 5, 1999 for "APPARATUS AND METHOD INCORPORATING AN ULTRASOUND TRANSDUCER ONTO A DELIVERY MEMBER"; and U.S. Ser. No. 09/517,472, filed on Mar. 2, 2000 for "POSITIONING SYSTEM AND METHOD OF ORIENTING AN ABLATION ELEMENT WITHIN A PULMONARY VEIN." The disclosures of these references are herein incorporated in their entirety by reference thereto.

In addition, such a circumferential ablation device assembly may be used in combination with other linear ablation assemblies and methods, as noted above, and various related components or steps of such assemblies or methods, respectively, in order to form a circumferential conduction block adjunctively to the formation of long linear lesions, such as in a less-invasive "maze"-type procedure. Examples of such assemblies and methods related to linear lesion formation and which are contemplated in combination with the presently disclosed embodiments are shown and described in the following additional patents and U.S. Patent Applications: U.S. Pat. No. 5,971,983, issued on Oct. 26, 1999, entitled "TISSUE ABLATION DEVICE AND METHOD OF USE" filed by Lesh on May 9, 1997; U.S. Ser. No. 09/260,316 for "TISSUE ABLATION SYSTEM AND METHOD FOR FORMING A CONDUCTION BLOCK ALONG A LENGTH OF TISSUE" to Langberg et al., filed May 1, 1999; and U.S. Ser. No. 09/073,907 for "IRRIGATED ABLATION DEVICE ASSEMBLY", to Schaer et al., filed May 6, 1998. The disclosures of these references are also herein incorporated in their entirety by reference thereto.

While a number of variations of the invention have been shown and described in detail, other modifications and methods of use contemplated within the scope of this invention will be readily apparent to those of skill in the art based upon this disclosure. It is contemplated that various combinations or sub-combinations of the specific embodiments may be made and still fall within the scope of the invention. Moreover, all assemblies described are believed useful when modified to treat other tissues in the body, in particular other regions of the heart, such as the coronary sinus and surrounding areas. Further, the disclosed assemblies may be useful in treating other conditions, wherein aberrant electrical conduction may be implicated, such as for example, heart flutter. Indeed, other conditions wherein probe-based, directed tissue ablation may be indicated, such as for example, in the ablation of fallopian tube cysts. Accordingly, it should be understood that various applications, modifications and substitutions may be made of equivalents without departing from the spirit of the invention.

What is claimed is:

1. A surgical ablation probe for ablating a circumferential region of tissue at a location where a pulmonary vein extends from an atrium, comprising:
    a rigid shaft configured for insertion through an opening in a patient's chest, the rigid shaft having proximal and distal end portions and a longitudinal axis, wherein said distal end portion has a preset angle relative to said longitudinal axis of said shaft;
    a handle coupled to said proximal end portion of said shaft for manipulating said surgical ablation probe; and
    a circumferential ablation member mounted on said distal end portion and adapted for ablating said circumferential region of tissue, wherein said preset angle in said distal end portion of said shaft is adapted to facilitate placement of said circumferential ablation member at said location.

2. The surgical ablation probe of claim 1, wherein said distal end portion of said shaft is deflectable, such that deflection of said distal end portion changes said angle.

3. The surgical ablation probe of claim 2, further comprising a deflection mechanism with a deflection actuator disposed on said handle.

4. The surgical ablation probe of claim 3, wherein said deflection mechanism comprises a pull wire having proximal and distal ends, said proximal end of said pull wire coupled to said deflection actuator and said distal end of said pull wire coupled to said distal end portion of said shaft.

5. The surgical ablation probe of claim 1, further comprising an anchoring member located along said distal end portion of said shaft for releasably anchoring said circumferential ablation member at said location.

6. The surgical ablation probe of claim 5, wherein said anchoring member comprises an expandable member.

7. The surgical ablation probe of claim 6, further comprising an expansion actuator in fluid communication with said expandable member and a pressurized fluid source, wherein actuation of said expansion actuator causes pressurized fluid to radially expand said expandable member.

8. The surgical ablation probe of claim 6, wherein said expandable member comprises an inflatable balloon.

9. The surgical ablation probe of claim 1, wherein said ablation member comprises a cylindrical ultrasound transducer coaxially disposed over said distal end portion of said shaft.

10. The surgical ablation probe of claim 9, wherein said ultrasound transducer has an inner wall and an inner diameter which is greater than an outer diameter of said shaft, such that an air gap is provided in a radial separation between said inner wall of said ultrasound transducer and said shaft.

11. The surgical ablation probe of claim 10, further comprising a support structure coupled to said ultrasound transducer and said shaft so as to maintain said radial separation therebetween.

12. The surgical ablation probe of claim 1, wherein said circumferential ablation member further comprises a circumferential band adapted to ablatively couple to said circumferential region of tissue.

13. The surgical ablation probe of claim 12, wherein said circumferential band comprises at least one ablation electrode electrically coupled to an electrical current source.

14. The surgical ablation probe of claim 1, further comprising a radiopaque marker disposed along said shaft.

15. The surgical ablation probe of claim 1, further comprising a thermocouple positionable along said circumferential region of tissue for providing temperature feedback.

16. The surgical ablation probe of claim 1, further comprising a biocompatible outer extrusion on an outer surface of said shaft.

17. A surgical ablation probe for ablating a circumferential region of tissue at a location where a pulmonary vein extends from an atrium, comprising:
    a substantially rigid shaft configured for insertion through an opening in a patient's chest, the substantially rigid shaft having proximal and distal end portions and a longitudinal axis, wherein said distal end portion has an angle relative to said longitudinal axis of said shaft and said distal end portion of said shaft is deflectable by manipulation of a pull-wire system, such that deflection of said distal end portion changes said angle;
    a handle coupled to said proximal end portion of said shaft for manipulating said surgical ablation probe;
    a cylindrical ultrasound transducer coaxially disposed over said distal end portion of said shaft and adapted for ablating said circumferential region of tissue, wherein said angle in said distal end portion of said shaft is adapted to facilitate placement of said ultrasound transducer at said location; and
    an anchoring member located along said distal end portion of said shaft for releasably anchoring said ultrasound transducer at said location.

18. A surgical ablation probe for ablating a circumferential region of tissue at a location where a pulmonary vein extends from an atrium, comprising:
    a substantially rigid shaft configured for insertion through an opening in a patient's chest, the substantially rigid shaft having proximal and distal end portions and a longitudinal axis, wherein said distal end portion has an angle relative to said longitudinal axis of said shaft;
    a handle coupled to said proximal end portion of said shaft for manipulating said surgical ablation probe; and
    a circumferential ablation member mounted on said distal end portion and adapted for ablating said circumferential region of tissue, the circumferential ablation member including an expandable member and one or more ablation elements, the ablation elements being mounted on the outer surface of the expandable member.

19. A surgical ablation probe for ablating a circumferential region of tissue at a location where a pulmonary vein extends from an atrium, comprising:
    a substantially rigid shaft configured for insertion through an opening in a patient's chest, the substantially rigid shaft having proximal and distal end portions and a longitudinal axis, wherein said distal end portion has an angle relative to said longitudinal axis of said shaft;
    a handle coupled to said proximal end portion of said shaft for manipulating said surgical ablation probe; and a circumferential ablation member mounted on said distal end portion and adapted for ablating said circumferential region of tissue, the circumferential ablation member including an expandable member and an ablation element, the ablation element being mounted on the substantially rigid shaft inside the expandable member.

20. A surgical ablation probe for ablating a circumferential region of tissue at a location where a pulmonary vein extends from an atrium, comprising:

a shaft configured for insertion through an opening in a patient's chest, the shaft including a substantially rigid proximal end portion having a longitudinal axis and a deflectable distal end portion, wherein said distal end portion is deflectable by manipulation of a pull-wire system to deflect the distal end portion at an angle relative to said longitudinal axis of the proximal end portion;

a handle coupled to said proximal end portion of said shaft for manipulating said surgical ablation probe;

a circumferential ablation member mounted on said distal end portion and adapted for ablating said circumferential region of tissue, wherein said angle of said distal end portion of said shaft is adapted to facilitate placement of said circumferential ablation member at said location.

21. A surgical ablation probe for ablating a circumferential region of tissue at a location where a pulmonary vein extends from an atrium, comprising:

a substantially rigid shaft configured for insertion through an opening in a patient's chest, the substantially rigid shaft having proximal and distal end portions and a longitudinal axis, wherein said distal end portion has an angle relative to said longitudinal axis of said shaft;

a handle coupled to said proximal end portion of said shaft for manipulating said surgical ablation probe; and a circumferential ablation member mounted on said distal end portion and adapted for ablating said circumferential region of tissue, wherein said angle in said distal end portion of said shaft is adapted to facilitate placement of said circumferential ablation member at said location, said ablation member comprising a cylindrical ultrasound transducer coaxially disposed over said distal end portion of said shaft, wherein said ultrasound transducer has an inner wall and an inner diameter which is greater than an outer diameter of said shaft, such that an air gap is provided in a radial separation between said inner wall of said ultrasound transducer and said shaft.

22. The surgical ablation probe of claim 21, further comprising a support structure coupled to said ultrasound transducer and said shaft so as to maintain said radial separation therebetween.

* * * * *